US006177401B1

(12) United States Patent
Ullrich et al.

(10) Patent No.: US 6,177,401 B1
(45) Date of Patent: Jan. 23, 2001

(54) USE OF ORGANIC COMPOUNDS FOR THE INHIBITION OF FLK-1 MEDIATED VASCULOGENESIS AND ANGIOGENESIS

(75) Inventors: Axel Ullrich, München; Werner Risau, Grafelfing; Birgit Millauer, München, all of (DE)

(73) Assignee: Max-Planck-Gesellschaft zur Forderung der Wissenschaften, Martinsried (DE)

( * ) Notice: Under 35 U.S.C. 154(b), the term of this patent shall be extended for 0 days.

(21) Appl. No.: 08/193,829

(22) Filed: Feb. 9, 1994

Related U.S. Application Data

(63) Continuation-in-part of application No. 08/038,596, filed on Mar. 26, 1993, now abandoned, which is a continuation-in-part of application No. 07/975,750, filed on Nov. 13, 1992, now abandoned.

(51) Int. Cl.[7] .................................................. A61K 31/00
(52) U.S. Cl. ................. 514/1; 435/7.2; 436/501; 530/350; 530/399
(58) Field of Search .................. 536/23.5; 435/69.1, 435/172.1, 240.2, 252.3, 320.1, 325, 361, 7.2; 424/93.2; 514/44, 1; 935/32, 57, 70, 71; 436/501; 530/399, 350

(56) References Cited

U.S. PATENT DOCUMENTS

| 5,185,438 | 2/1993 | Lemishka . |
| 5,712,395 | 1/1998 | App et al. . |
| 5,763,441 | 6/1998 | App et al. . |
| 5,766,860 | 6/1998 | Terman et al. . |
| 5,792,771 | 8/1998 | App et al. . |
| 5,792,783 | 8/1998 | Tang et al. . |
| 5,869,742 | 2/1999 | Köster et al. . |

FOREIGN PATENT DOCUMENTS

| WO 92/03459 | 3/1992 | (WO) . |
| WO 92/14748 | 9/1992 | (WO) . |
| WO 92/17486 | 10/1992 | (WO) . |
| WO 94/10202 | 5/1994 | (WO) . |
| WO 95/21868 | 8/1995 | (WO) . |
| WO 96/20403 | 7/1996 | (WO) . |

OTHER PUBLICATIONS

S.H. Orkin Et Al., "Report and Recommendations of the Panel to Assess the NIH Investment in Research on Gene Therapy", Dec. 7, 1995.*
H. Ueno et al.., Science 252:844–848, May 10, 1991.*
H. Ueno et al.., J. Biol. Chem. 267(3):1470–1476, Jan. 25, 1992.*
L.A. Tartaglia et al., J. Biol. Chem. 267(7), 4304–4307, Mar. 5, 1992.*
Risau et al., 1988, "Changes in the Vascular Extracellular Matrix During Embryonic Vasculogenesis and Angiogenesis," *Development Biology* 125:441–450.
Ferrara et al., 1989, "Pituitary Follicular Cells Secrete a Novel Heparin–Binding Growth Factor Specific for Vascular Endothelial Cells," *Biochem. Biophys. Res. Comm.* 161:851–858.
Gospodarowicz et al., 1989, "Isolation and Characterization of a Vascular Endothelial Cell Mitogen Produced by Pituitary–Derived Folliculo Stellate Cells," *Proc. Natl. Acad. Sci. USA* 86:7311–7315.
Leung et al., 1989, "Vascular Endothelial Growth Factor Is a Secreted Angiogenic Mitogen," *Science* 246:1306–1309.
Conn et al., 1990, "Purification of a Glycoprotein Vascular Endothelial Cell Mitogen From a Rat Glioma–derived Cell Line," *Proc. Natl. Acad. Sci. USA* 87:1323–1327.
Ullrich et al., 1990, "Signal transduction by receptors with tyrosine kinase activity", *Cell* 61:203–212.
Ferrara et al., 1991, "The Vascular Endothelial Growth Factor Family of Polypeptides," *J. Cell Biochem.* 47:211–218.
Kashles et al., 1991, "A Dominant Negative Mutation Suppresses the Function of Normal Epidermal Growth Factor Receptors by Heterodimerization," *Mol. Cell. Biol.* 11:1454–1463.
Klagsburn et al., 1991, "Regulators of Angiogenesis" *Annu. Rev. Physiol.* 53:217–39.
Maglione et al., 1991, "Isolation of Human Placental cDNA Coding For a Protein Related to the Vascular Permeability Factor," *Proc. Natl. Acad. Sci. USA* 88:9267–9271.
Matthews et al., 1991, "A Receptor Tyrosine Kinase cDNA Isolated From a Population of Enriched Primative Hematopoietic Cells and Exhibiting Close Genetic Linkage to c–kit," *Proc. Natl. Acad. Sci. USA* 88:9026–9030.
Mitchell et al., 1991, "Recombinant Expression and Characterization of the 121 Amino Acid Form of Vascular Endothelial Growth Factor (VEGF)," *J. Cell. Biochem., Keystone Symposia on Molecular and Cellular Biology*, Supplement 15C, Excerpt G207.

(List continued on next page.)

Primary Examiner—Lorraine Spector
(74) Attorney, Agent, or Firm—Foley & Lardner

(57) ABSTRACT

The present invention relates to the use of proteins, peptides and organic molecules capable of modulating Flk-1 receptor signal transduction in order to inhibit or promote angiogenesis and vasculogenesis. The invention is based, in part, on the demonstration that Flk-1 tyrosine kinase receptor expression is associated with endothelial cells and the identification of vascular endothelial growth factor (VEGF) as the high affinity ligand of Flk-1. These results indicate a major role for Flk-1 in the signaling system during vasculogenesis and angiogenesis. Engineering of host cells that express Flk-1 and the uses of expressed Flk-1 to evaluate and screen for drugs and analogs of VEGF involved in Flk-1 modulation by either agonist or antagonist activities is described.

Figure 3A:

The invention also relates to the use of FLK-1 ligands, including VEGF agonists and antagonists, in the treatment of disorders, including cancer, by modulating vasculogenesis and angiogenesis.

16 Claims, 25 Drawing Sheets

OTHER PUBLICATIONS

Terman et al., 1991, "Identification of a New Endothelial Cell Growth Factor Receptor Tyrosine Kinase," *Oncogene* 6:1677–1683.

Breier et al., 1992, "Expression of Vascular Endothelial Growth Factor During Embryonic Angiogenesis and Endothelial Cell Differentiation," *Development* 114:521–532.

De Vries et al., 1992, "The fms–Like Tyrosine Kinase, a Receptor for Vascular Endothelial Growth Factor," *Science* 255:989–991.

Sarzani et al., 1992, "A Novel Endothelial Tyrosine Kinase cDNA Homologous To Platelet–Derived Growth Factor Receptor cDNA" *Biochem. Biophys. Res. Comm.* 186:706–714.

Spivak–Kroizman et al., 1992, "Heterodimerization of c–erbB2 With Different Epidermal Growth Factor Receptor Mutants Elicit Stimulatory or Inhibitory Responses," *J. Biol. Chem.* 267:8056–8063.

Terman et al., 1992, "Identification of the KDR Tyrosine Kinase as a Receptor for Vascular Endothelial Cell Growth Factor," *Biochem. Biophys. Res. Comm.* 187:1579–1586.

Plate et al., 1993, "Up–Regulation of Vascular Endothelial Growth Factor and Its Cognate Receptors in a Rat Glioma Model of Tumor Angiogenesis," *Cancer Research* 53:5822–5827.

Livneh et al., 1986, "Reconstitution of human epidermal growth factor receptors and its deletion mutants in cultured hamster cells," *J. Biol. Chem.* 261(27):12490–12497.

McCormick, 1985, "Human gene therapy: The first round," *Biotechnology* 3(8):689–693.

McMahon et al., 1998, "Protein kinase inhibitors: structural determinants for target specificity," *Current Opinions in Drug Descovery and Development* 1(2):131–146.

Millauer et al., 1993, "High affinity VEGF binding and development expression suggest Flk–1 as a major regulator of vasculogenesis and angiogenesis," *Cell* 72(^):835–846.

Nicolas et al., 1987, "Retroviral Vectors," *Vectors*, Chapter 25, pp. 493–494.

Prywes et al., 1986, "Mutations in the cytoplasmic domain of EGF receptor affect EGF binding and receptor internalization," *EMBO J.* 5(9):2179–2190.

Strawn et al., 1996, "Flk–1 as a Target for Tumor Growth Inhibition," *Cancer Research* 56:3540–3545.

Traxler, 1998, "Tyrosine kinase inhibitors in cancer treatment (Part II)," *Exp. Opin. Ther. Patents* 8(12):1599–1625.

* cited by examiner

FIG. 1

```
FLK-1  866  ILIHIGHHLNVVNLLGACTKPGGPLMVIVEFSKFGNLSTYLRGKRNEFVPYKSKGARFRQ
KDR         ------------------------------C--D-------S----------T-------
TKR-C       ------------------------------C-------------------------S

FLK-1  926  GKDYVGELSVDLKRRLDSITSSQSSASSGFVEEKSLSDVEEEEASEELYKDFLTLEHLIC
KDR         ------AIP-----------------------------------P-D-------------
TKR-C       ------------------------------------------------------------

FLK-1  986  YSFQVAKGMEFLASRKCIHRDLAARNILLSEKNVVKICDFGLARDIYKDPDYVRKGDARL
KDR         ------------------------------------------------------------
TKR-C       ------------------------------------------------------------
```

FIG. 2A
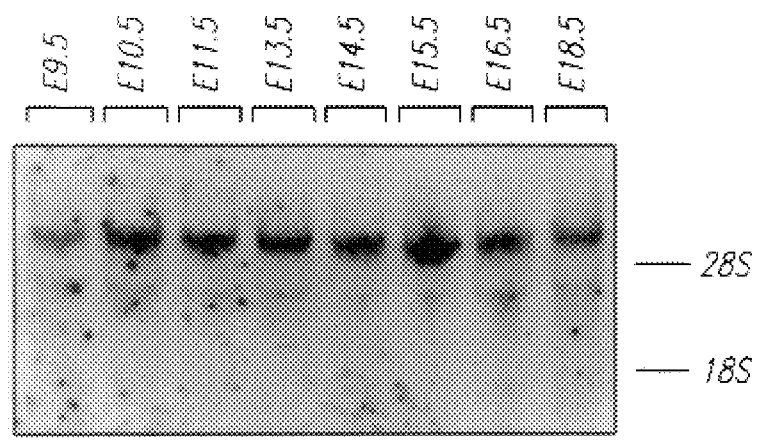
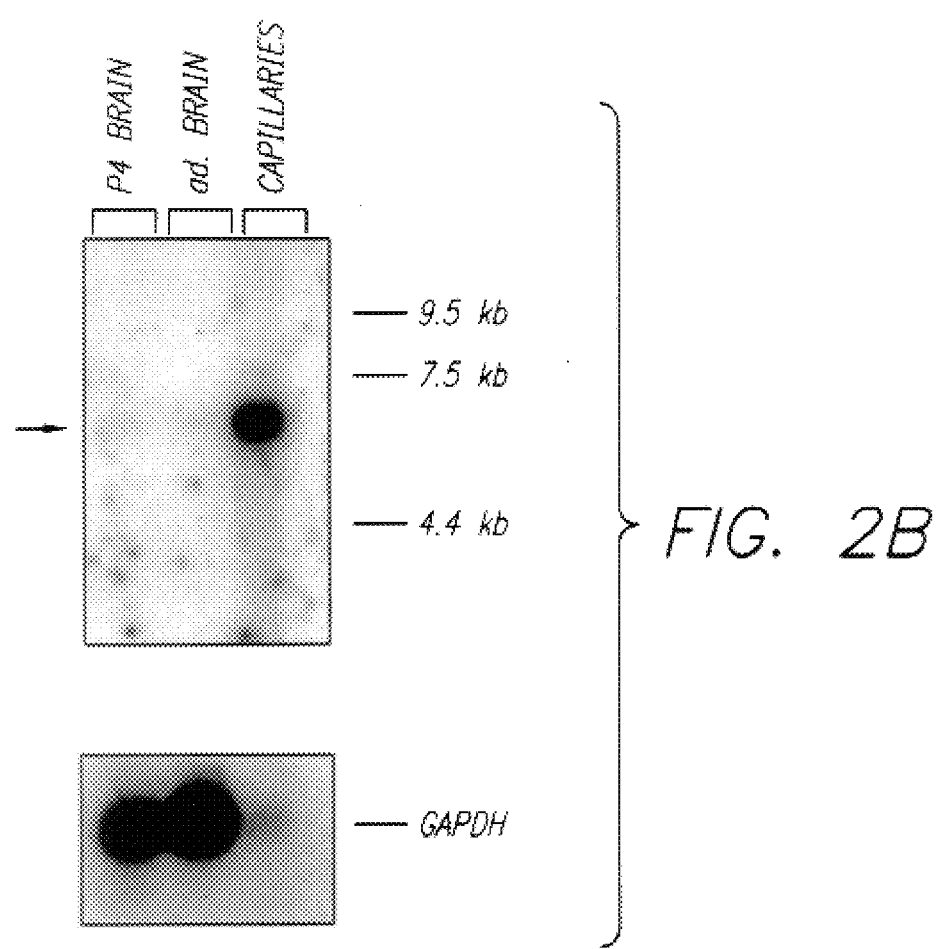
FIG. 2B

FIG. 4A
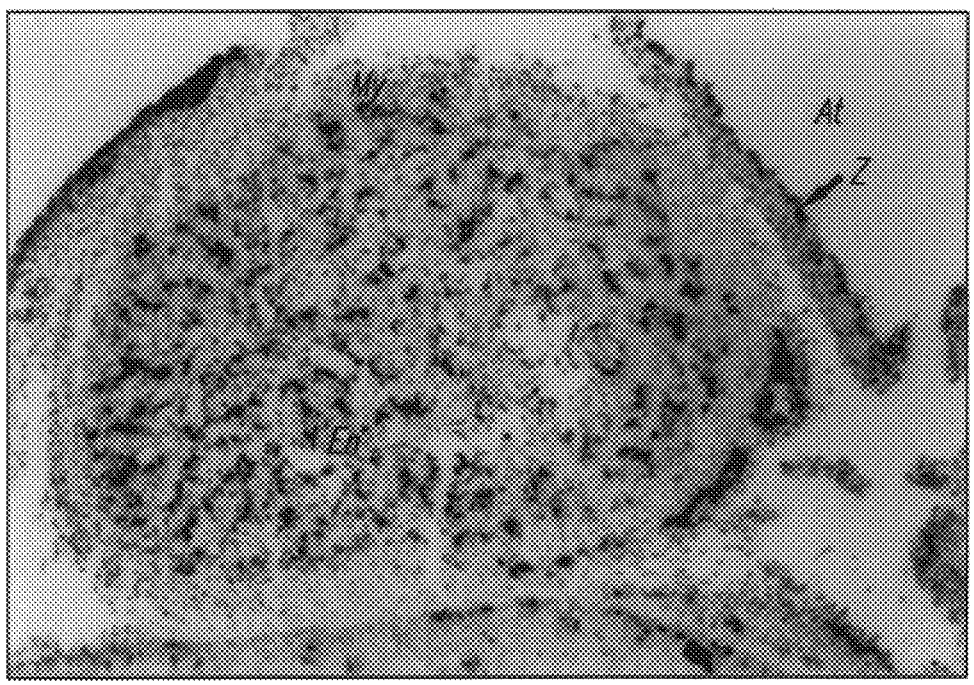
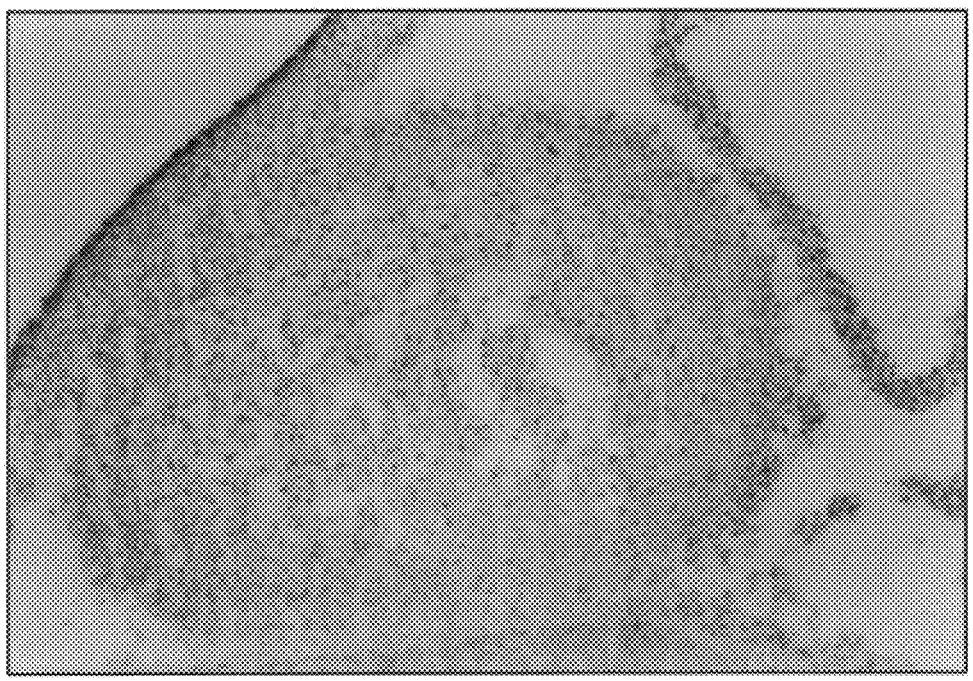
FIG. 4B

FIG. 5A
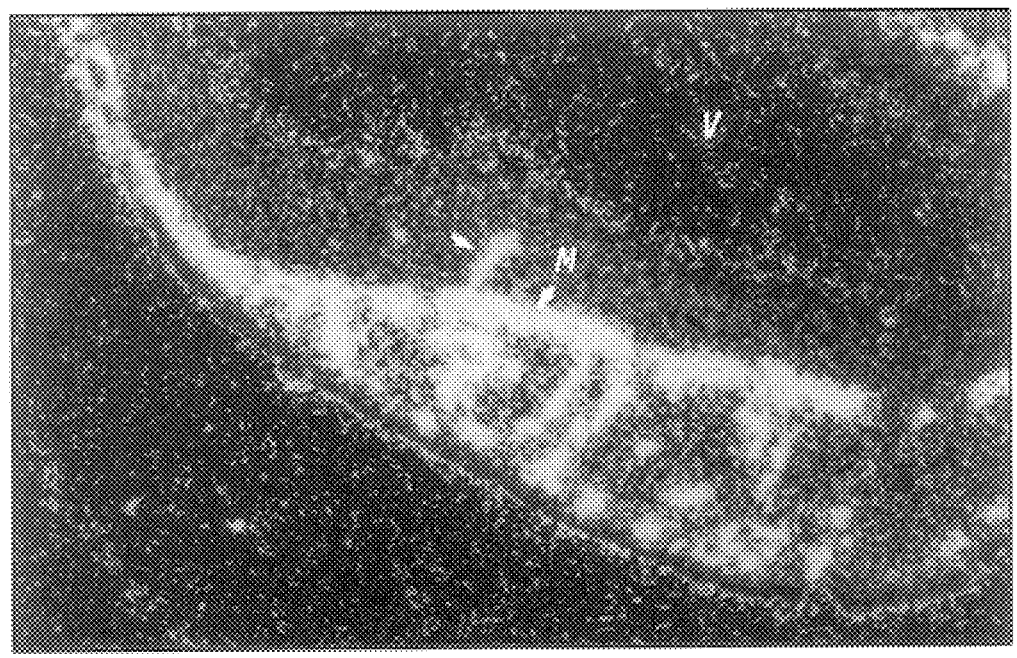
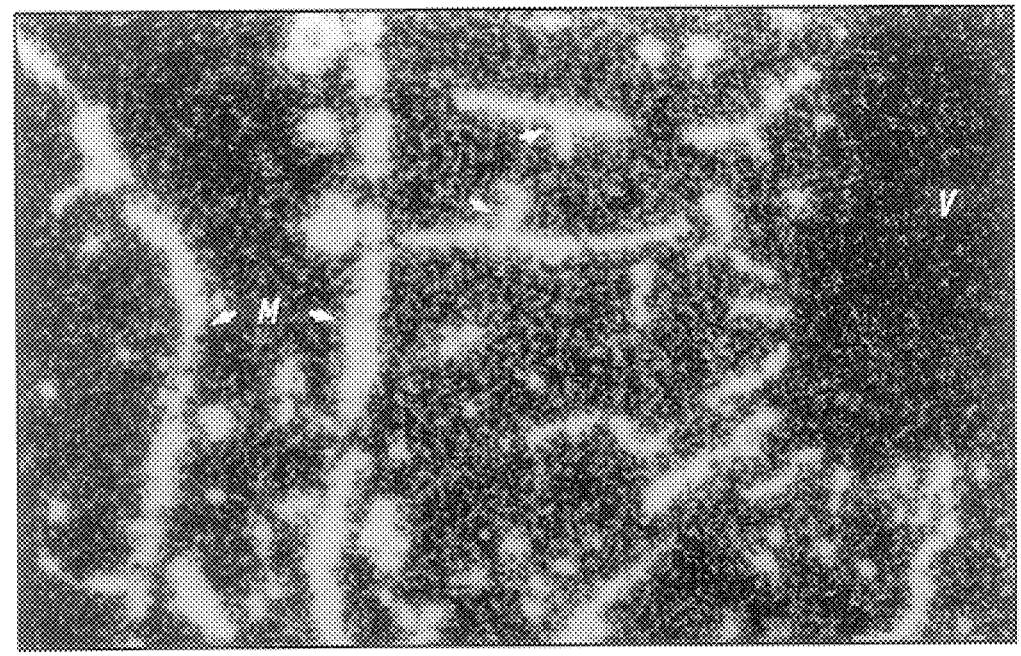
FIG. 5B

FIG. 5C
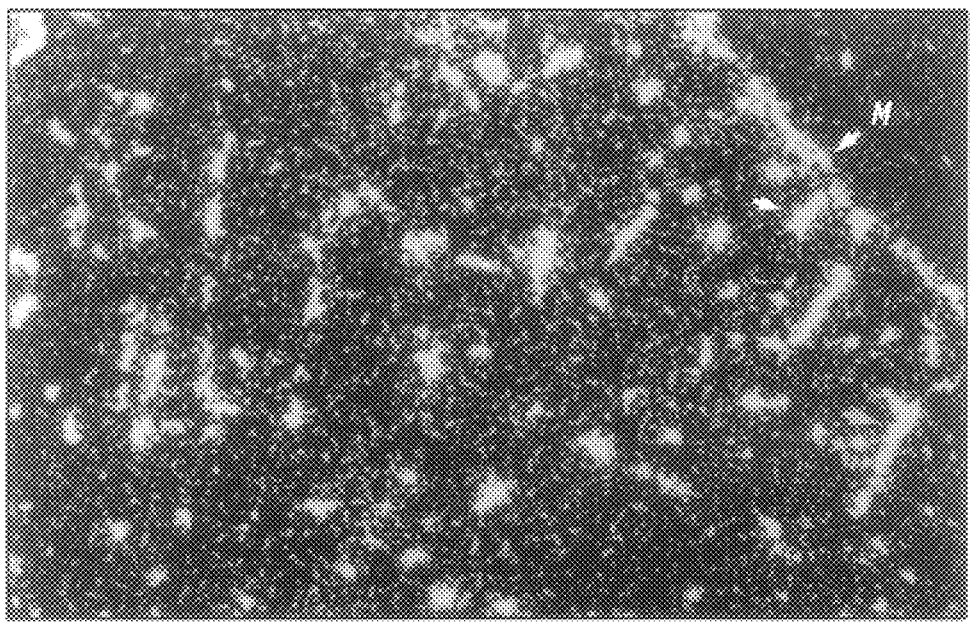
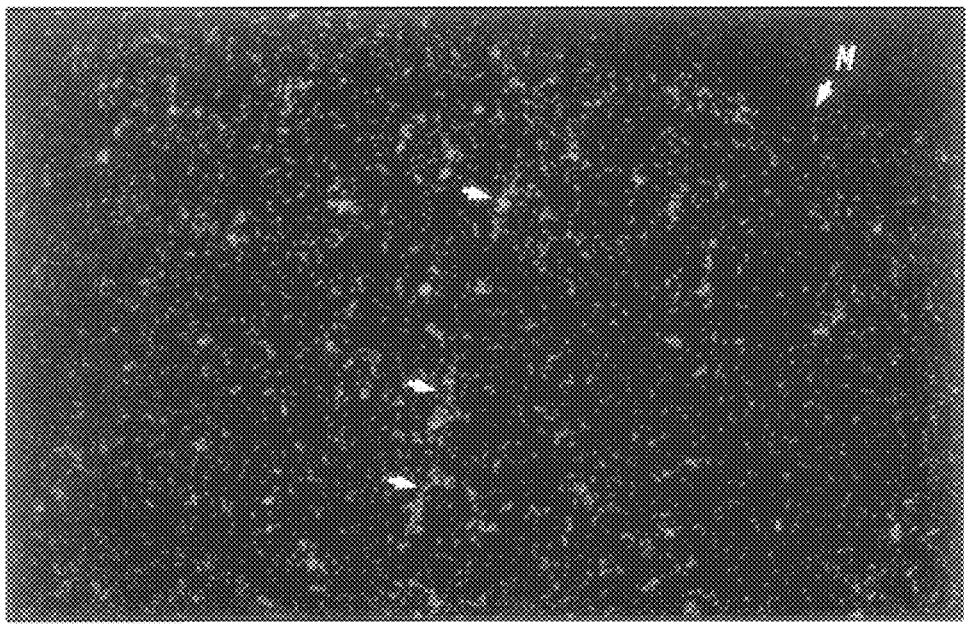
FIG. 5D

FIG. 6A
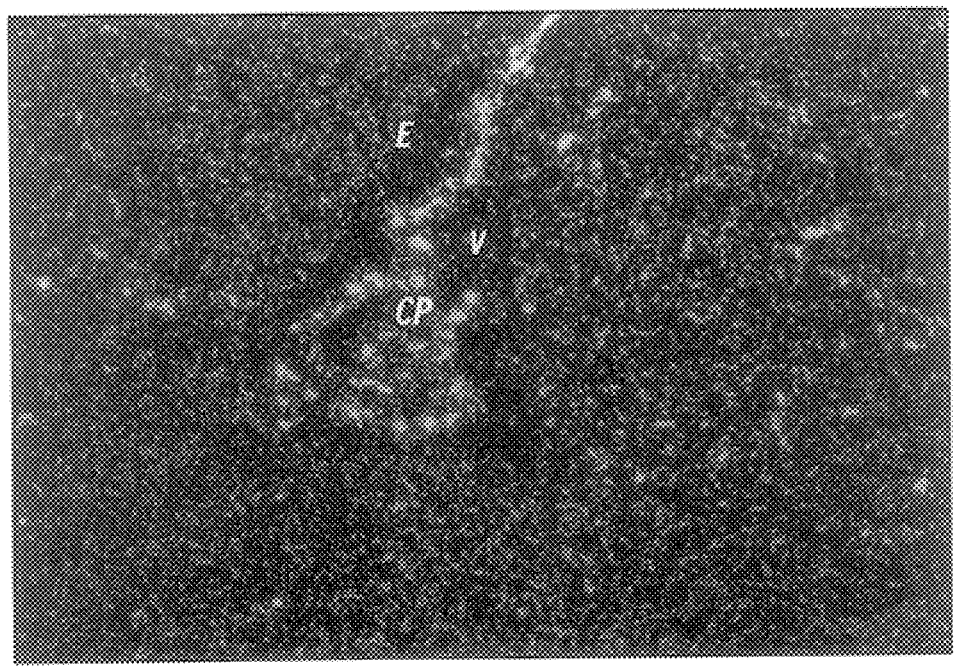
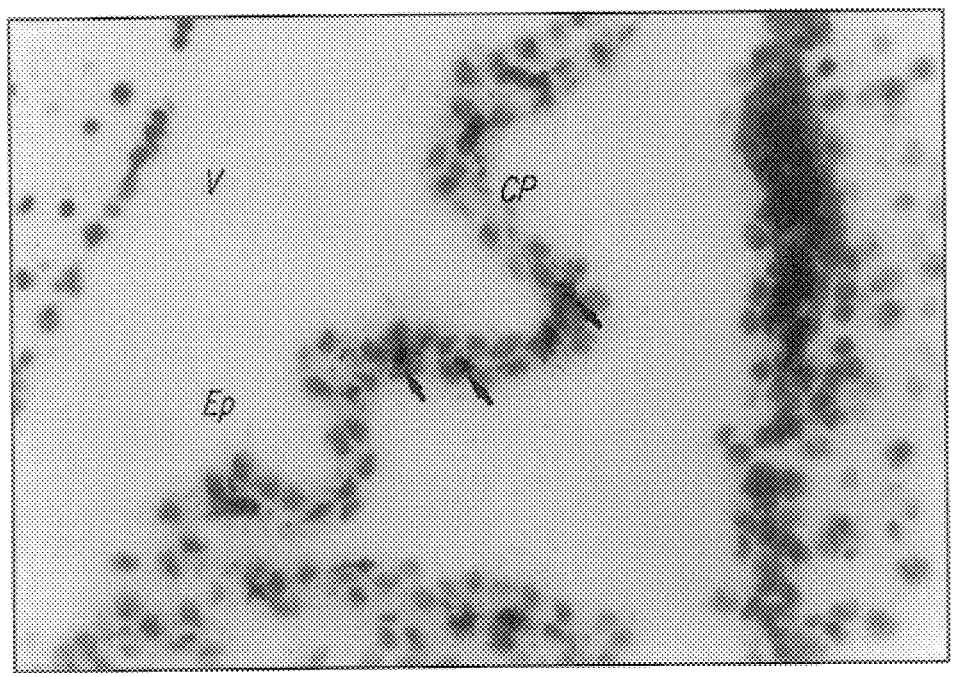
FIG. 6B

FIG. 7A
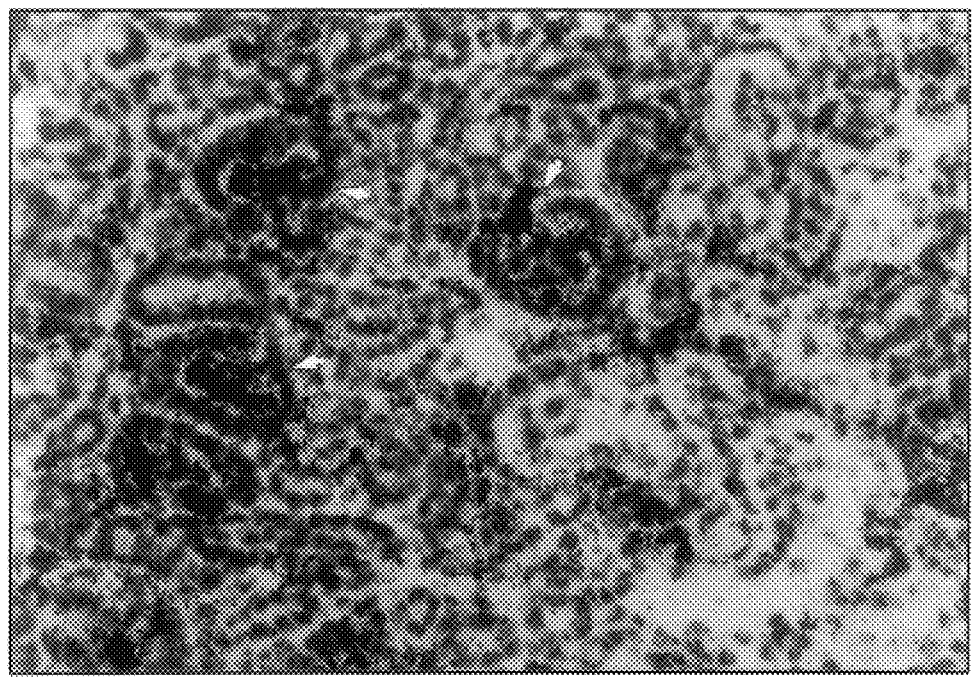
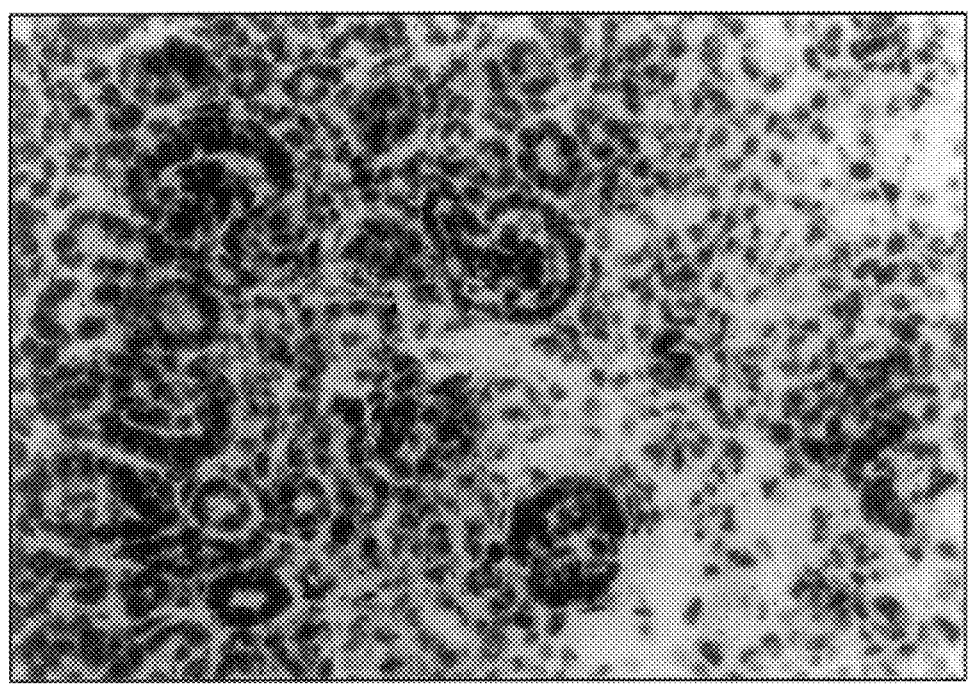
FIG. 7B

FIG. 7C
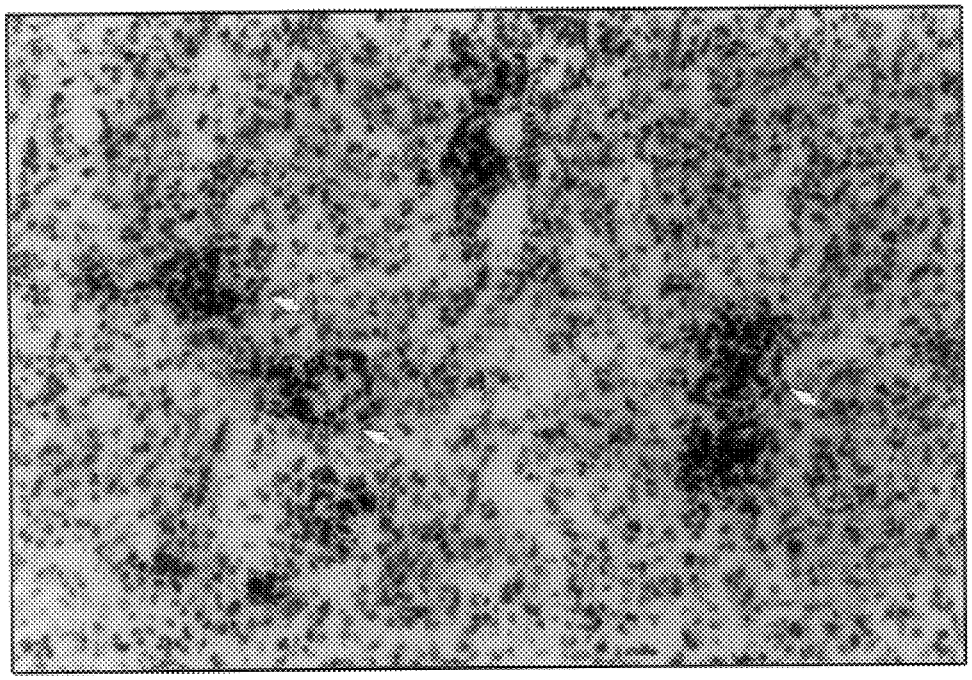
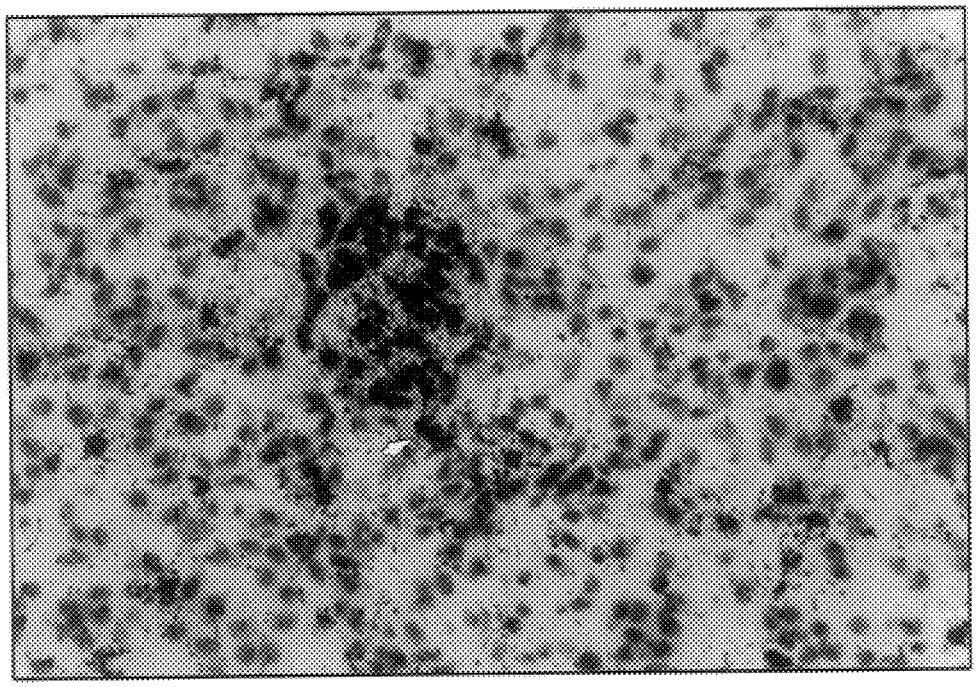
FIG. 7D

FIG. 9B
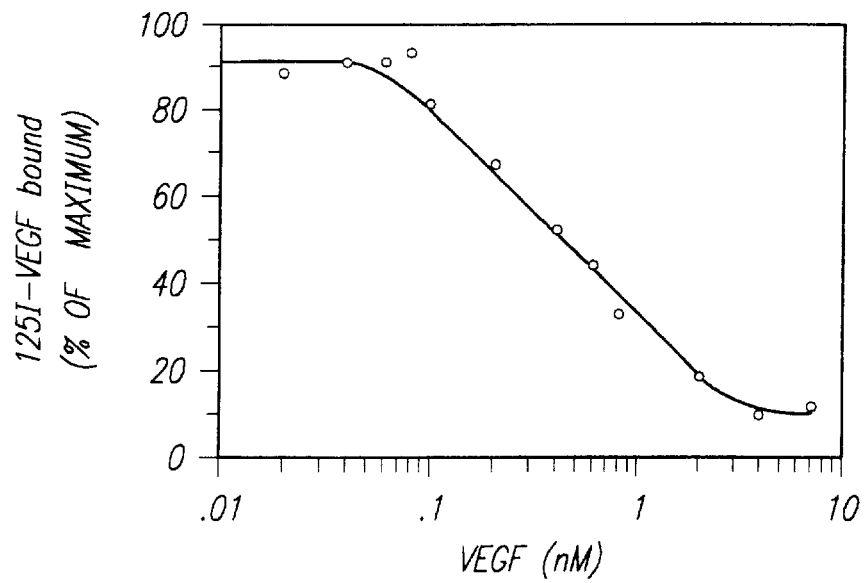
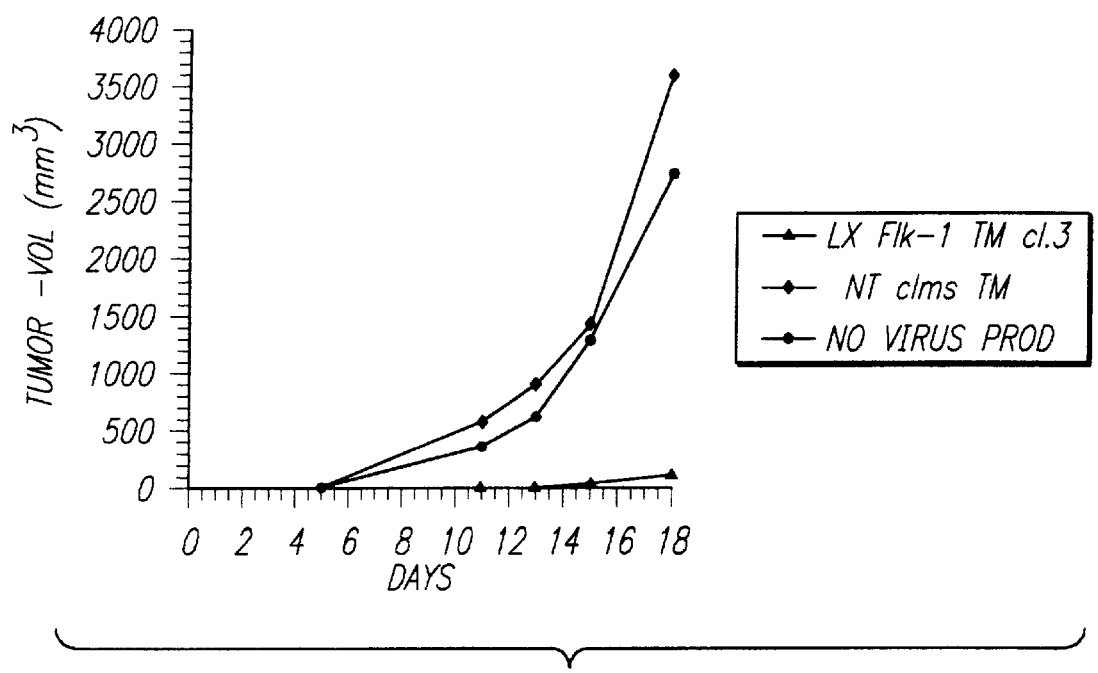
FIG. 13

FIG. 11-1

```
CTGTGTCCCGCAGCCGGGATAACCTGGCTGACCCGATTCCGCGGACACCGCTGACAGCCGCGGCTGGAGCCAGGG    75
CGCCGGTGCCCCGCGCTCTCCCCGGTCTTGCGCTGCGGGGGCCATACCGCCTCTGTGACTTCTTTGCGGGCCAGG    150
GACGGAGAAGGAGTCTGTGCCTGAGAAACTGGGCTCTGTGCCCAGGCGCGAGGTGCAGGATGGAGAGCAAGGCGC    225
                                                        M   E   S   K   A   L

TGCTAGCTGTCGCTCTGTGGTTCTGCGTGGAGACCCGAGCCGCCTCTGTGGGTTTGACTGGCGATTTTCTCCATC    300
 L   A   V   A   L   W   F   C   V   E   T   R   A   A   S   V   G   L   T   G   D   F   L   H   P

CCCCCAAGCTCAGCACACAGAAAGACATACTGACAATTTTGGCAAATACAACCCTTCAGATTACTTGCAGGGGAC    375
 P   K   L   S   T   Q   K   D   I   L   T   I   L   A   N   T   T   L   Q   I   T   C   R   G   Q

AGCGGGACCTGGACTGGCTTTGGCCCAATGCTCAGCGTGATTCTGAGGAAAGGGTATTGGTGACTGAATGCGGCG    450
 R   D   L   D   W   L   W   P   N   A   Q   R   D   S   E   E   R   V   L   V   T   E   C   G   G

GTGGTGACAGTATCTTCTGCAAAACACTCACCATTCCCAGGGTGGTTGGAAATGATACTGGAGCCTACAAGTGCT    525
 G   D   S   I   F   C   K   T   L   T   I   P   R   V   V   G   N   D   T   G   A   Y   K   C   S

CGTACCGGGACGTCGACATAGCCTCCACTGTTTATGTCTATGTTCGAGATTACAGATCACCATTCATCGCCTCTG    600
 Y   R   D   V   D   I   A   S   T   V   Y   V   Y   V   R   D   Y   R   S   P   F   I   A   S   V

TCAGTGACCAGCATGGCATCGTGTACATCACCGAGAACAAGAACAAAACTGTGGTGATCCCCTGCCGAGGGTCGA    675
 S   D   Q   H   G   I   V   Y   I   T   E   N   K   N   K   T   V   V   I   P   C   R   G   S   I

TTTCAAACCTCAATGTGTCTCTTTGCGCTAGGTATCCAGAAAAGAGATTTGTTCCGGATGGAAACAGAATTTCCT    750
 S   N   L   N   V   S   L   C   A   R   Y   P   E   K   R   F   V   P   D   G   N   R   I   S   W

GGGACAGCGAGATAGGCTTTACTCTCCCCAGTTACATGATCAGCTATGCCGGCATGGTCTTCTGTGAGGCAAAGA    825
 D   S   E   I   G   F   T   L   P   S   Y   M   I   S   Y   A   G   M   V   F   C   E   A   K   I

TCAATGATGAAACCTATCAGTCTATCATGTACATAGTTGTGGTTGTAGGATATAGGATTTATGATGTGATTCTGA    900
 N   D   E   T   Y   Q   S   I   M   Y   I   V   V   V   V   G   Y   R   I   Y   D   V   I   L   S

GCCCCCCGCATGAAATTGAGCTATCTGCCGGAGAAAAACTTGTCTTAAATTGTACAGCGAGAACAGAGCTCAATG    975
 P   P   H   E   I   E   L   S   A   G   E   K   L   V   L   N   C   T   A   R   T   E   L   N   V

TGGGGCTTGATTTCACCTGGCACTCTCCACCTTCAAAGTCTCATCATAAGAAGATTGTAAACCGGGATGTGAAAC   1050
 G   L   D   F   T   W   H   S   P   P   S   K   S   H   H   K   K   I   V   N   R   D   V   K   P

CCTTTCCTGGGACTGTGGCGAAGATGTTTTTGAGCACCTTGACAATAGAAAGTGTGACCAAGAGTGACCAAGGGG   1125
 F   P   G   T   V   A   K   M   F   L   S   T   L   T   I   E   S   V   T   K   S   D   Q   G   E

AATACACCTGTGTAGCGTCCAGTGGACGGATGATCAAGAGAAATAGAACATTTGTCCGAGTTCACACAAAGCCTT   1200
 Y   T   C   V   A   S   S   G   R   M   I   K   R   N   R   T   F   V   R   V   H   T   K   P   F

TTATTGCTTTCGGTAGTGGGATGAAATCTTTGGTGGAAGCCACAGTGGGCAGTCAAGTCCGAATCCCTGTGAAGT   1275
 I   A   F   G   S   G   M   K   S   L   V   E   A   T   V   G   S   Q   V   R   I   P   V   K   Y

ATCTCAGTTACCCAGCTCCTGATATCAAATGGTACAGAAATGGAAGGCCCATTGAGTCCAACTACACAATGATTG   1350
 L   S   Y   P   A   P   D   I   K   W   Y   R   N   G   R   P   I   E   S   N   Y   T   M   I   V
```

FIG. 11-2

```
TTGGCGATGAACTCACCATCATGGAAGTGACTGAAAGAGATGCAGGAAACTACACGGTCATCCTCACCAACCCCA 1425
 G  D  E  L  T  I  M  E  V  T  E  R  D  A  G  N  Y  T  V  I  L  T  N  P  I

TTTCAATGGAGAAACAGAGCCACATGGTCTCTCTGGTTGTGAATGTCCCACCCCAGATCGGTGAGAAAGCCTTGA 1500
 S  M  E  K  Q  S  H  M  V  S  L  V  V  N  V  P  P  Q  I  G  E  K  A  L  I

TCTCGCCTATGGATTCCTACCAGTATGGGACCATGCAGACATTGACATGCACAGTCTACGCCAACCCTCCCCTGC 1575
 S  P  M  D  S  Y  Q  Y  G  T  M  Q  T  L  T  C  T  V  Y  A  N  P  P  L  H

ACCACATCCAGTGGTACTGGCAGCTAGAAGAAGCCTGCTCCTACAGACCCGGCCAAACAAGCCCGTATGCTTGTA 1650
 H  I  Q  W  Y  W  Q  L  E  E  A  C  S  Y  R  P  G  Q  T  S  P  Y  A  C  K

AAGAATGGAGACACGTGGAGGATTTCCAGGGGGGAAACAAGATCGAAGTCACCAAAAACCAATATGCCCTGATTG 1725
 E  W  R  H  V  E  D  F  Q  G  G  N  K  I  E  V  T  K  N  Q  Y  A  L  I  E

AAGGAAAAAACAAAACTGTAAGTACGCTGGTCATCCAAGCTGCCAACGTGTCAGCGTTGTACAAATGTGAAGCCA 1800
 G  K  N  K  T  V  S  T  L  V  I  Q  A  A  N  V  S  A  L  Y  K  C  E  A  I

TCAACAAAGCGGGACGAGGAGAGAGGGTCATCTCCTTCCATGTGATCAGGGGTCCTGAAATTACTGTGCAACCTG 1875
 N  K  A  G  R  G  E  R  V  I  S  F  H  V  I  R  G  P  E  I  T  V  Q  P  A

CTGCCCAGCCAACTGAGCAGGAGAGTGTGTCCCTGTTGTGCACTGCAGACAGAAATACGTTTGAGAACCTCACGT 1950
 A  Q  P  T  E  Q  E  S  V  S  L  L  C  T  A  D  R  N  T  F  E  N  L  T  W

GGTACAAGCTTGGCTCACAGGCAACATCGGTCCACATGGGCGAATCACTCACACCAGTTTGCAAGAACTTGGATG 2025
 Y  K  L  G  S  Q  A  T  S  V  H  M  G  E  S  L  T  P  V  C  K  N  L  D  A

CTCTTTGGAAACTGAATGGCACCATGTTTTCTAACAGCACAAATGACATCTTGATTGTGGCATTTCAGAATGCCT 2100
 L  W  K  L  N  G  T  M  F  S  N  S  T  N  D  I  L  I  V  A  F  Q  N  A  S

CTCTGCAGGACCAAGGCGACTATGTTTGCTCTGCTCAAGATAAGAAGACCAAGAAAAGACATTGCCTGGTCAAAC 2175
 L  Q  D  Q  G  D  Y  V  C  S  A  Q  D  K  K  T  K  K  R  H  C  L  V  K  Q

AGCTCATCATCCTAGAGCGCATGGCACCCATGATCACCGGAAATCTGGAGAATCAGACAACAACCATTGGCGAGA 2250
 L  I  I  L  E  R  M  A  P  M  I  T  G  N  L  E  N  Q  T  T  T  I  G  E  T

CCATTGAAGTGACTTGCCCAGCATCTGGAAATCCTACCCCACACATTACATGGTTCAAAGACAACGAGACCCTGG 2325
 I  E  V  T  C  P  A  S  G  N  P  T  P  H  I  T  W  F  K  D  N  E  T  L  V

TAGAAGATTCAGGCATTGTACTGAGAGATGGGAACCGGAACCTGACTATCCGCAGGGTGAGGAAGGAGGATGGAG 2400
 E  D  S  G  I  V  L  R  D  G  N  R  N  L  T  I  R  R  V  R  K  E  D  G  G

GCCTCTACACCTGCCAGGCCTGCAATGTCCTTGGCTGTGCAAGAGCGGAGACGCTCTTCATAATAGAAGGTGCCC 2575
 L  Y  T  C  Q  A  C  N  V  L  G  C  A  R  A  E  T  L  F  I  I  E  G  A  Q

AGGAAAAGACCAACTTGGAAGTCATTATCCTCGTCGGCACTGCAGTGATTGCCATGTTCTTCTGGCTCCTTCTTG 2550
 E  K  T  N  L  E  V  I  I  L  V  G  T  A  V  I  A  M  F  F  W  L  L  L  V

TCATTGTCCTACGGACCGTTAAGCGGGCCAATGAAGGGGAACTGAAGACAGGCTACTTGTCTATTGTCATGGATC 2625
 I  V  L  R  T  V  K  R  A  N  E  G  E  L  K  T  G  Y  L  S  I  V  M  D  P
```

FIG. 11-3

```
CAGATGAATTGCCCTTGGATGAGCGCTGTGAACGCTTGCCTTATGATGCCAGCAAGTGGGAATTCCCCAGGGACC 2700
  D  E  L  P  L  D  E  R  C  E  R  L  P  Y  D  A  S  K  W  E  F  P  R  D  R

GGCTGAAACTAGGAAAACCTCTTGGCCGCGGTGCCTTCGGCCAAGTGATTGAGGCAGACGCTTTTGGAATTGACA 2775
  L  K  L  G  K  P  L  G  R  G  A  F  G  Q  V  I  E  A  D  A  F  G  I  D  K

AGACAGCGACTTGCAAAACAGTAGCCGTCAAGATGTTGAAAGAAGGAGCAACACACAGCGAGCATCGAGCCCTCA 2850
  T  A  T  C  K  T  V  A  V  K  M  L  K  E  G  A  T  H  S  E  H  R  A  L  M

TGTCTGAACTCAAGATCCTCATCCACATTGGTCACCATCTCAATGTGGTGAACCTCCTAGGCGCCTGCACCAAGC 2925
  S  E  L  K  I  L  I  H  I  G  H  H  L  N  V  V  N  L  L  G  A  C  T  K  P

CGGGAGGGCCTCTCATGGTGATTCTGCAATTCTCGAAGTTTGGAAACCTATCAACTTACTTACGGGGCAAGAGAA 3000
  G  G  P  L  M  V  I  L  Q  F  S  K  F  G  N  L  S  T  Y  L  R  G  K  R  N

ATGAATTTGTTCCCTATAAGAGCAAAGGGGCACGCTTCCGCCAGGGCAAGGACTACGTTGGGGAGCTCTCCGTGG 3075
  E  F  V  P  Y  K  S  K  G  A  R  F  R  Q  G  K  D  Y  V  G  E  L  S  V  D

ATCTGAAAAGACGCTTGGACAGCATCACCAGCAGCCAGAGCTCTGCCAGCTCAGGCTTTGTTGAGGAGAAATCGC 3150
  L  K  R  R  L  D  S  I  T  S  S  Q  S  S  A  S  S  G  F  V  E  E  K  S  L

TCAGTGATGTAGAGGAAGAAGAAGCTTCTGAAGAACTGTACAAGGACTTCCTGACCTTGGAGCATCTCATCTGTT 3225
  S  D  V  E  E  E  E  A  S  E  E  L  Y  K  D  F  L  T  L  E  H  L  I  C  Y

ACAGCTTCCAAGTGGCTAAGGGCATGGAGTTCTTGGCATCAAGGAAGTGTATCCACAGGGACCTGGCAGCACGAA 3300
  S  F  Q  V  A  K  G  M  E  F  L  A  S  R  K  C  I  H  R  D  L  A  A  R  N

ACATTCTCCTATCGGAGAAGAATGTGGTTAAGATCTGTGACTTCGGCTTGGCCCGGGACATTTATAAAGACCCGG 3375
  I  L  L  S  E  K  N  V  V  K  I  C  D  F  G  L  A  R  D  I  Y  K  D  P  D

ATTATGTCAGAAAAGGAGATGCCCGACTCCCTTTGAAGTGGATGGCCCCGGAAACCATTTTTGACAGAGTATACA 3450
  Y  V  R  K  G  D  A  R  L  P  L  K  W  M  A  P  E  T  I  F  D  R  V  Y  T

CAATTCAGAGCGATGTGTGGTCTTTCGGTGTGTTGCTCTGGGAAATATTTTCCTTAGGTGCCTCCCCATACCCTG 3525
  I  Q  S  D  V  W  S  F  G  V  L  L  W  E  I  F  S  L  G  A  S  P  Y  P  G

GGGTCAAGATTGATGAAGAATTTTGTAGGAGATTGAAAGAAGGAACTAGAATGCGGGCTCCTGACTACACTACCC 3600
  V  K  I  D  E  E  F  C  R  R  L  K  E  G  T  R  M  R  A  P  D  Y  T  T  P

CAGAAATGTACCAGACCATGCTGGACTGCTGGCATGAGGACCCCAACCAGAGACCCTCGTTTTCAGAGTTGGTGG 3675
  E  M  Y  Q  T  M  L  D  C  W  H  E  D  P  N  Q  R  P  S  F  S  E  L  V  E

AGCATTTGGGAAACCTCCTGCAAGCAAATGCGCAGCAGGATGGCAAAGACTATATTGTTCTTCCAATGTCAGAGA 3750
  H  L  G  N  L  L  Q  A  N  A  Q  Q  D  G  K  D  Y  I  V  L  P  M  S  E  T

CACTGAGCATGGAAGAGGATTCTGGACTCTCCCTGCCTACCTCACCTGTTTCCTGTATGGAGGAAGAGGAAGTGT 3825
  L  S  M  E  E  D  S  G  L  S  L  P  T  S  P  V  S  C  M  E  E  E  E  V  C

GCGACCCCAAATTCCATTATGACAACACAGCAGGAATCAGTCATTATCTCCAGAACAGTAAGCGAAAGAGCCGGC 3900
  D  P  K  F  H  Y  D  N  T  A  G  I  S  H  Y  L  Q  N  S  K  R  K  S  R  P
```

FIG. 11-4

```
CAGTGAGTGTAAAAACATTTGAAGATATCCCATTGGAGGAACCAGAAGTAAAAGTGATCCCAGATGACAGCCAGA 3975
  V  S  V  K  T  F  E  D  I  P  L  E  E  P  E  V  K  V  I  P  D  D  S  Q  T

CAGACAGTGGGATGGTCCTTGCATCAGAAGAGCTGAAAACTCTGGAAGACAGGAACAAATTATCTCCATCTTTTG 4050
  D  S  G  M  V  L  A  S  E  E  L  K  T  L  E  D  R  N  K  L  S  P  S  F  G

GTGGAATGATGCCCAGTAAAAGCAGGGAGTCTGTGGCCTCGGAAGGCTCCAACCAGACCAGTGGCTACCAGTCTG 4125
  G  M  M  P  S  K  S  R  E  S  V  A  S  E  G  S  N  Q  T  S  G  Y  Q  S  G

GGTATCACTCAGATGACACAGACACCACCGTGTACTCCAGCGACGAGGCAGGACTTTTAAAGATGGTGGATGCTG 4200
  Y  H  S  D  D  T  D  T  T  V  Y  S  S  D  E  A  G  L  L  K  M  V  D  A  A

CAGTTCACGCTGACTCAGGGACCACACTGAGCTCACCTCCTGTTTAAATGGAAGTGGTCCTGTCCCGGCTCCGCC 4275
  V  H  A  D  S  G  T  T  L  S  S  P  P  V

CCCAACTCCTGGAAATCACGAGAGAGGTGCTGCTTAGATTTTCAAGTGTTGTTCTTTCCACCACCCGGAAGTAGC 4350
CACATTTGATTTTCATTTTTGGAGGAGGGACCTCAGACTGCAAGGAGCTTGTCCTCAGGGCATTTCCAGAGAAGA 4425
TGCCCATGACCCAAGAATGTGTTGACTCTACTCTCTTTTCCATTCATTTAAAAGTCCTATATAATGTGCCCTGCT 4500
GTGGTCTCACTACCAGTTAAAGCAAAAGACTTTCAAACACGTGGACTCTGTCCTCCAAGAAGTGGCAACGGCACC 4575
TCTGTGAAACTGGATCGAATGGGCAATGCTTTGTGTGTTGAGGATGGGTGAGATGTCCCAGGGCCGAGTCTGTCT 4650
ACCTTGGAGGCTTTGTGGAGGATGCGGGCTATGAGCCAAGTGTTAAGTGTGGGATGTGGACTGGGAGGAAGGAAG 4725
GCGCAAGCCGTCCGGAGAGCGGTTGGAGCCTGCAGATGCATTGTGCTGGCTCTGGTGGAGGTGGGCTTGTGGCCT 4800
GTCAGGAAACGCAAAGGCGGCCGGCAGGGTTTGGTTTTGGAAGGTTTGCGTGCTCTTCACAGTCGGGTTACAGGC 4875
GAGTTCCCTGTGGCGTTTCCTACTCCTAATGAGAGTTCCTTCCGGACTCTTACGTGTCTCCTGGCCTGGCCCCAG 4950
GAAGGAAATGATGCAGCTTGCTCCTTCCTCATCTCTCAGGCTGTGCCTTAATTCAGAACACCAAAAGAGAGGAAC 5025
GTCGGCAGAGGCTCCTGACGGGGCCGAAGAATTGTGAGAACAGAACAGAAACTCAGGGTTTCTGCTGGGTGGAGA 5100
CCCACGTGGCGCCCTGGTGGCAGGTCTGAGGGTTCTCTGTCAAGTGGCGGTAAAGGCTCAGGCTGGTGTTCTTCC 5175
TCTATCTCCACTCCTGTCAGGCCCCCAAGTCCTCAGTATTTTAGCTTTGTGGCTTCCTGATGGCAGAAAAATCTT 5250
AATTGGTTGGTTTGCTCTCCAGATAATCACTAGCCAGATTTCGAAATTACTTTTTAGCCGAGGTTATGATAACAT 5325
CTACTGTATCCTTTAGAATTTTAACCTATAAAACTATGTCTACTGGTTTCTGCCTGTGTGCTTATGTT        5393
```

USE OF ORGANIC COMPOUNDS FOR THE INHIBITION OF FLK-1 MEDIATED VASCULOGENESIS AND ANGIOGENESIS

This application is a continuation-in-part of U.S. application Ser. No. 08/038,596, filed Mar. 26, 1993, now abandoned which is a continuation-in-part of U.S. application Ser. No. 07/975,750, filed Nov. 13, now abandoned 1992, both of which are incorporated by reference herein in their entirety. Benefit of priority from U.S. application Ser. Nos. 08/038,596 and 07/975,750 is hereby claimed.

1. INTRODUCTION

The present invention relates to the use of proteins, peptides and organic molecules capable of modulating FLK-1 receptor signal transduction in order to inhibit or promote angiogenesis and vasculogenesis. The invention is based, in part, on the demonstration that Flk-1 tyrosine kinase receptor expression is associated with endothelial cells and the identification of vascular endothelial growth factor (VEGF) as a high affinity ligand of Flk-1. These results indicate a major role for Flk-1 in the signaling system during vasculogenesis and angiogenesis. Engineering of host cells that express Flk-1 and the uses of expressed Flk-1 to evaluate and screen for drugs and analogs of VEGF involved in Flk-1 modulation by either agonist or antagonist activities is described.

The invention also relates to the use of FLK-1 ligands, including VEGF agonists and antagonists, in the treatment of disorders, including cancer, by modulating vasculogenesis and angiogenesis.

2. BACKGROUND OF THE INVENTION

Receptor tyrosine kinases comprise a large family of transmembrane receptors for polypeptide growth factors with diverse biological activities. Their intrinsic tyrosine kinase function is activated upon ligand binding, which results in phosphorylation of the receptor and multiple cellular substrates, and subsequently in a variety of cellular responses (Ullrich A. and Schlessinger, J., 1990, Cell 61:203–212).

A receptor tyrosine kinase cDNA, designated fetal liver kinase 1 (Flk-1), was cloned from mouse cell populations enriched for hematopoietic stem and progenitor cells. The receptor was suggested to be involved in hematopoietic stem cell renewal (Matthews et al., 1991, Proc. Natl. Acad. Sci. USA 88:9026–9030). Sequence analysis of the Flk-1 clone revealed considerable homology with the c-Kit subfamily of receptor kinases and in particular to the Flt gene product. These receptors all have in common an extracellular domain containing immunoglobulin-like structures.

The formation and spreading of blood vessels, or vasculogenesis and angiogenesis, respectively, play important roles in a variety of physiological processes such as embryonic development, wound healing, organ regeneration and female reproductive processes such as follicle development in the corpus luteum during ovulation and placental growth after pregnancy. Uncontrolled angiogenesis can be pathological such as in the growth of solid tumors that rely on vascularization for growth.

Angiogenesis involves the proliferation, migration and infiltration of vascular endothelial cells, and is likely to be regulated by polypeptide growth factors. Several polypeptides with in vitro endothelial cell growth promoting activity have been identified. Examples include acidic and basic fibroblastic growth factor, vascular endothelial growth factor and placental growth factor. Although four distinct receptors for the different members of the FGF family have been characterized, none of these have as yet been reported to be expressed in blood vessels in vivo.

While the FGFs appear to be mitogens for a large number of different cell types, VEGF has recently been reported to be an endothelial cell specific mitogen (Ferrara, N. and Henzel, W. J.,1989, Biochem. Biophys. Res. Comm. 161:851–858). Recently, the fms-like tyrosine receptor, flt, was shown to have affinity for VEGF (DeVries,C. et al. , 1992, Science 255:989–991).

3. SUMMARY OF THE INVENTION

The present invention relates to the use of peptides, proteins and organic molecules capable of modulating FLK-1 receptor signal transduction in order to inhibit or promote angiogenesis and/or vasculogenesis. The present invention is based, in part, on the discovery that the Flk-1 tyrosine kinase receptor is expressed on the surface of endothelial cells and the identification of vascular endothelial growth factor (VEGF) as a high affinity ligand of Flk-1. The role of endothelial cell proliferation and migration during angiogenesis and vasculogenesis indicate an important role for Flk-1 in these processes. The invention is described by way of example for the murine Flk-1, however, the principles may be applied to other species including humans.

Pharmaceutical reagents designed to inhibit the Flk-1/ VEGF interaction may be useful in inhibition of tumor growth. VEGF and/or VEGF agonists may be used to promote wound healing. The invention relates to expression systems designed to produce Flk-1 protein and/or cell lines which express the Flk-1 receptor. Expression of soluble recombinant Flk-1 protein may be used to screen peptide libraries for molecules that inhibit the Flk-1/VEGF interaction. Engineered cell lines expressing Flk-1 on their surface may be advantageously used to screen and identify VEGF agonists and antagonists.

4. BRIEF DESCRIPTION OF THE FIGURES

FIG. 1. Comparison of the Flk-1 amino acid sequence [SEQ ID NO: 6] with related RTKs. Amino acid sequence comparison of Flk-1 with human KDR and rat TKr-C. A section of the sequence which is known for all three receptors is compared and only differences to the Flk-1 sequence are shown.

FIGS. 2A and 2B. Northern blot analysis of Flk-1 gene expression. FIG. 2A. Expression of Flk-1 RNA in day 9.5 to day 18.5 mouse embryos. Samples (10 μg) of total RNA from whole mouse embryos were analyzed in each lane. Positions of 28S and 18S ribosomal RNAs are marked.

FIG. 2B Expression of Flk-1 mRNA in postnatal day 4 and adult brain in comparison with capillary fragments from postnatal day 4 brain. 1 μg of poly (A$^+$) RNA was loaded on each lane. The 5' 2619 bp of the Flk-1 cDNA were used as a probe. Control hybridization with a GAPDH cDNA probe is shown in the lower panel.

Figure 3B:
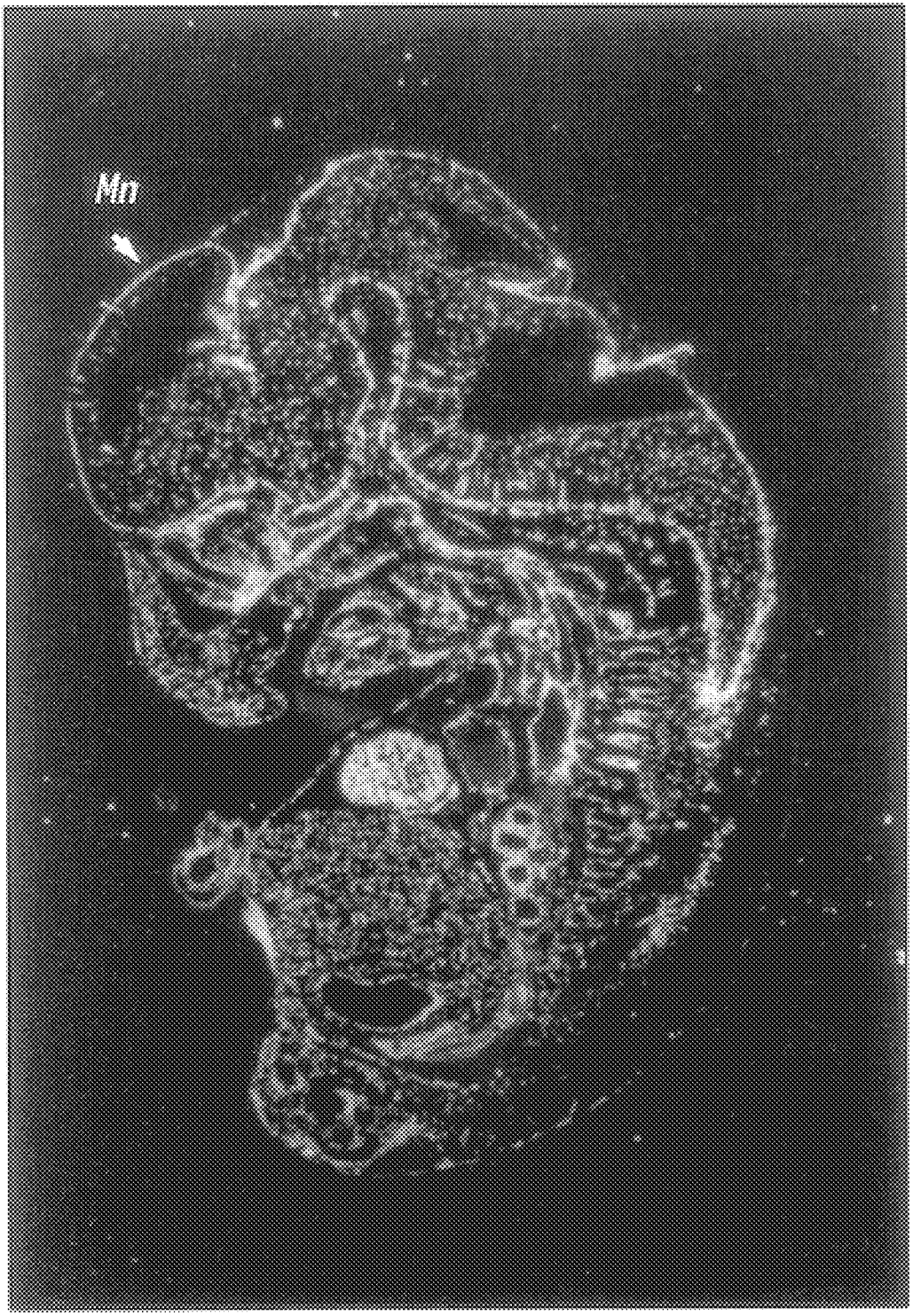
Figure 3C:

FIGS. 3A, 3B and 3C. Abundant Flk-1 gene expression in embryonic tissues. In situ hybridization analysis of Flk-1 expression in day 14.5 mouse embryo. FIG. 3A Bright field illumination of a parasagittal section through the whole embryo hybridized with a $^{35}$S-labeled antisense probe (5' 2619 bp). FIG. 3B Dark field illumination of the same section. FIG. 3C Control hybridization of an adjacent section with a sense probe. Abbreviations: Ao, aorta; At, atrium;

L, lung; Li, liver; Ma, mandible; Mn, meninges; Ms. mesencephalon; T, telencephalon; V, ventricle; Vt, vertebrae.

Figure 4C:
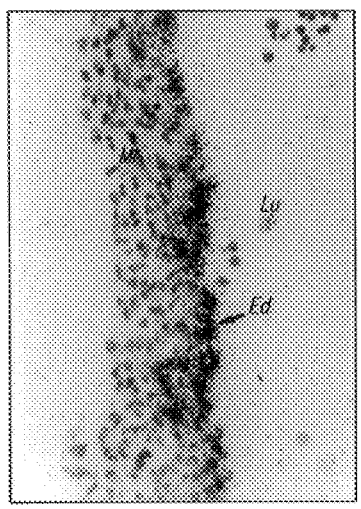
Figure 4D:
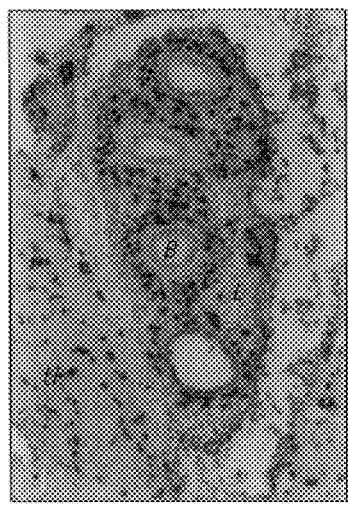
Figure 4E:

FIGS. 4A, 4B, 4C, 4D and 4E. Expression of Flk-1 RNA in embryonic organs is restricted to specific cells. Expression of Flk-1 RNA in a day 14.5 mouse embryo at higher magnification. FIG. 4A The heart region was probed with a $^{35}$S-labeled antisense probe. FIG. 4B Adjacent section hybridized with the sense probe. FIG. 4C Part of the aorta wall shown on the cellular level. The endothelial cell-layer is indicated by an arrow. FIG. 4D The lung, probed with the Flk-1 antisense probe. FIG. 4E Control hybridization of an adjacent section hybridized with the sense probe. Abbreviations: At, atrium; B, bronchus; Ed, endothelial cell layer; En, endocardium; L, lung, Li, liver; Lu, lumina of the aorta; Ml, muscular; My, myocardium.

FIGS. 5A, 5B, 5C and 5D. Flk-1 gene expression in the brain of the developing mouse. In situ hybridization analysis of Flk-1 gene expression in the brain at different developmental stages. All sections were probed with the Flk-1 antisense probe. FIG. 5A Sagittal section of the telencephalon of a day 11.5 mouse embryo. A single blood vessel expressing Flk-1 which sprouts from the meninges into the neuroectoderm, is indicated by an arrow. FIG. 5B Sagittal sections of the brain of embryo day 14.5 and FIG. 5C of postnatal day 4. Shown are regions of the mesencephalon. Branching capillaries and blood vessels expressing Flk-1 are indicated by an arrow. FIG. D Sagittal section of an adult brain; a region of the mesencephalon is shown. Cells expressing Flk-1 are indicated by an arrow. Abbreviations: M, meninges; V, ventricle;

FIG. 6A and 6B. Expression of Flk-1 in the choroid plexus of adult brain. FIG. 6A Darkfield illumination of the choroid plexus of an adult mouse brain hybridized with Flk-1 antisense probe. FIG. 6B Choroid plexus shown at a higher magnification. Arrows indicate single cells, which show strong expression of Flk-1. Abbreviations: CP, choroid plexus; E, ependyme; Ep, epithelial cells; V, ventricle.

FIGS. 7A, 7B, 7C and 7D. Flk-1 is expressed in the glomeruli of the kidney. FIG. 7A Parasagittal section of a 4-day postnatal kidney, hybridized with the Flk-1 antisense probe. Hybridization signal accumulates in the glomeruli, as indicated by arrowheads. FIG. 7B Control hybridization of an adjacent section with the sense probe. FIG. 7C Sagittal section of an adult kidney probed with Flk-1. Arrowheads indicate glomeruli. FIG. 7D Glomerulus of an adult kidney at a higher magnification. The arrows in (A) and (D) indicate cells aligned in strands in the juxtaglomerular region expressing Flk-1.

Figure 8A:
Figure 8B:
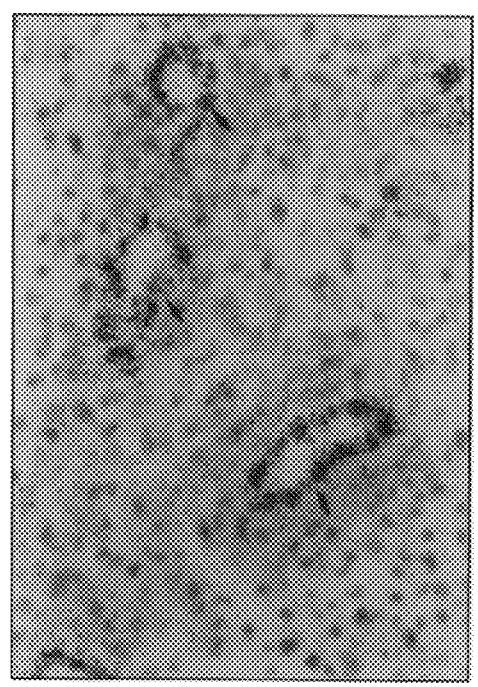
Figure 8C:
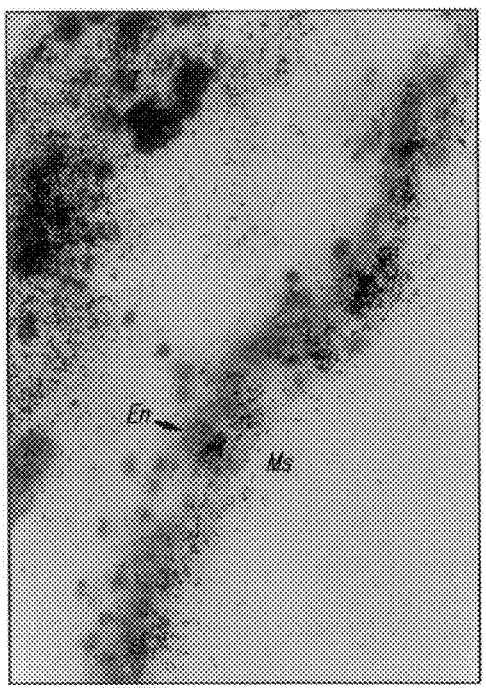
Figure 8D:
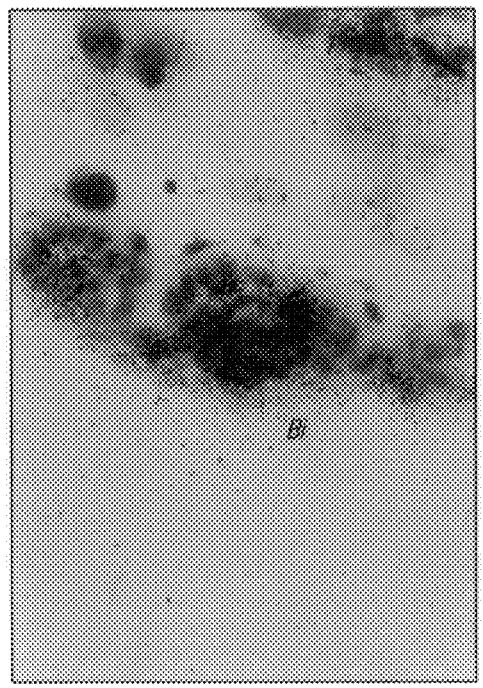

FIGS. 8A, 8b, 8C and 8D. In situ hybridization analysis of Flk-1 expression in early embryos and extraembryonic tissues. FIG. 8A Sagittal section of a day 8.5 mouse embryo in the maternal deciduum probed with Flk-1. FIG. 8B Higher magnification of the deciduum. Arrowheads indicate the endothelium of maternal blood vessels strongly expressing Flk-1 RNA. FIG. 8C High magnification of the yolk sac and the trophectoderm of a day 9.5 mouse embryo. FIG. 8D High magnification of a blood island. Abbreviations: A, allantois; Bi, blood island; Bv, maternal blood vessel; D, deciduum; En, endodermal layer of yolk sac; M, mesenchyme; Ms, mesodermal layer of yolk sac; NF, neural fold; T, trophoblast; Y, yolk sac.

Figure 9A:
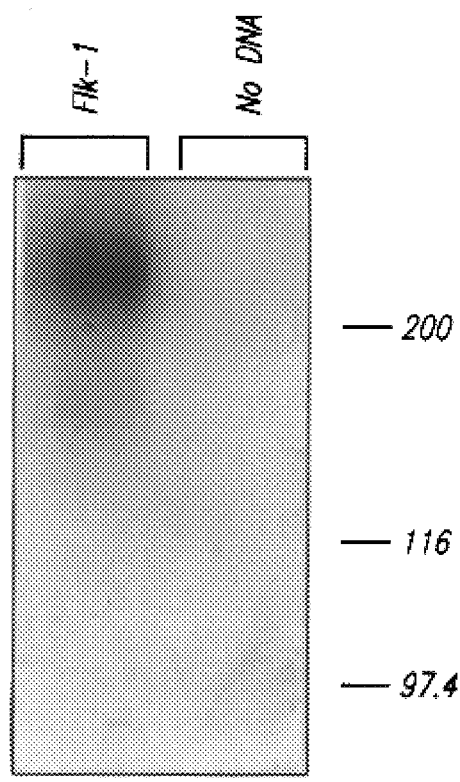

FIGS. 9A and 9B. Flk-1 is a receptor for VEGF. FIG. 9A Cross linking of $^{125}$I-VEGF to COS cells transiently expressing the Flk-1 receptor and control cells were incubated with $^{125}$I-VEGF at 4° C. overnight, then washed twice with phosphate buffered saline (PBS) and exposed to 0.5 mM of the cross linking agent DSS in PBS for 1 hour at 4° C. The cells were lysed, Flk-1 receptor immunoprecipitated, and analyzed by polyacrylamide gel electrophoresis followed by autoradiography. Molecular size markers are indicated in kilodaltons. FIG. 9B Specific binding of $^{125}$I-VEGF to COS cells expressing Flk-1. COS cells transiently expressing Flk-1 were removed from the plate and resuspended in binding medium (DMEM, 25 mM Hepes, 0.15% gelatin). Binding was performed at 15° C. for 90 minutes in a total volume of 0.5 ml containing $2\times10^5$ cells, 15,000 cpm $^{125}$I-VEGF, and the indicated concentrations of unlabeled ligand. The cells were washed twice with PBS/0.1% BSA and counted in a gamma counter.

Figure 10:
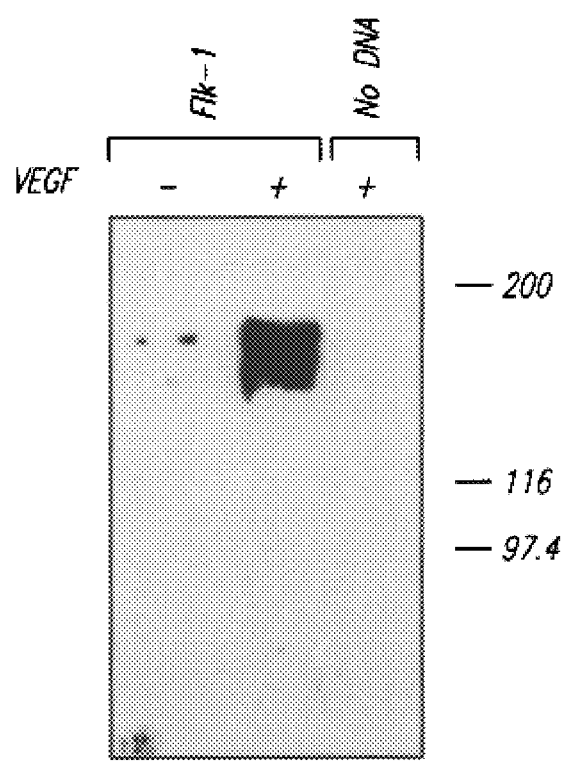

FIG. 10. VEGF-induced autophosphorylation of Flk-1. COS cells transiently expressing Flk-1 receptor and control cells were starved for 24 hours in DMEM containing 0.5% fetal calf serum and then stimulated with VEGF for 10 minutes as indicated. The cells were solubilized, Flk-1 receptor immunoprecipitated with a polyclonal antibody against its C-terminus, separated by polyacrylamide gel electrophoresis, and transferred to nitrocellulose. The blot was probed with antiphosphotyrosine antibodies (5B2). The protein bands were visualized by using a horseradish-peroxidase coupled secondary antibody and BCL™ (Amersham) detection assay.

FIGS. 11-1, 11-2, 11-3 and 11-4. Nucleotide Sequence [SEQ ID NO: 1] and amino of Murine acid Sequence [SEQ ID NO: 2] Flk-1.

Figure 12A:
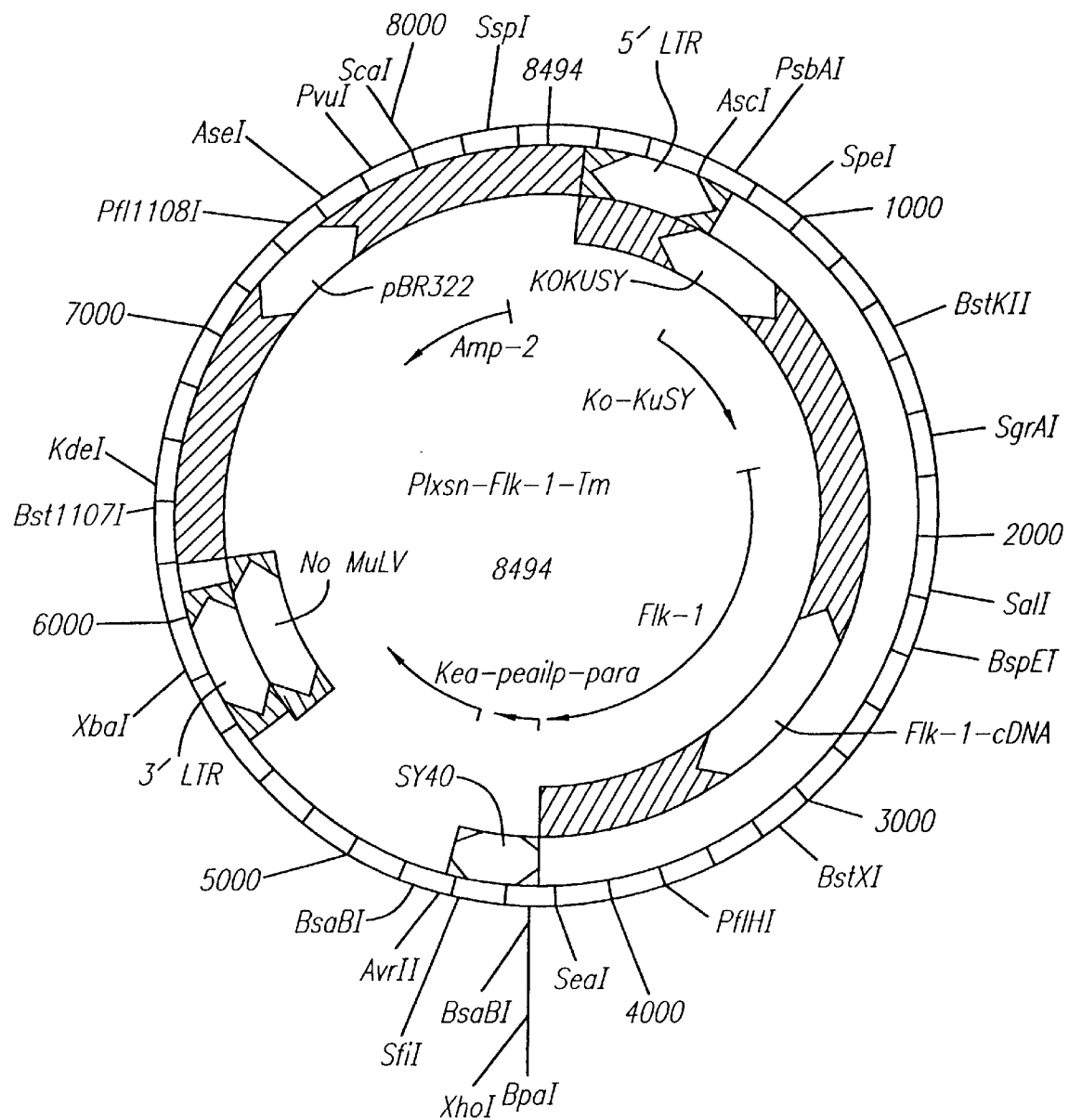
Figure 12B:
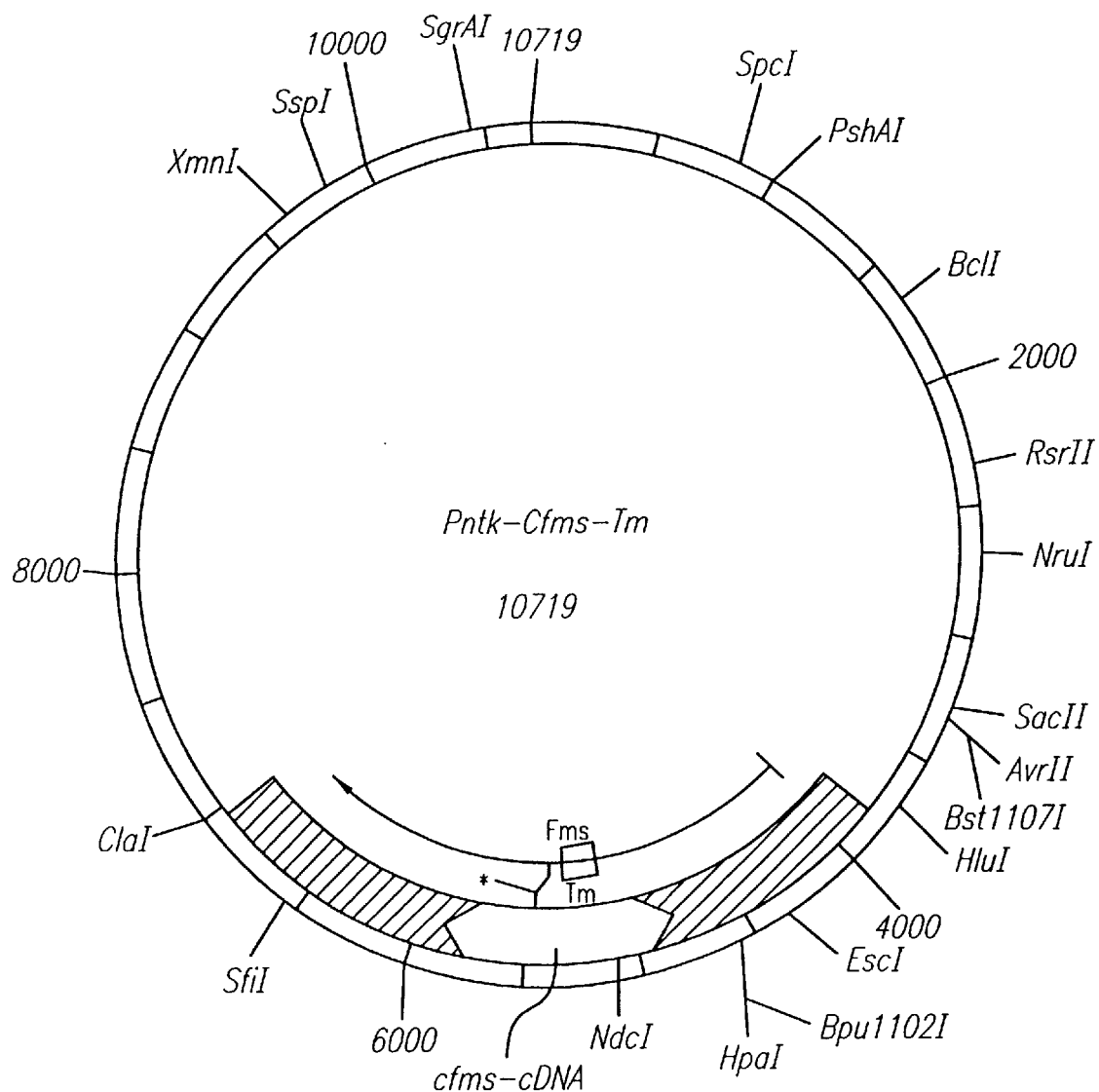

FIGS. 12A and 12B. Plasmid Maps of retroviral vector constructs. FIG. 12A. pLXSN Flk-1 TM cl.1 and pLXSN Flk-1 TM cl.3, clonal isolates of pLXSN Flk-1 TM, contain Flk-1 amino acids 1 through 806 and lack 561 C-terminal amino acids of the intracellular kinase domain. FIG. 12B. pNTK-cfms-TM contains the 541 N-terminal amino acids of the CSF-1 receptor/c-fms.

FIG. 13. Inhibition of C6 glioblastoma tumor growth by transdominant-negative inhibition of Flk-1. C6 cells were implanted either alone or coimplanted with virus-producing cells. Cell numbers are as indicated in each panel. Two different virus-producing cells lines were used: one expressing the Flk-1 TM (transdominant-negative) mutant and one expressing a transdominant-negative c-fms mutant (c-fms TM) as a control. Beginning at the time when the first tumors appeared, tumor volumes were measured every 2 to 3 days to obtain a growth curve. Each group is represented by four mice.

Figure 14:
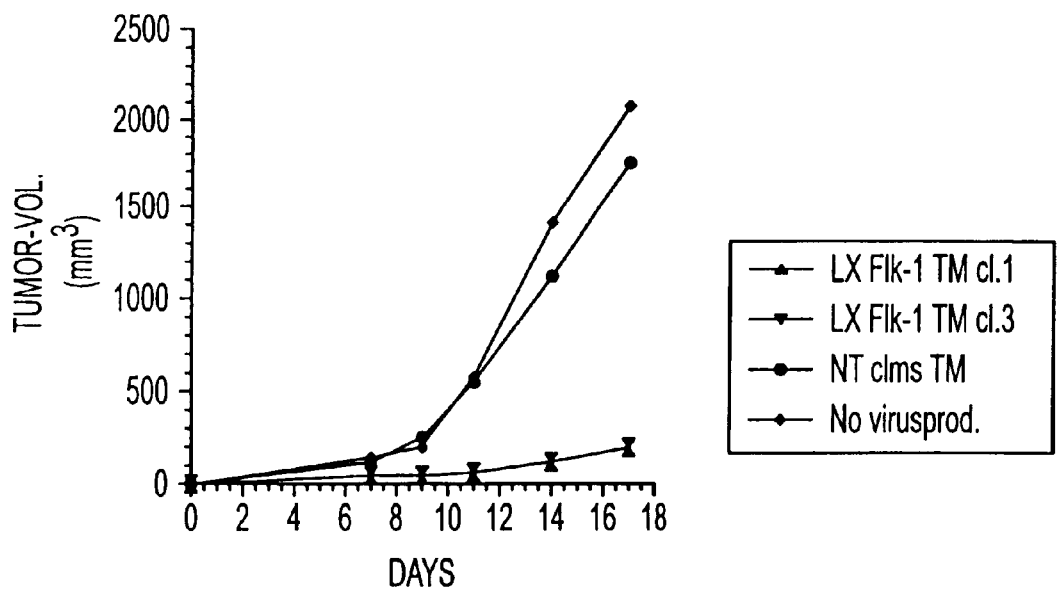

FIG. 14. A second experiment showing inhibition of C6 glioblastoma tumor growth by transdominant-negative inhibition of Flk-1. C6 cells were implanted either alone or coimplanted with virus-producing cells. Cell numbers are as indicated in each panel. Two different virus-producing cell lines were used: one expressing the Flk-1 TM (transdominant-negative) mutant and one expressing a transdominant-negative c-fms mutant (cfms TM) as a control. Beginning at the time when the first tumor appeared, tumor volumes were measured every 2 to 3 days to obtain growth curve. Each group is represented by four mice.

Figure 15:
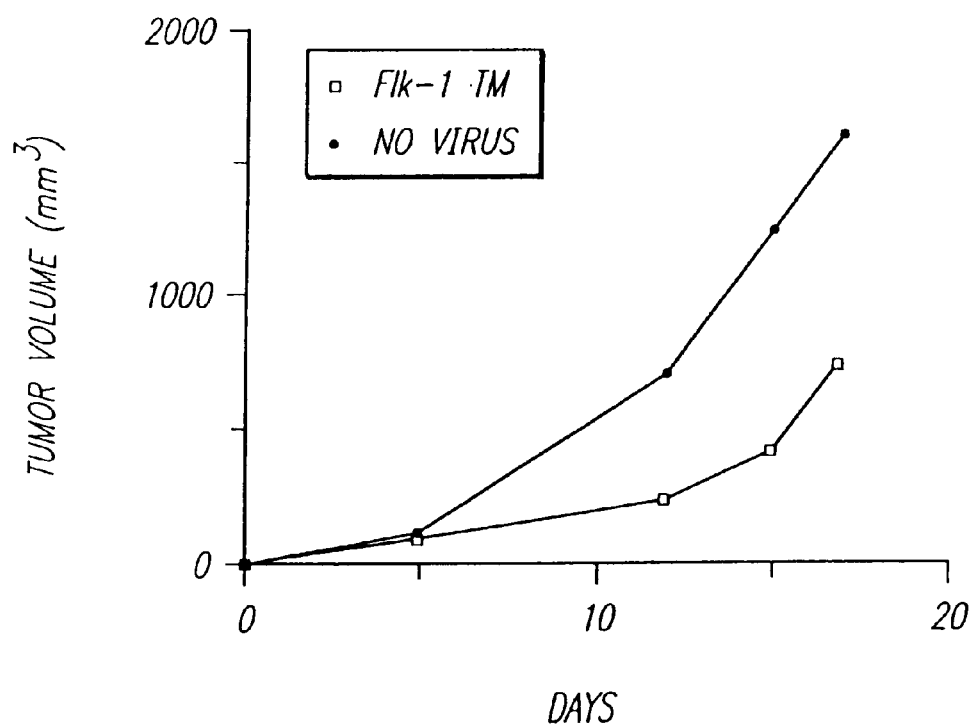

FIG. 15. Inhibition of C6 glioblastoma tumor growth by localized injection of retroviral supernatants. $1\times10^6$ cells were subcutaneously implanted in nude mice. Starting at day 5 after implantation (denoted by the arrow), the growing tumors were treated by injection of 100 µl retroviral supernatants (about 105 virus particles) into the site of tumor implantation. Tumor volumes were measured twice a week.

Figure 16A:
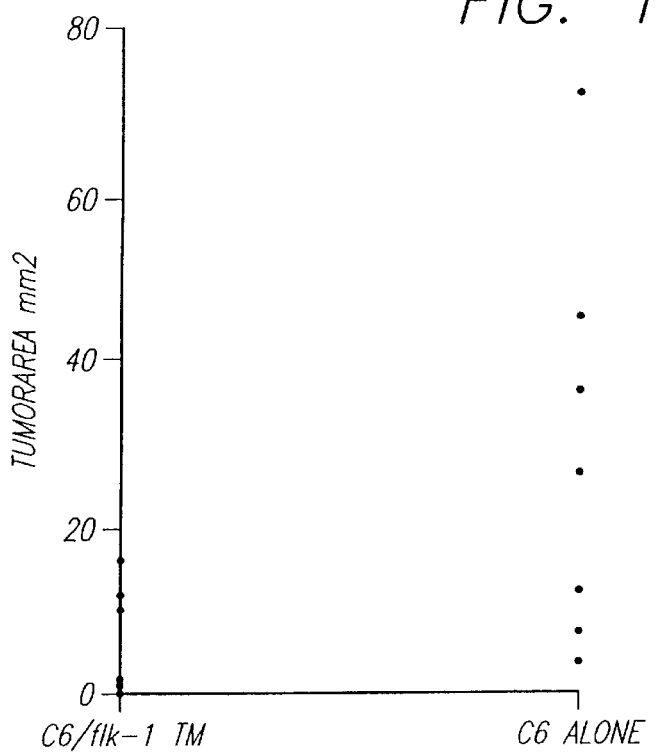
Figure 16B:
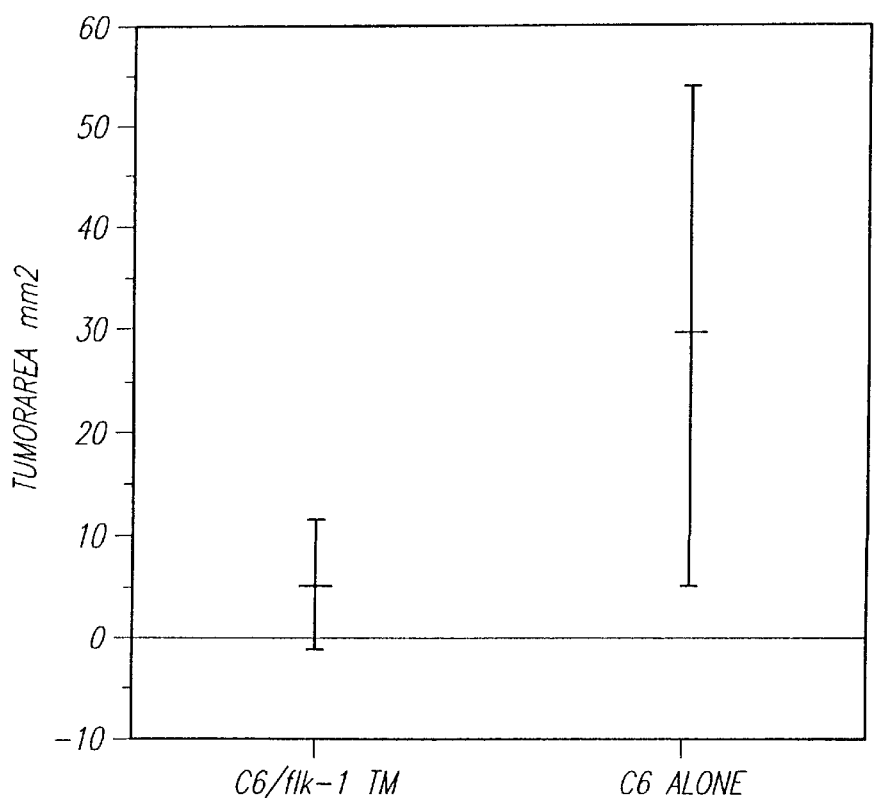

FIG. 16A and 16B. Inhibition of C6 glioblastoma tumor growth by localized injection of retroviral supernatants. C6 cells implanted intercranially in rats, either alone or co-implanted with virus producing cells expressing the Flk-1 TM (transdominant negative) mutant. Each group is represented by 8 rats. Cell numbers are as indicated in Example 6.1.13. FIG. 16A shows the distribution of tumor size in each rat. FIG. 16B shows the median tumor area for each of the two groups of rats.

Figure 17:
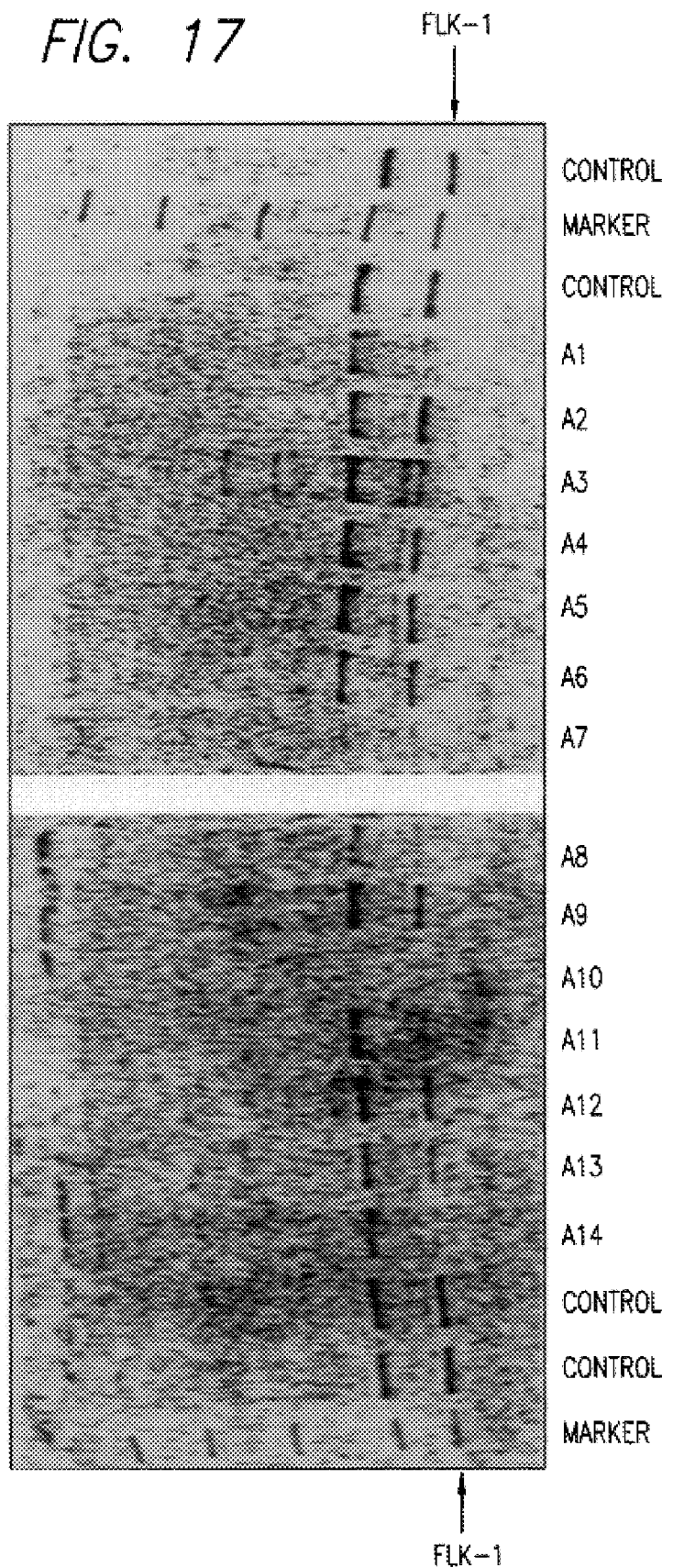

FIG. 17. Inhibition of VEGF stimulatory activity of Flk-1 . Test compounds and VEGF were co-incubated on cells expressing the Flk-1 receptor. The level of tyrosine phosphorylation was measured in a Western blot format using an antiphosphotyrosine antibody. Compound A14 completely inhibited the ability of VEGF to stimulate autophosphorylation of Flk-1. (Compounds A7, A8, and A10 were toxic to these cells resulting in cell death.)

5. DETAILED DESCRIPTION OF THE INVENTION

The present invention relates to the use of peptides, proteins, and organic molecules capable of modulating FLK-1 receptor signal transduction in order to inhibit or promote angiogenesis and/or vasculogenesis. More specifically, the invention is directed to VEGF, a natural ligand for Flk-1, as well as VEGF agonists and antagonists, anti-VEGF and anti-Flk-1 antibodies, and VEGF and Flk-1 encoding polynucleotides, all of which may find use in modulating Flk-1 signal transduction. Another aspect of the invention relates to the use of Flk-1 expressing cells to evaluate and screen proteins, peptides, and organic compounds that may be involved in Flk-1 receptor activation, regulation and/or uncoupling. Such regulators of Flk-1 may be used therapeutically. For example, agonists of VEGF may be used in processes such as wound healing; in contrast, antagonists of VEGF may be used in the treatment of tumors that rely on vascularization for growth.

The invention, is based, in part, on results from in situ-hybridization and Northern blot analyses indicating that Flk-1 is an endothelial cell specific RTK. In addition, cross-linking experiments have shown Flk-1 to be a high affinity receptor for vascular endothelial growth factor (VEGF), indicating that Flk-1 plays a crucial role in the development and differentiation of hemangioblast and in subsequent endothelial cell growth during vasculogenesis and angiogenesis.

The invention is based, also, on the discovery that expression of a transdominant-negative mutant form of the Flk-1 molecule can inhibit the biological activity of the endogenous wild type Flk-1. Experiments are described herein, in which tumor cells and cells expressing retrovirally-encoded truncated, signalling-incompetent Flk-1 receptor were injected into mice. In these experiments, the cells producing a recombinant retrovirus encoding a truncated Flk-1 receptor were either co-injected with the tumor cells or injected 5 days after injection of the tumor cells. Inhibition of vasculogenesis and growth of the injected tumor cells was observed in mice expressing the truncated form of the Flk-1 receptor. Inhibition of tumor growth observed when the truncated Flk-1 receptor was injected 5 days after injection of the tumor cells indicates that even established tumors may be suppressed by Flk-1 dominant-negative action. Thus, the invention provides a method of inhibiting the biological activity of signalling-competent Flk-1 receptors comprising introducing a signalling-incompetent Flk-1 receptor mutant into or in the vicinity of cells expressing such signalling-competent Flk-1 receptors. Accordingly, expression of transdominant negative forms of the Flk-1 molecule may be useful for treatment of diseases resulting from VEGF and/or Flk-1 mediated, abnormal proliferation of blood vessels, such as rheumatoid arthritis, retinopathies and growth of solid tumors.

As explained in the working examples, infra, the polymerase chain reaction (PCR) method was used to isolate new receptor tyrosine kinases specifically expressed in post-implantation embryos and endothelial cells. One such clone was found to encode a RTK that had almost identical sequence homology with the previously identified cDNA clone isolated from populations of cells enriched for hematopoietic cells and designated fetal liver kinase-1 (Flk-1) (Matthews et al., 1991, Proc. Natl. Acad Sci. U.S.A. 88:9026–9030) (FIGS. 11-1, 11-2, 11-3 and 11-4).

For clarity of discussion, the invention is described in the subsections below by way of example for the murine Flk-1. However, the principles may be analogously applied to clone and express the Flk-1 of other species including humans.

5.1. The Flk-1 Coding Sequence

The nucleotide coding sequence and deduced amino acid sequence of the murine Flk-1 gene is depicted in FIGS. 11-1, 11-2, 11-3 and 11-4 (SEQ. ID NO. 1 and SEQ ID NO. 2) and has recently been described in Matthews et al., 1991, Proc. Natl. Acad. Sci. U.S.A., 88:9026–9030. In accordance with the invention, the nucleotide sequence of the Flk-1 protein or its functional equivalent in mammals, including humans, can be used to generate recombinant molecules which direct the expression of Flk-1; hereinafter, this receptor will be referred to as "Flk-1", regardless of the species from which it is derived.

In a specific embodiment described herein, the murine Flk-1 gene was isolated by performing a polymerase chain reaction (PCR) using two degenerate oligonucleotide primer pools that were designed on the basis of highly conserved sequences within the kinase domain of receptor tyrosine kinases (Hanks et al., 1988,) As a template, DNA from a λgt10 cDNA library prepared from day 8.5 mouse embryos, was used. In a parallel approach, similar primers were used to amplify RTK cDNA sequences from capillary endothelial cells that had been isolated from the brains of post-natal day 4–8 mice. This is a time when brain endothelial cell proliferation is maximal. Both approaches yielded cDNA sequences encoding the recently described fetal liver RTK, Flk-1 (Matthews et al., 1991). Based on amino acid homology, this receptor is a member of the type III subclass of RTKs (Ullrich and Schlessinger) which contain immunoglobulin-like repeats in their extracellular domains (FIG. 1).

The invention also relates to Flk-1 genes isolated from other species, including humans, in which Flk-1 activity exists. Members of the Flk-1 family are defined herein as those receptors that bind VEGF or fragments of the peptide. Such receptors may demonstrate about 80% homology at the amino acid level in substantial stretches of DNA sequence. A bacteriophage cDNA library may be screened, under conditions of reduced stringency, using a radioactively labeled fragment of the mouse Flk-1 clone. Alternatively the mouse Flk-1 sequence can be used to design degenerate or fully degenerate oligonucleotide probes which can be used as PCR probes or to screen bacteriophage cDNA libraries. A polymerase chain reaction (PCR) based strategy may be used to clone human Flk-1. Two pools of degenerate oligonucleotides, corresponding to a conserved motif between the mouse Flk-1 and receptor tyrosine kinases, may be designed to serve as primers in a PCR reaction. The template for the reaction is cDNA obtained by reverse transcription of mRNA prepared from cell lines or tissue known to express human Flk-1. The PCR product may be subcloned and sequenced to insure that the amplified sequences represent the Flk-1 sequences. The PCR fragment may be used to isolate a full length Flk-1 cDNA clone by radioactively labeling the amplified fragment and screening a bacteriophage cDNA library. Alternatively, the labeled fragment may be used to screen a genomic library. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.)

Isolation of a human Flk-1 cDNA may also be achieved by construction of a cDNA library in a mammalian expression vector such as pcDNA1, that contains SV40 origin of replication sequences which permit high copy number expression of plasmids when transferred into COS cells. The expression of Flk-1 on the surface of transfected COS cells may be detected in a number of ways, including the use of a labeled ligand such as VEGF or a VEGF agonist labeled with a radiolabel, fluorescent label or an enzyme. Cells expressing the human Flk-1 may be enriched by subjecting transfected cells to a FACS (fluorescent activated cell sorter) sort.

In accordance with the invention, Flk-1 nucleotide sequences which encode Flk-1, peptide fragments of Flk-1, Flk-1 fusion proteins or functional equivalents thereof may be used to generate recombinant DNA molecules that direct the expression of Flk-1 protein or a functional equivalent thereof, in appropriate host cells. Alternatively, nucleotide sequences which hybridize to portions of the Flk-1 sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Flk-1 protein. Such DNA sequences include those which are capable of hybridizing to the murine Flk-1 sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the Flk-1 sequence, which result in a silent change thus producing a functionally equivalent Flk-1. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, analine; asparagine, glutamine; serine, threonine; phenylalanine, tyrosine. As used herein, a functionally equivalent Flk-1 refers to a receptor which binds to VEGF or fragments, but not necessarily with the same binding affinity of its counterpart native Flk-1 .

The DNA sequences of the invention may be engineered in order to alter the Flk-1 coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the Flk-1 coding sequence to eliminate any N-linked glycosylation site.

In another embodiment of the invention, the Flk-1 or a modified Flk-1 sequence may be ligated to a heterologous sequence to encode a fusion protein. For example, for screening of peptide libraries it may be useful to encode a chimeric Flk-1 protein expressing a heterologous epitope that is recognized by a commercially available antibody. A fusion protein may also be engineered to contain a cleavage site located between the Flk-1 sequence and the heterologous protein sequence, so that the Flk-1 can be cleaved away from the heterologous moiety.

In an alternate embodiment of the invention, the coding sequence of Flk-1 could be synthesized in whole or in part, using chemical methods well known in the art. See, for example, Caruthers, et al., 1980, Nuc. Acids Res. Symp. Ser. 7:215–233; Crea and Horn, 180, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize the Flk-1 amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

5.2. Expression of Flk-1 Receptor and Generation of Cell Lines That Express Flk-1

In order to express a biologically active Flk-1, the nucleotide sequence coding for Flk-1, or a functional equivalent as described in Section 5.1 supra, is inserted into an appropriate expression vector, i.e., a vector which contains the necessary elements for the transcription and translation of the inserted coding sequence. The Flk-1 gene products as well as host cells or cell lines transfected or transformed with recombinant Flk-1 expression vectors can be used for a variety of purposes. These include but are not limited to generating antibodies (i.e., monoclonal or polyclonal) that bind to the receptor, including those that competitively inhibit binding of VEGF and "neutralize" activity of Flk-1 and the screening and selection of VEGF analogs or drugs that act via the Flk-1 receptor; etc.

5.2.1. Expression Systems

Methods which are well known to those skilled in the art can be used to construct expression vectors containing the Flk-1 coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the Flk-1 coding sequence. These include but are not limited to microorganisms such as bacteria transformed with recombinant bacteriophage DNA, plasmid DNA or cosmid DNA expression vectors containing the Flk-1 coding sequence; yeast transformed with recombinant yeast expression vectors containing the Flk-1 coding sequence; insect cell systems infected with recombinant virus expression vectors (e.g., baculovirus) containing the Flk-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Flk-1 coding sequence; or animal cell systems infected with recombinant virus expression vectors (e.g., adenovirus, vaccinia virus) including cell lines engineered to contain multiple copies of the Flk-1 DNA either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the Flk-1 DNA SV40-, BPV- and EBV-based vectors may be used with an appropriate selectable marker.

In bacterial systems a number of expression vectors may be advantageously selected depending upon the use intended for the Flk-1 expressed. For example, when large quantities of Flk-1 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the Flk-1 coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the Flk-1 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express Flk-1 is an insect system. In one such system, *Autographa californica* nuclear polyhidrosis virus (AcNPV) is used as a vector to express foreign genes. The virus grows in *Spodoptera frugiperda* cells. The Flk-1 coding sequence may be cloned into non-essential regions (for example the polyhedrin gene) of the virus and placed under control of an AcNPV promoter (for example the polyhedrin promoter). Successful insertion of the Flk-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (Eq., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the Flk-1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Flk-1 in infected hosts. (E.g., See Logan & Shenk, 1984, Proc. Natl. Acad. Sci. (USA) 81:3655–3659). Alternatively, the vaccinia 7.5K promoter may be used. (See, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted Flk-1 coding sequences. These signals include the ATG initiation codon and adjacent sequences. In cases where the entire Flk-1 gene, including its own initiation codon and adjacent sequences, is inserted into the appropriate expression vector, no additional translational control signals may be needed. However, in cases where only a portion of the Flk-1 coding sequence is inserted, exogenous translational control signals, including the ATG initiation codon, must be provided. Furthermore, the initiation codon must be in phase with the reading frame of the Flk-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the Flk-1 may be engineered. Rather than using expression vectors which contain viral origins of replication, host cells can be transformed with the Flk-1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Flk-1 on the cell surface, and which respond to VEGF mediated signal transduction. Such engineered cell lines are particularly useful in screening VEGF analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.2. Identification of Transfectants or Transformants That Express the Flk-1

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of Flk-1 mRNA transcripts in the host cell; and (d) detection of the gene product as measured by immunoassay or by its biological activity.

In the first approach, the presence of the Flk-1 coding sequence inserted in the expression vector can be detected by DNA-DNA or DNA-RNA hybridization using probes comprising nucleotide sequences that are homologous to the Flk-1 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the Flk-1 coding sequence is inserted within a marker gene sequence of the vector, recombinants containing the Flk-1 coding sequence can be identified by the absence of the marker gene function. Alternatively, a marker gene can be placed in tandem with the Flk-1 sequence under the control of the same or different promoter used to control the expression of the Flk-1 coding sequence. Expression of the marker in response to induction or selection indicates expression of the Flk-1 coding sequence.

In the third approach, transcriptional activity for the Flk-1 coding region can be assessed by hybridization assays. For example, RNA can be isolated and analyzed by Northern blot using a probe homologous to the Flk-1 coding sequence or particular portions thereof. Alternatively, total nucleic acids of the host cell may be extracted and assayed for hybridization to such probes.

In the fourth approach, the expression of the Flk-1 protein product can be assessed immunologically, for example by Western blots, immunoassays such as radioimmunoprecipitation, enzyme-linked immunoassays and the like. The ultimate test of the success of the expression system, however, involves the detection of the biologically active Flk-1 gene product. A number of assays can be used to detect receptor activity including but not limited to VEGF binding assays; and VEGF biological assays using engineered cell lines as the test substrate.

5.3. Uses of the Flk-1 Receptor and Engineered Cell Lines

Angiogenesis, the growth of new blood capillary vessels, is required for a number of physiological processes ranging from wound healing, tissue and organ regeneration, placental formation after pregnancy and embryonic development. Abnormal proliferation of blood vessels is an important component of a variety of diseases such as rheumatoid arthritis, retinopathies, and psoriasis. Angiogenesis is also an important factor in the growth and metastatic activity of solid tumors that rely on vascularization. Therefore, inhibitors of angiogenesis may be used therapeutically for the treatment of diseases resulting from or accompanied by abnormal growth of blood vessels and for treatments of malignancies involving growth and spread of solid tumors.

In an embodiment of the invention the Flk-1 receptor and/or cell lines that express the Flk-1 receptor may be used to screen for antibodies, peptides, organic molecules or other ligands that act as agonists or antagonists of angiogenesis or vasculogenesis mediated by the Flk-1 receptor. For example, anti-Flk-1 antibodies capable of neutralizing the activity of VEGF, may be used to inhibit Flk-1 function. Additionally, anti-Flk-1 antibodies which mimic VEGF activity may be selected for uses in wound healing. Alternatively, screening of peptide libraries or organic compounds with recombinantly expressed soluble Flk-1 protein or cell lines expressing Flk-1 protein may be useful for identification of therapeutic molecules that function by inhibiting the biological activity of Flk-1.

In an embodiment of the invention, engineered cell lines which express the entire Flk-1 coding region or its ligand binding domain may be utilized to screen and identify VEGF antagonists as well as agonists. Synthetic compounds, natural products, and other sources of potentially biologically active materials can be screened in a number of ways. The ability of a test compound to inhibit binding of VEGF to Flk-1 may be measured using standard receptor binding techniques, such as those described in section 6.1.9., or using any of the compound screening assays described in Section 5.3.2. and 6.1.14. The ability of agents to prevent or mimic, the effect of VEGF binding on signal transduction responses on Flk-1 expressing cells may be measured. For example, responses such as activation of Flk-1 kinase activity, modulation of second messenger production or changes in cellular metabolism may be monitored. These assays may be performed using conventional techniques developed for these purposes.

The ability of a test compound to modulate signal transduction through the VEGF-Flk-1 system may also be measured in vivo, in models such as those described in Section 6.1.12. and 6.1.13. The ability of agents to prevent the effect of VEGF binding on signal transduction responses of Flk-1 expressing cells may be measured. For example, responses such as inhibition of angiogenesis, inhibition of the development of solid tumors, or reduction of solid tumor size may be monitored.

5.3.1. Screening of Peptide Library with Flk-1 Protein or Engineered Cell Lines

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that act to inhibit the biological activity of receptors through their interactions with the given receptor.

Identification of molecules that are able to bind to the Flk-1 may be accomplished by screening a peptide library with recombinant soluble Flk-1 protein. Methods for expression and purification of Flk-1 are described in Section 5.2.1 and may be used to express recombinant full length Flk-1 or fragments of Flk-1 depending on the functional domains of interest. For example, the kinase and extracellular ligand binding domains of Flk-1 may be separately expressed and used to screen peptide libraries.

To identify and isolate the peptide/solid phase support that interacts and forms a complex with Flk-1, it is necessary to label or "tag" the Flk-1 molecule. The Flk-1 protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to Flk-1, may be performed using techniques that are routine in the art. Alternatively, Flk-1 expression vectors may be engineered to express a chimeric Flk-1 protein containing an epitope for which a commercially available antibody exist. The epitope specific antibody may be tagged using methods well known in the art including labeling with enzymes, fluorescent dyes or colored or magnetic beads.

The "tagged" Flk-1 conjugate is incubated with the random peptide library for 30 minutes to one hour at 22° C. to allow complex formation between Flk-1 and peptide species within the library. The library is then washed to remove any unbound Flk-1 protein. If Flk-1 has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4, 4"-diamnobenzidine (DAB), respectively. After incubating for several minutes, the peptide/solid phase-Flk-1 complex changes color, and can be easily identified and isolated physically under a dissecting microscope with a micromanipulator. If a fluorescent tagged Flk-1 molecule has been used, complexes may be isolated by fluorescent activated sorting. If a chimeric Flk-1 protein expressing a heterologous epitope has been used, detection of the peptide/Flk-1 complex may be accomplished by using a labeled epitope specific antibody. Once isolated, the identity of the peptide attached to the solid phase support may be determined by peptide sequencing.

In addition to using soluble Flk-1 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing Flk-1 are described in Sections 5.2.1. and 5.2.2. The cells used in this technique may be either live or fixed cells. The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

5.3.2. Screening of Organic Compounds with Flk-1 Protein or Engineered Cell Lines Cell lines that express Flk-1 may be used to screen for molecules that modulate Flk-1 receptor activity or signal transduction. Such molecules may include small organic or inorganic compounds, or other molecules that modulate Flk-1 receptor activity or that promote or prevent the formation of Flk-1/VEGF complex. Synthetic compounds, natural products, and other sources of potentially biologically active materials can be screened in a number of ways.

The ability of a test molecule to interfere with VEGF-Flk-1 binding and/or Flk-1 receptor signal may be measured using standard biochemical techniques. Other responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Ligand binding to its cellular receptor may, via signal transduction pathways, affect a variety of cellular processes. Cellular processes under the control of the Flk-1/VEGF signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Various embodiments are described below for screening, identification and evaluation of compounds that interact with the Flk-1 receptor, which compounds may affect various cellular processes under the control of the Flk/VEGF receptor signalling pathway.

The present invention includes a method for identifying a compound which is capable of modulating signal transduction, comprising:

(a) contacting the compound with Flk-1, or a functional derivative thereof, in pure or semi-pure form, in a membrane preparation, or in a whole live or fixed cell;

(b) incubating the mixture of step (a) in the presence of VEGF, for an interval sufficient for the compound to stimulate or inhibit the signal transduction;

(c) measuring the signal transduction;

(d) comparing the signal transduction activity to that of Flk-1, incubated without the compound, thereby determining whether the compound stimulates or inhibits signal transduction.

Flk-1, or functional derivatives thereof, useful in identifying compounds capable of modulating signal transduction may have, for example, amino acid deletions and/or insertions and/or substitutions as long as they retain significant signal transducing capacity. A functional derivative of Flk-1 may be prepared from a naturally occurring or recombinantly expressed Flk-1 by proteolytic cleavage followed by conventional purification procedures known to those skilled in the art. Alternatively, the functional derivative may be produced by recombinant DNA technology by expressing parts of Flk-1 which include the functional domain in suitable cells. Functional derivatives may also be chemically synthesized. Cells expressing Flk-1 may be used as a source of Flk-1, crude or purified, or in a membrane preparation, for testing in these assays. Alternatively, whole live or fixed cells may be used directly in those assays.

Flk-1 signal transduction activity may be measured by standard biochemical techniques or by monitoring the cellular processes controlled by the signal. To assess modulation of kinase activity, the test molecule is added to a reaction mixture containing Flk-1 and a substrate test. To assess modulation of kinase activity of the Flk-1 receptor, the test molecule is added to a reaction mixture containing the Flk-1 receptor. The kinase reaction is then initiated with the addition of VEGF and ATP. An immunoassay is performed on the kinase reaction to detect the presence or absence of the phosphorylated tyrosine residues on the substrate or to detect phosphorylated tyrosine residues on autophosphorylated Flk-1, and results are compared to those obtained for controls i.e., reaction mixtures not exposed to the test molecule. The immunoassay used to detect the phosphorylated substrate in the cell lysate or the in vitro reaction mixture may be carried out with an anti-phosphotyrosine antibody.

The invention further provides for a method of screening compounds that, upon interacting with Flk-1, elicit or trigger a signal mimicking the action of VEGF binding to the Flk-1 receptor. Signal transduction is mimicked if the cellular processes under the control of the signalling pathway are affected in a way similar to that caused by ligand binding. Such compounds may be naturally occurring or synthetically produced molecules that activate the Flk-1 receptor.

The invention also includes a method whereby a molecule capable of binding to Flk-1 in a chemical or biological preparation may be identified comprising:

(a) immobilizing Flk-1, or functional fragments thereof, to a solid phase matrix;

(b) contacting the chemical or biological preparation with the solid phase matrix produced in step (a), for an interval sufficient to allow the compound to bind;

(c) washing away any unbound material from the solid phase matrix;

(d) detecting the presence of the compound bound to the solid phase, thereby identifying the compound.

The above method may further include the step of:

(e) eluting the bound compound from the solid phase matrix, thereby isolating the compound.

The term "compound capable of binding to Flk-1" refers to a naturally occurring or synthetically produced molecule which interacts with Flk-1. Such a compound may directly or indirectly modulate Flk-1 signal transduction and may include molecules that are natively associated with the intracellular domain of Flk-1 inside a cell. Examples of such compounds are (i) a natural substrate of Flk-1; (ii) a naturally occurring molecule which is part of the signalling complex; and/or a naturally occurring signalling molecule produced by other cell types.

5.3.3. Antibody Production and Screening

Various procedures known in the art may be used for the production of antibodies to epitopes of the recombinantly produced Flk-1 receptor. Such antibodies include but are not limited to polyclonal, monoclonal, chimeric, single chain, Fab fragments and fragments produced by an Fab expression library. Neutralizing antibodies i.e., those which compete for the VEGF binding site of the receptor are especially preferred for diagnostics and therapeutics.

Monoclonal antibodies that bind Flk-1 may be radioactively labeled allowing one to follow their location and distribution in the body after injection. Radioactivity tagged antibodies may be used as a non-invasive diagnostic tool for imaging de novo vascularization associated with a number of diseases including rheumatoid arthritis, macular degeneration, and formation of tumors and metastases.

Immunotoxins may also be designed which target cytotoxic agents to specific sites in the body. For example, high affinity Flk-1 specific monoclonal antibodies may be covalently complexed to bacterial or plant toxins, such as diptheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Flk-1 expressing endothelial cells.

For the production of antibodies, various host animals may be immunized by injection with the Flk-1 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to Flk-1 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce Flk-1-specific single chain antibodies.

Antibody fragments which contain specific binding sites of Flk-1 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Flk-1.

5.4. Uses of Flk-1 Coding Sequence

The Flk-1 coding sequence may be used for diagnostic purposes for detection of Flk-1 expression. Included in the scope of the invention are oligoribonucleotide sequences, that include antisense RNA and DNA molecules and ribozymes that function to inhibit translation of Flk-1. In addition, mutated forms of Flk-1, having a dominant negative effect, may be expressed in targeted cell populations to inhibit the activity of endogenously expressed wild-type Flk-1.

5.4.1. Use of Flk-1 Coding Sequence in Diagnostics and Therapeutics

The Flk-1 DNA may have a number of uses for the diagnosis of diseases resulting from aberrant expression of Flk-1. For example, the Flk-1 DNA sequence may be used in hybridization assays of biopsies or autopsies to diagnose abnormalities of Flk-1 expression; e.g., Southern or Northern analysis, including in situ hybridization assays.

The Flk-1 cDNA may be used as a probe to detect the expression of the Flk-1 mRNA. In a specific example described herein, the expression of Flk-1 mRNA in mouse embryos of different developmental stages was analyzed. Northern blot analysis indicated abundant expression of a major 5.5 kb mRNA between day 9.5 and day 18.5, with apparent decline towards the end of gestation (FIG. 2A). In post-natal day 4–8 brain capillaries Flk-1 mRNA was found to be highly enriched compared to total brain RNA (FIG. 2B), suggesting a role for Flk-1 in endothelial cell proliferation.

To obtain more detailed information about the expression of Flk-1 during embryonic development and during the early stages of vascular development in situ hybridization experiments were performed as described in Section 6.1.4. In situ hybridizations demonstrated that Flk-1 expression in vivo during embryonic mouse development is largely restricted to endothelial cells and their precursors (FIGS. 3A, 3B, 3C. and FIGS. 4A, 4B, 4C, 4D and 4E). Flk-1 is expressed in endothelial cells during physiological processes that are characterized by endothelial cell proliferation and the temporal and spatial expression pattern found in the embryonic brain correlate precisely with the development of the neural vascular system as described by Bar (1980). Vascular sprouts originating in the perineural plexus grow radially into the neuroectoderm and branch there and these sprouts were found to express high amounts of Flk-1 mRNA (FIGS. 5A, 5B, 5C and 5D). In the early postnatal stages, endothelial cell proliferation is still evident and Flk-1 is expressed, whereas in the adult organism, after completion of the vascularization process, the decline in endothelial cell proliferation parallels a decrease in Flk-1 expression.

Also within the scope of the invention are oligoribonucleotide sequences, that include anti-sense RNA and DNA molecules and ribozymes that function to inhibit the translation of Flk-1 mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the Flk-1 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of Flk-1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.4.2. Use of Dominant Negative Flk-1 Mutants in Gene Therapy

Receptor dimerization induced by ligands, is thought to provide an allosteric regulatory signal that functions to couple ligand binding to stimulation of kinase activity. Defective receptors can function as dominant negative mutations by suppressing the activation and response of normal receptors through formation of heterodimers with wild type receptors wherein such heterodimers are signalling incompetent. Defective receptors can be engineered into recombinant viral vectors and used in gene therapy in individuals that inappropriately express Flk-1.

The capability of Flk-1 TM to form signalling incompetent heterodimers with the 180 kD wild type Flk-1 is demonstrated in Section 6.1.12. The dominant-negative potential of Flk-1 TM used in gene therapy may be measured by examining its influence on the Flk-1/VEGF mitogenic response or by measurement of suppression of Flk-1 transforming activity.

In an embodiment of the invention, mutant forms of the Flk-1 molecule having a dominant negative effect may be identified by expression in selected cells. Deletion or missense mutants of Flk-1 that retain the ability to form dimers with wild type Flk-1 protein but cannot function in signal transduction may be used to inhibit the biological activity of the endogenous wild type Flk-1. For example, the cytoplasmic kinase domain of Flk-1 may be deleted resulting in a truncated Flk-1 molecule that is still able to undergo dimerization with endogenous wild type receptors but unable to transduce a signal.

Abnormal proliferation of blood vessels is an important component of a variety of pathogenic disorders such as rheumatoid arthritis, retinopathies and psoriasis. Uncontrolled angiogenesis is also an important factor in the growth and metastases of solid tumors. Recombinant viruses may be engineered to express dominant negative forms of Flk-1 which may be used to inhibit the activity of the wild type endogenous Flk-1. These viruses may be used therapeutically for treatment of diseases resulting from aberrant expression or activity of Flk-1.

Expression vectors derived from viruses such as retroviruses, vaccinia virus, adeno-associated virus, herpes viruses, or bovine papilloma virus, may be used for delivery of recombinant Flk-1 into the targeted cell population. Methods which are well known to those skilled in the art can be used to construct recombinant viral vectors containing Flk-1 coding sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant Flk-1 molecules can be reconstituted into liposomes for delivery to target cells.

In a specific embodiment of the invention, a deletion mutant of the Flk-1 receptor was engineered into a recombinant retroviral vector. Two clonal isolates of Flk-1 TM, designated pLXSN Flk-1 TM cl.1 and pLXSN Flk-1 TM cl.3, contain a truncated Flk-1 receptor containing Flk-1 amino acids 1 through 806 [SEQ ID NO: 5] but lacking the 561 COOH-terminal amino acids of the intracellular kinase domain. These isolates retain transmembrane domain sequences and 23 residues of the cytoplasmic domain. To obtain virus producing cell lines, PA37 cells were transfected with the recombinant vectors and, subsequently, conditioned media containing virus were used to infect GPE cells.

To test whether expression of signaling-defective mutants inhibits endogenous Flk-1 receptor activity, C6 rat gliobastoma cells (tumor cells) and mouse cells producing the recombinant retroviruses were mixed and injected subcutaneously into nude mice. Normally, injection of tumor cells into nude mice would result in proliferation of the tumor cells and vascularization of the resulting tumor mass. Since Flk-1 is believed to be essential for formation of blood vessels, blocking Flk-1 activity by expression of a truncated receptor, might function to inhibit vascularization of the developing tumor and, thereby, inhibit its growth. As illustrated in FIGS. 13 and 14, coinjection of virus producing cells, expressing a truncated Flk-1 receptor, significantly inhibits the growth of the tumor as compared to controls receiving only tumor cells.

As illustrated in FIG. 15, a similar inhibitory effect on C6 glioma tumor growth was also observed when truncated Flk-1 receptor virus particle-containing producer cells were injected five days after implantation of $10^6$ tumor cells, indicating that even established tumors may be suppressed by Flk-1 dominant-negative action. For glioblastoma, a tumor with generally poor prognosis and resistance to all available therapies, retrovirus-mediated gene therapy may be advantageous, since non-mitotic brain tissues such as neurons, glia and quiescent endothelial cells would not be infected. Glioblastoma multiforme is the most common and most malignant tumor of astrocytic origin in human adults and accounts for more than half of all primary brain tumors (See, for example, Cecil Textbook of Medicine, Wyngaarden, Smith, Bennett (eds) W B Saunders, p.2220 (1992).

5.5. Use of Flk-1 Receptor or Ligands

Receptor/ligand interaction between Flk-1 and VEGF is believed to play an important role in the signalling system during vascularization and angiogenesis. Abnormal proliferation of blood vessels is an important component of a number of diseases.

Expression of Flk-1 RNA correlates with the development of the brain and with endothelial cell proliferation suggesting that Flk-1 might be a receptor involved in mediation of signaling events in the neural vascularization process. VEGF has been shown to be a mitogenic growth factor known to act exclusively on endothelial cells (Ferrara, N. and Henzel, W. J., 1989, Biochem. Biophys. Res. Comm. 161:851–858). Cross-linking and ligand binding experiments were performed, as described in Sections 6.1.9 and 6.1.10 respectively, to determine whether VEGF is a ligand for Flk-1. The results indicate that Flk-1 is an authentic high affinity VEGF receptor (FIGS. 9A and 9B).

In one embodiment of the invention, ligands for Flk-1, the Flk-1 receptor itself, or a fragment containing its VEGF binding site, could be administered in vivo to modulate angiogenesis and/or vasculogenesis. For example, administration of the Flk-1 receptor or a fragment containing the VEGF binding site, could competitively bind to VEGF and inhibit its interaction with the native Flk-1 receptor in vivo to inhibit angiogenesis and/or vasculogenesis. Alternatively, ligands for Flk-1, including anti-Flk-1 antibodies or fragments thereof, may be used to modulate angiogenesis and/or vasculogenesis. Agonists of VEGF activity may be used to promote wound healing whereas antagonists of VEGF activity may be used to inhibit tumor growth.

The particular peptides, proteins, organic compounds or antibodies that modulate Flk-1 receptor signal transduction can be administered to a patient either by itself, or in pharmaceutical compositions where it is mixed with suitable carriers or excipient(s).

Depending on the specific conditions being treated, these agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, or, in the case of solid tumors, directly injected into a solid tumor. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Compositions comprising a compound of the invention formulated in a compatible pharmaceutical carrier may be prepared, placed in an appropriate container, and labelled for treatment of an indicated condition. Suitable conditions indicated on the label may include treatment of a tumor, such as a glioma or glioblastoma; and inhibition of angiogenesis.

A preferred pharmaceutical carrier for hydrophobic compounds of the invention is a cosolvent system comprising benzyl alcohol, a nonpolar surfactant, a water-miscible organic polymer, and an aqueous phase. A preferred cosolvent system is the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as DMSO also may be employed, although usually at the cost of greater toxicity.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the Flk-1 receptor modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTP activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 pl).

Dosage amount and interval may be adjusted individually to provide plasma levels of the active moiety which are sufficient to maintain the Flk-1 receptor-inhibitory effects. Usual patient dosages for systemic administration range from 1–2000 mg/day, commonly from 1–250 mg/day, and typically from 10–150 mg/day. Stated in terms of patient body weight, usual dosages range from 0.02–25 mg/kg/day, commonly from 0.02–3 mg/kg/day, typically from 0.2–1.5 mg/kg/day. Stated in terms of patient body surface areas, usual dosages range from 0.5–1200 mg/m$^2$/day, commonly from 0.5–150 mg/m$^2$/day, typically from 5–100 mg/m$^2$/day.

Dosage amount and interval may be adjusted individually to provide plasma levels of the active moiety which are sufficient to maintain the Flk-1 receptor-inhibitory effects. Usual average plasma levels should be maintained within 50–5000 µg/ml, commonly 50–1000 µg/ml, and typically 100–500 µg/ml Alternately, one may administer the compound in a local rather than systemic manner, for example, via injection of the compound directly into a tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

6. Example: Cloning and Expression Pattern of Flk-1, a High Affinity Receptor for VEGF The subsection below describes the cloning and characterization of the Flk-1 cDNA clone. Northern blot and in situ hybridization analyses indicate that Flk-1 is expressed in endothelial cells. Cross-linking and ligand binding experiments further indicate that Flk-1 is a high affinity receptor for VEGF.

6.1. Materials and Methods 6.1.1. cDNA Cloning of Flk-1

DNA extracted from λgt10 cDNA library of day 8.5 mouse embryos (Fahrner et al., 1987, EMBO. J. 6:1497–1508) was used as template for polymerase chain reaction (PCR; Saiki, R. K. et al., 1985 Science 230:1350–1354). In an independent approach cDNA of capillary endothelial cells that had been isolated from the brain of postnatal day 4–8 mice was used for amplification (Risau, W., 1990 In: development of the Vascular System. Issues Biomed. Basel Karger 58–68 and Schnürch et al., unpublished) Degenerated primers were designed on the basis of high amino acid homologies within the kinase domain shared by all RTKs (Wilks, A. F., 1989, Proc. Natl. Acad. Sci. U.S.A. 86:1603–1607).

Full length cDNA clones of Flk-1 were isolated from another day 8.5 mouse embryo cDNA library, which had been prepared according to the method of Okayama and Berg (1983), and a day 11.5 mouse embryo λgt11 library (Clonetech) using the $^{32}$p-labeled (Feinberg, A. P. and Vogelstein, B. 1983 Anal. Biochem. 132:6–13) 210bp PCR fragment.

6.1.2. Mouse Embryos

Balb/c mice were mated overnight and the morning of vaginal plug detection was defined as ½ day of gestation. For Northern blot analysis the frozen embryos were homogenized in 5 M guanidinium thiocyanate and RNA was isolated as described (Ullrich, A. et al., 1985, Nature 313:756–761). For in situ hybridization, the embryos were embedded in Tissue-Tek (Miles), frozen on the surface of liquid nitrogen and stored at −70C. prior to use.

6.1.3. Preparation of Probes

The 5'-located 2619 bp of the receptor cDNA were subcloned in the pGem3Z vector (Promega) as an EcoR1/BamH1 fragment. The probe for Northern blot hybridization was prepared by labelling the cDNA fragment with α-$^{32}$PdATP (Amersham) by random hexanucleotide priming (Boehringer; Feinberg, A. P. and Vogelstein, B., 1983 Anal. Biochem. 132:6–13).

For in situ hybridization a single-strand antisense DNA probe was prepared as described by Schnürch and Risau (Development, 1991 111:1143–54). The plasmid was linearized at the 3' end of the cDNA and a sense transcript was synthesized using SP6 RNA polymerase (Boehringer). The DNA was degraded using DNAase (RNAase free preparation, Boehringer Mannheim). With the transcript, a random-primed cDNA synthesis with α-$^{35}$S DATP (Amersham) was performed by reverse transcription with MMLV reverse transcriptase (BRL). To obtain small cDNA fragments of about 100 bp in average suitable for in situ hybridization, a high excess of primer was used. Subsequently the RNA transcript was partially hydrolyzed in 100 mM NaOH for 20 minutes at 70° C., and the probe was neutralized with the same amount of HC1 and purified with a Sephadex C50 column. After ethanol precipitation the probe was dissolved at a final specific activity of 5×10$^5$ cpm. For control hybridization a sense probe was prepared with the same method.

6.1.4. RNA Extraction and Northern Analysis

Total cytoplasmic RNA was isolated according to the acidic phenol-method of Chromczynski and Sacchi (1987). Poly(A$^+$) RNA aliquots were electrophoresed in 1.2% agarose formaldehyde (Sambrook, J. et al., 1989 Molecular Cloning: A Laboratory Manual 2nd ed. Cold Spring Harbor Laboratory Press) gels and transferred to nitrocellulose membranes (Schleicher & Schuell), Hybridizations were performed overnight in 50% formamide, 5×SSC (750 mM sodium chloride, 75 mM sodium citrate), 5×Denhardt's (0.1% Ficoll 400, 0.1% polyvinylpyrrolidone, 0.1% BSA) and −0.5% SDS at 42° C. with 1–3×10$^6$ cpm-ml$^{-1}$ of $^{32}$P-Random primed DNA probe, followed by high stringency washes in 0.2×SSC, 0.5% SDS at 52° C. The filters were exposed for 4 to 8 days.

6.1.5. In Situ Hybridization

Subcloning postfixation and hybridization was essentially performed according to Hogan et al. (1986). 10 $\mu$m thick sections were cut at −18° C. on a Leitz cryostat. For prehybridization treatment no incubation with 0.2 M HC1 for removing the basic proteins was performed. Sections were incubated with the $^{35}$S-cDNA probe (5×10$^4$cpm/$\mu$1) at 52° C. in a buffer containing 50% formamide, 300 mM NaCl, 10 mM Tris-HC1, 10 mM NaPO$_4$ (pH 6.8), 5 mM EDTA, 0.02% Ficoll 400, 0.01% polyvinylpyrrolidone, 0.02% BSA, 10 m/ml yeast RNA, 10% dextran sulfate, and 10 mM NaC1, 10 mM Tris-HC1, 10 mM NaPO$_4$ (pH 6.8), 5 mM EDTA, 10 Mm DTT at 52° C.). For autoradiography, slides were coated with Kodak NTB2 film emulsion and exposed for eight days. After developing, the sections were counterstained and toluidine blue or May-Grinwald.

6.1.6. Preparation of Antisera

The 3' primed EcoRV/HindII fragment comprising the 128 C-terminal amino acids of Flk-1 was subcloned in the fusion protein expression vector pGEX3X (Smith, D. B. and Johnson, K. S., 1990 Gene. 67:31–40; Pharmacia). The fusion protein was purified as described and used for immunizing rabbits. After the second boost the rabbits were bled and the antiserum was used for immunoprecipitation.

6.1.7. Transient Expression of Flk-1 in COS-1 Cells

Transfection of COS-1 cells was performed essentially as described by Chen and Okayama (1987 Mol. Cell. Biol. 7:2745–2752) and Gorman et al. (1989 Virology 171:377–385). Briefly, cells were seeded to a density of 1.0×10$^6$ per 10-cm dish and incubated overnight in DMEM containing 10% fetal calf serum (Gibco). 20 $\mu$g of receptor cDNA cloned into a cytomegalovirus promotor driven expression vector was mixed in 0.5 ml of 0.25 M CaCa$_2$, 0.5 ml of 2×BBS (280 mM NaCl, 1.5 mM Na$_2$HPO$_4$, 50 mM BES, pH 6.96 and incubated for 30 min at room temperature. The calcium phosphate/DNA solution was then added to the cells, swirled gently, and incubated for 18 hours at 37° C. under 3% CO$_2$. For ligand binding experiments, the cells were removed from the plate and treated as described below.

To obtain VEGF conditioned media, cells were transfected in 15-cm dishes. Media was collected after 48 h and VEGF was partially purified by affinity chromatography using heparin High Trap TM columns (Pharmacia) and concentrated by ultrafiltration (Ferrara, N. and Henzel, W. J. 1989 Biochem. Biophys. Res. Comm. 161:851–858). The concentration of VEGF was determined by a ligand competition assay with bovine aortic endothelial cells.

For autophosphorylation assays, cells were seeded in 6-well dishes (2×10$^5$ cells per well), transfected as described above, and starved for 24 h in DMEM containing 0.5% fetal calf serum. The cells were then treated with 500 pM VEGF for 10 min. at 37° C. or left untreated and were subsequently lysed as described by Kris et al. (1985). Flk-1 was immunoprecipitated with an antiserum raised in rabbits against the C-terminus of the receptor. The immunoprecipitates were separated on a 7.5% SDS polyacrylamide gel, transferred to nitrocellulose, and incubated with a mouse monoclonal antibody directed against phosphotyrosine (5E2; Fendly, B. M. et al., 1990 Cancer Research 50:1550–1558). Protein bands were visualized using horseradish peroxidase coupled goat anti-mouse antibody and the ECL™ (Amersham) detection system.

6.1.8. Radioiodination of VEGF

Recombinant human VEGF (5 $\mu$g; generously provided by Dr. H. Weich) was dissolved in 110 $\mu$l sodium phosphate buffer pH 76, and iodinated by the procedure of Hunter and Greenwood (1962). The reaction products were separated from the labeled protein by passage over a sephadex G50 column, pre-equilibrated with phosphate buffered saline (PBS) containing 0.7% bovine serum albumin (BSA), and aliquots of the collected fractions were counted before and after precipitation with 20% trichloracetic acid. The purity of the iodinated product was estimated to be superior to 90%, as determined by gel electrophoresis, and the specific activity was 77000 cpm/ng. The bioactivity of the iodinated VEGF was confirmed by comparison with the bioactivities of native VEGF using the tissue factor introduction assay described by Clauss, M. et al. (1990 J. Exp. Med. 172:1535–1545).

6.1.9. Crosslinking of VEGF to Flk-1

COS-1 cells transiently expressing Flk-1 and untransfected COS-1 cells were incubated with 200 pM $^{125}$I-VEGF at 4° C. overnight, then washed twice with PBS and exposed to 0.5 mM disuccinimidyl suberate (DSS) in PBS for 1 h at 4° C. The cells were lysed, Flk-1 immunoprecipitated, and analyzed by electrophoresis on a 7% polyacrylamide gel followed by autoradiography.

6.1.10. VEGF Binding

Ligand binding experiments were performed as described previously (Schumacher, R. et al., 1991, J. Biol. Chem. 266:19288–19295), COS-1 cells were grown in a 15-cm culture dish in DMEM for 48 h after transfection. Cells were then washed carefully with PBS and incubated with 5 ml of 25 mM EDTA in PBS for min. Cells were then removed from the plate, washed once with binding buffer (DMEM, 25 mM HEPES, pH 7.5, 0.15% gelatin) and resuspended in 5 ml of binding buffer to determine the cell number. In a total volume of 500 $\mu$l this cell suspension was incubated for 90 min at 15° C. with 10 pM $^{125}$I-VEGF, and increasing concentration of unlabeled ligand (from 0 to 7×10$^{-9}$), which was partially purified from conditioned media of COS-1 cells transiently expressing VEGF (164 amino acid form; Breier et al., *Development* vol. 114 (2) pp. 521–532 (1992). Leung et al., (*Science* vol. 246 pp. 1306–9 (1989) disclose cDNA clones for bovine and human VEGF). After incubation, cells were washed with PBS 0.1% PBS in the cold. Free ligand was removed by repeated centrifugation and resuspension in binding buffer. Finally, the $^{125}$I radioactivity bound to the cells were determined in a gamma counter (Riastar). Data obtained were analyzed by the method of Munson, P. J. and Rodbard, D. (1980 Anal. Biochem. 107:220–235).

6.1.11. Retroviral Vectors Encoding Transdominant-Negative Mutants of Flk-1

Recombinant retroviral vectors were constructed that contained the coding region for amino acids 1 through 806 of the Flk-1 receptor (pLX Flk-1 TM cl.1 and pLX Flk-1 TM cl.3, FIG. 12A). A recombinant virus containing the 541 N-terminal amino acids of the CSF-1 receptor/c-fms (pNTK cfms TM cl.7, FIG. 12B) was used as a control.

pLXSN Flk-1 TM was obtained by ligating the 5'-located 2619 bp of the Flk-1 cDNA encoding amino acids 1 to 806 as a ClaI/BamHI fragment to a BglII/HpaI linker, thereby designing a stop-codon 23 amino acids following the transmembrane region (5' GTC ATG GAT CTT CGT TAA 3' (SEQ ID NO. 3)). In a second step, the ClaI/HpaI fragment was subcloned into the ClaI/HpaI site of the pLXSN vector. Stable GP+E-86 cell lines producing ecotropic retroviruses expressing the wild type and mutated receptor constructs were generated as described by Redemann et al. (*Mol. Cell Biol.* vol 12, p. 491–498 (1992)).

For generation of pNTK c-fms TM, a stop codon was introduced behind amino acids 541 downstream from the transmembrane region of the c-fms cDNA using the oligonucleotide 5' TTG TAC AAG TAT AAG TAG TAG CCC AGG TAC CAG 3' (SEQ ID NO. 4). The mutated receptor was subcloned in the retroviral expression vector pNTK2 (Stewart et al., EMBO J., 6, 383–388 (1987). Stable GP+E-86 cell lines were obtained as described above.

6.1.12. The Capability of FLK-1 TM to form Signalling-Incompetent Heterodimers The capability of Flk-1 TM to form signalling incompetent heterodimers with the 180 kD wild type Flk-1 was demonstrated by coprecipitation of the truncated 130 kD receptor mutant with an antibody against the C-terminus of the intact receptor from lysates of COS cells transiently expressing both forms. Since the antibody could not recognize Flk-1 TM, coprecipitation was a consequence of heterdimerization.

To test the capability of Flk-1 TM to form signalling incompetent heterodimers with the wild-type Flk-1 in vivo, C6 gliobastoma tumor cells, available from the ATCC, accession number CCL 107, were implanted into nude mice either alone or coimplanted with virus producing cells. Injected cell numbers for the two sets of experiments are indicated below. Beginning at the time when the first tumors appeared, tumor volumes were measured every 2 to 3 days to obtain a growth curve. The results are discussed in Section 6.2.6 and shown in FIGS. 12 and 13.

| Number of Mice | Number of C6 Cells | Virus-producer Cell Line | Number of Virus-Cells |
|---|---|---|---|
| Experiment No. 1 | | | |
| 4 | $5 \times 10^5$ | pLXSN Flk-1 TM cl.3 | $1 \times 10^7$ |
| 4 | $5 \times 10^5$ | None | 0 |
| 4 | $5 \times 10^5$ | pNTK cfms TM cl.7 | $5 \times 10^6$ |
| Experiment No. 2 | | | |
| 4 | $2 \times 10^6$ | pLXSN Flk-1 TM cl.1 | $2 \times 10^7$ |
| 4 | $2 \times 10^6$ | pLXSN Flk-1 TM cl.3 | $2 \times 10^7$ |
| 4 | $2 \times 10^6$ | None | 0 |
| 4 | $2 \times 10^6$ | pNTK cfms TM cl.7 | $2 \times 10^7$ |

In another experiment, the same experimental conditions were performed except that the virus producing cells were injected five days after implantation of $10^6$ tumor cells.

In another experiment, co-implantation of C6 glioblastoma cells was with different relative amounts of retroviral cells producing comparable titers ($1 \times 10^6$ cfu/ml) of recombinant retrovirus. The effect of the inhibition of tumor growth was dose-dependent, with maximum achieved when the virus-producing cells were in 20-fold excess over the tumor cells. To confirm that the inhibition of the C6 glioblastoma growth was caused by dominant-negative action of the retrovirally expressed constructs on endothelial cells, the tumors were resected and analyzed. Comparison of the whole mount specimens revealed striking differences: whereas the control tumors exhibited a reddish surface, as expected for well-vascularized tissue, the inhibited cell implants were very pale. Histological staining of frozed sections revealed that the control tumors consisted of a homogenous mass of viable cells. Only very few and small necroses could be detected. In contrast, the much smaller, growth-inhibited tumor cell implants had an onion-like histological appearance, which was characterized by different tissue layers: a large, central necrosis was surrounded by a dense layer of viable tumor cells. Invasion of this tumor had not progressed, as evidenced by the presence of natural structures of the skin, such as the muscular cell layer.

The distribution of capillaries and blood vessels in the tissue specimens was determined by incubating frozen tissue sections with a rat monoclonal antibody specific for the endothelial cell adhesion antigen PECAM (De Vries et al., *Science* vol. 255, pp. 989–991 (1992)). While the tumors coimplanted with the control virus-producing cells displayed the pattern of capillaries and vessels expected for well-vascularized tissue, the growth-inhibited tumor cell implant exhibited a large central tumor cell necrosis, which was surrounded by a layer of viable tumor cells lacking blood vessels or capillaries. The tumor cells in this layer showed a higher cell density than the control tumor suggesting a significant reduction in tumor-induced edema formation. Since VEGF appears to induce vascular permeability in vivo, and was therefore also designated vascular permeability factor, inhibition of VEGF/Flk-1 interaction may inhibit tumor associated edema formation.

Flk-1 expression in proliferating endothelial cells of the tumor was confirmed by in situ hybridization of tissue sections with a $^{35}$S-labeled Flk-1 specific antisense cDNA probe and displayed the same distribution as immunostaining with endothelial cell-specific antibodies, indicating that proliferating endothelial cells expressed Flk-1. In situ hybridization with a neomycin resistance gene (neo$^r$) antisense probe confirmed the presence of retroviral sequences. The entire Flk-1 dominant-negative-inhibited tumor consisting of the retrovirus-producing and infected cells was neo$^r$-positive, a result that exactly matched that obtained with a Flk-1 specific probe. The morphology of tumors that had been coimplanted with control virus-producing cell was very similar, but the virus-producing cells were extensively infiltrated by infected tumor cells. In these tumors, which contained many capillaries and blood vessels, neo$^r$-positive signals were also found in endothelial cells.

C6 gliomas exhibit morphological characteristics of human glioblastoma multiforme such as necroses with palisading cells, a high degree of vascularization, and a similar expression pattern of VEGF and its receptors making this model an excellent tool to study anti-angiogenic therapy (Plate et al., Cancer Research vol. 53, pp. 5822–5827 (1993)).

6.1.13. Intracerebral Grafting of Glioma Cells

To test the capability of Flk-1 TM to form signalling incompetent heterodimers with the wild type Flk-1 in vivo, C6 glioma cells were transplanted intracranially into syngeneic rats with co-injection of a retrovirus-producing cell line.

To transplant glioma cells intracranially into rats, the rats (bodyweight 160–180 g) were anesthetized by i.p. injection of 100 mg/kg Ketamin (Ketaset$^R$) plus 5 mg/kg (Xylazine (Rompun$^R$). The dosage is dependent on the rat strain and should be determined before the experiments. Preanesthesia with isoflurane facilitates i.p. injection and onset of anesthesia. Approximately 3–10 minutes after i.p. injection, animals no longer respond to pain. If analgesia is not complete after 10 minutes, additional dose of 50 mg/kg Ketanest plus 2.5 mg/kg Rompun i.m. (50% of the initial i.p. dose) should be injected. The animals were adjusted in a commercially available small animal stereotactic apparatus. The skin was cleaned with alcohol and a median incision (approximately 1 cm in length) was performed over the skull using a sterile surgical blade. The skin was then slightly disattached from the skull. A burrhole was made using a dental driller on the right side of the hemisphere (coordinates: 2 mm lateral and 1 mm anterior to the bregma). Care was taken not to disrupt the meninges or to damage the brain (check via microscope). A hamilton syringe was placed in the burrhole at the level of the arachnoidea and then slowly lowered until the tip is 3 mm deep in the brain structure (the target point is the cauda-putamen, lateral to the frontal horn of the lateral ventricle). Two to twenty microliters of cells (depending of the amount of cells one wishes to graft) were slowly injected. The maximum volume rats tolerate is 20–25 microliters. If a higher volume is injected, the animal can die immediately due to increased intracranial pressure. After application of the cells, the syringe was not removed immediately in order to allow dissolution of the cells in the brain. After approximately 30 seconds, the syringe was removed slowly. Under these conditions no or very little liquid comes out of the burrhole. The skull was then cleaned and the animals did not bleed at the area operated (check via microscope). The skin was then closed with sutures. Approximately 20–30 minutes was needed for intracerebral grafting of tumor cells in one animal (plus anesthesia).

Animals are monitored for 18–22 days at which time surviving rats are sacrificed, their brains removed (quick frozen or fixed in formalin) and analyzed by standard techniques for measuring tumor volume.

| Experiment No. 1 | | | |
|---|---|---|---|
| Number of Rats | Number of C6 Cells | Virus-Producer Cell Line | Number of Virus-Cells |
| 8 | $5 \times 10^4$ | Flk-1 TM | $5 \times 10^6$ |
| 8 | $5 \times 10^6$ | 0 | 0 |

All cells were placed intracerebrally in a total volume of $\leq 25$ μl.

The results of this experiment are described in Section 6.2.6 and shown in FIGS. 16A and 16B.

6.1.14. Assay for and Identification of Organic Compounds That Modulate FLK-1 Mediated Signal Transduction Organic compounds that modulate Flk-1 receptor mediated signal transduction can be assayed in a cellular Flk-1 assay wherein modulation of Flk-1 receptor autophosphorylation is measured using an antiphosphotyrosine antibody. In the example shown below, the results are analyzed using a Western blot of electrophoresed cell lysates. Levels of phosphorylation as be measured by other techniques known in the art.

NIH3T3 cells expressing high levels of Flk-1 were seeded in 12-well plates at 250,000 cells/well in DMEM +0.5% calf serum and incubated overnight at 37° C. plus or minus the test substance. Flk-1 tyrosine kinase was stimulated by the addition of 100–500 pM of VEGF/well for 5–10 minutes at 37° C. After stimulation, cells were washed with phosphate buffered saline (PBS) and then lysed with 200 μl of sample buffer (100 mM Tris pH 6.8, 5% glycerol, 1.75% SDS, 1.25 mM EDTA, 0.5 mM sodium vanadate, 2.5 mM sodium pyrophosphate, 1.25% 2-mercaptoethanol). Cell lysates were transferred to centrifuge tubes, boiled at 100° C. for 5 minutes, and then centrifuged at 16,000 G for 5 minutes. Supernatants were removed and stored at −80° C.

For the Western blot assay, forty microliters of saved supernatant per lane were loaded onto a 7.5% SDS-PAGE gel (10 lanes/gel, 1.5 mm thick) and run at 120 V until the dye reached the bottom of the gel. The running buffer used contains 20 mM Tris, 192 mM glycine and 0.1% SDS. Proteins were then transferred to nitrocellulose membrane (Bio-Rad) at 500 mA for 1 hour using ice-cold transblotting buffer containing 50% tank buffer, 20% methanol and 30% water. The nitrocellulose was then blocked with 5% nonfat milk in TBST (50 mM Tris, 150 mM NaCl, and 0.1% triton) for 1 hour or overnight, immunoblotted with a monoclonal antibody against phospho-tyrosine (UBI or Sigma, 1:3000) in TBST for 1 hour, followed by goat anti-mouse (Bio-Rad 1:3000) in TBST-buffer for another 1 hour. Protein bands were detected by soaking the membrane in ECL chemiluminescence system (Amersham Corp., prepared by mixing equal volumes of reagent 1 and 2) for 1 minute and then exposing the film for about 1–10 minutes.

6.1.15. Synthesis of a 3-Phenyl-1, 4-Diaza-Anthracene

A preferred method of synthesis of AG1385 is as follows: 0.47 grams (3 mM) 2,3-diaminonaphthalene and 0.47 grams phenyl gloxal hydrate in 20 ml ethanol were refluxed 1.5 hour. Cooling and filtering gave 0.5 g (65%) of a light brown solid, mp 163 ° C. NMR CDCl3: δ 9.38 (1H, l.c., H2), 8.71, 8.67 (2H, 2d, H5,10), 8.25, 8.10 (4H, AA'BB'm, H6–9), 7.58(5H, m, Ph). MS: +256(M+, 100%), 229 (M-CN, 12%), 126(71%) m/e.

6.2. Results 6.2.1. Isolation of Flk-1

To identify RTKs that are expressed during mouse development, PCR assays using two degenerate oligonucleotide primer pools that were designed on the basis of highly conserved sequences within the kinase domain of RTKs were performed (Hanks, S. K. et al. 1988, Science 241:42–52). DNA extracted from a λgt10 cDNA library of day 8.5 mouse embryos (Fahrner, K. et al., 1987, EMBO. J., 6:1497–1508), a stage in mouse development at which many differentiation processes begin was used as the template in the PCR assays. In a parallel approach, with the intention of identifying RTKs that regulate angiogenesis, similar primers were used for the amplification of RTK cDNA sequences from capillary endothelial cells that had been isolated from the brains of postnatal day 4–8 mice, a time at which brain endothelial cell proliferation is maximal (Robertson, P. L. et al., 1985, Devel. Brain Res. 23:219–223). Both approaches yielded cDNA sequences (FIG. 11, SEQ. ID NO.:) encoding the recently described fetal liver RTK, Flk-1 (Matthews, W. et al., 1991, Proc. Natl. Acad. Sci. U.S.A. 88:9026–9030). Based on amino acid homology, this receptor is a member of the type III subclass of RTKs (Ullrich, A. and Schlessinger, J. 1990, Cell 61:203–212) and is closely related to human flt, which also contains seven immunoglobin-like repeats in its extracellular domain in contrast to other RTKs of that subfamily, which contain only five such repeat structures (Matthews, W. et al., 1991, Proc. Natl. Acad Sci. U.S.A. 88:9026–9030). Sequence comparisons of Flk-1 with KDR (Terman, B. I. et al., 1991, Oncogene 6:1677–1683) and TKr-C (Sarzani, R. et al., 1992, Biochem. Biophys. Res. Comm. 186:706–714) suggest that these are the human and rat homologues of Flk-1, respectively (FIG. 1).

6.2.2 Expression of Flk-1 mRNA During Embryonic Development

As a first step towards the elucidation of the biological function of Flk-1, the expression of Flk-1 mRNA was analyzed in mouse embryos at different development stages. Northern blot hybridization experiments indicated abundant expression of a major 5.5 kb MRNA between day 9.5 and day 18.5, with an apparent decline towards the end of gestation (FIG. 2A). In postnatal day 4–8 brain capillaries Flk-1 mRNA was found to be highly enriched compared to total brain mRNA (FIG. 2B).

In situ hybridization experiments were performed to obtain more detailed information about the expression of Flk-1 during different embryonal stages. A single-stranded antisense, 2619-nucleotide-long DNA probe comprising the Flk-1 extracellular domain was used as a probe because it generated the most specific hybridization signals. As an example, a parasagittal section of a day 14.5 embryo is shown in FIGS. 3A, 3b and 3C. High levels of hybridization were detected in the ventricle of the heart, the lung, and the meninges; other tissues such as brain, liver, and mandible appeared to contain fewer cells expressing Flk-1 mRNA. Thin strands of Flk-1 expression were also observed in the intersegmental regions of the vertebrae and at the inner surface of the atrium and the aorta. Higher magnification revealed that the expression of Flk-1 seemed to be restricted to capillaries and blood vessels. Closer examination of the heart, for example, showed positive signals only in the ventricular capillaries and endothelial lining of the atrium (FIG. 4A). In the lung, Flk-1 expression was detected in peribronchial capillaries, but was absent from bronchial epithelium (FIG. 4D). The aorta showed strong hybridization in endothelial cells, but not in the muscular layer (FIG. 4C).

6.2.3. Expression of Flk-1 During Organ Angiogenesis

The neuroectoderm in the telencephalon of a day 11.5 mouse embryo is largely avascular; the first vascular sprouts begin to radially invade the organ originating from the perineural vascular plexus (Bär, J., 1980, Adv. Anat. Embryol. Cell. Biol. 59:1–62; Risau, W. and Lemmon, V. 1988, Dev. Biol. 125:441–450). At this stage, expression of Flk-1 was high in the perineural vascular plexus and in invading vascular sprouts, as shown in FIG. 5A. These in situ hybridization analyses indicated that the proliferating endothelial cells of an angiogenic sprout expressed the Flk-1 mRNA. At day 14.5, when the neuroectoderm is already highly vascularized, numerous radial vessels as well as branching vessels of the intraneural plexus contained large amounts of Flk-1 mRNA (FIG. 5B). At postnatal day 4, when sprouting and endothelial cell proliferation is at its highest, strong expression of Flk-1 mRNA was observed in endothelial cells (FIG. 5C). Conversely, in the adult brain when angiogenesis has ceased, Flk-1 expression was very low (FIG. 5D) and appeared to be restricted mainly to the choroid plexus (FIGS. 6A and 6B). In the choroid plexus, cells in the inner vascular layer expressed Flk-1 mRNA, while epithelial cells did not (FIG. 6A, 6B).

The embryonic kidney is vascularized by an angiogenic process (Ekblom, P. et al., 1982, Cell Diff. 11:35–39). Glomerular and peritubular capillaries develop synchronously with epithelial morphogenesis. In the postnatal day 4 kidney, in addition to other capillaries, prominent expression of Flk-1 was observed in the presumptive glomerular capillaries (FIG. 7A). This expression persisted in the adult kidney (FIG. 7C and 7D) and then seemed to be more confined to the glomerular compared to the early postnatal kidney.

6.2.4. Flk-1 Expression in Endothelial Cell Progenitors

To investigate the possible involvement of Flk-1 in the early stages of vascular development, analysis of embryos at different stages during blood island formation were performed. In a sagittal section of the deciduum of a day 8.5 mouse embryo, Flk-1 expression was detected on maternal blood vessels in the deciduum, in the yolk sac and in the trophectoderm. Flk-1 mRNA was also found in the allantois and inside the embryo, mainly located in that part where mesenchyma is found (FIG. 8A). At a higher magnification of the maternal deciduum, high levels of Flk-1 mRNA expression were found in the inner lining of blood vessels, which consist of endothelial cells (FIG. 8B). In the yolk sac, hybridization signals were confined to the mesodermal layer, in which the hemangioblasts differentiate (FIG. 8C). FIG. 8D shows a blood island at higher magnification, in which the peripheral angioblasts expressed a high level of Flk-1 mRNA.

6.2.5. Flk-1 Is a High Affinity Receptor for VEGF

Detailed examination of in situ hybridization results and comparison with those for VEGF recently reported by Breier, G. et al. (1992, Development 114:521–532) revealed a remarkable similarity in expression pattern. Furthermore, Flk-1 expression in the glomerular endothelium and VEGF in the surrounding epithelial cells (Breier, G. et al., 1992, Development 114:521–532) raised the possibility of a paracrine relationship between these cells types and suggested therefore a ligand-receptor relationship for VEGF and Flk-1, respectively. In order to test this hypothesis, the full-length Flk-1 cDNA was cloned into the mammalian expression vector pCMV, which contains transcriptional control elements of the human cytomegalovirus (Gorman, C. M. et al., 1989, Virology 171:377–385). For transient expression of the receptor, the Flk-1 expressing plasmid was then transfected into COS-1 fibroblasts.

Specific binding of VEGF to the Flk-1 RTK was demonstrated by crosslinking and competition binding experiments. Purified $^{125}$I-labeled VEGF was incubated with COS-1 cells transfected with the pCMV-Flk-1 expression vector. Crosslinking with DSS and subsequent analysis of immunoprecipitation, PAGE, and autoradiography revealed an approximately 220 kD band which was not detected in the control experiment with untransfected COS-1 cells and is likely to represent the VEGF/Flk-1 receptor complex (FIG. 9A). In addition, VEGF competed with $^{125}$I-VEGF binding to Flk-1 expressing COS-1 cells (FIG. 9B), whereas untransfected COS-1 cells did not bind $^{125}$I-VEGF. The interaction of VEGF with the receptor on transfected cells was specific, as PDGF-BB did not compete with binding of $^{125}$I-VEGF. Analysis of the binding data revealed a Kd of about $10^{-10}$ M, suggesting that Flk-1 is a high affinity receptor of VEGF. This finding, together with the Flk-1 and VEGF in situ hybridization results strongly suggests that Flk-1 is a physiologically relevantly receptor for VEGF.

An autophosphorylation assay was performed to confirm the biological relevance of VEGF binding to the Flk-1 receptor. COS1 cells which transiently expressed Flk-1 were starved in DMEM containing 0.5% fetal calf serum for 24 h, stimulated with 0.5 mM VEGF, and lysed. The receptors were immunoprecipitated with the Flk-1 specific polyclonal antibody CT128, and then analyzed by SDS-PAGE and subsequent immunoblotting using the antiphosphotyrosine antibody 5E2 (Fendly, B. M. et al., 1990, Cancer Research 50:1550–1558). A shown in FIG. 10, VEGF stimulation of Flk-1 expressing cells led to a significant induction of tyrosine phosphorylation of the 180 kD Flk-1 receptor.

6.2.6. Inhibition of Tumor Growth by Transdominant-Negative Inhibition of Flk-1

The Flk-1 receptor is believed to play a major role in vasculogenesis and angiogenesis. Therefore, inhibition of Flk-1 activity may inhibit vasculogenesis of a developing tumor, for example, and inhibit its growth.

The dominant-negative potential of Flk-1 TM was first examined by measuring its influence on the mitogenic response of Flk-1-expressing NIH 3T3 cells after superinfection with the Flk-1 TM virus. [$^3$H] thymidine incorporation in the 3T3 Flk-1 cell line was maximally stimulated by 500 pM VEGF, with an $EC_{50}$ of about 100 pM. After superinfection with the Flk-1 TM virus, the Flk-1/VEGF-mediated mitogenic response was dramatically suppressed even at a ligand concentration of 5 nM. While 3T3 Flk-1/Flk-1 TM cells expressed wild type Flk-1 levels equal to the parental line, they displayed, due to overexpression of Flk-1 TM, a 6-fold increase of cell surface receptors, as determined by $^{125}$I-VEGF binding. These results were further extended by Flk-1 TM virus-induced suppression of Flk-1 transforming activity and demonstrated not only that mutant and wild type Flk-1 physically associated, but also that this interaction generated signalling-incompetent heterodimers. The dominant-negative inhibitory effect which was achieved at a fivefold excess of Flk-1 TM could not be overcome by a 50 fold ligand excess relative to the $EC_{50}$ value for mitogenic activation. Moreover, Flk-1 TM did not interfere with the signal transduction of the α- and β-PDGF-receptors, demonstrating the specificity of its dominant-negative action.

To test the dominant-negative potential in vivo, tumor cells (C6 rat glioblastoma) and mouse cells producing a recombinant retrovirus encoding a truncated Flk-1 receptor were mixed and implanted subcutaneously into nude mice. The implanted C6 glioblastoma cells secrete VEGF which will bind to and activate the Flk-1 receptors expressed on the surface of mouse endothelial cells. In the absence of any inhibitors of vasculogenesis, the endothelial cells will proliferate and migrate towards the tumor cells. Alternatively, if at the time of injection, the tumor cells are co-injected with cells producing recombinant retrovirus encoding the dominant-negative Flk-1, or if the cells producing recombinant retrovirus are injected after the tumor cells, the endothelial cells growing towards the implanted tumor cells will become infected with recombinant retrovirus which may result in dominant-negative Flk-1 mutant expression and inhibition of endogenous Flk-1 signaling. Suppression of endothelial cell proliferation and migration will result in failure of the implanted tumor cells to become vascularized which will lead to inhibition of tumor growth. As shown in FIGS. 12, 13 and 15 tumor growth is significantly inhibited in mice receiving implantations of cells producing truncated Flk-1 indicating that expression of a truncated Flk-1 receptor can act in a dominant-negative manner to inhibit the activity of endogenous wild-type Flk-1.

As a control, any direct influence of the retroviruses on the growth of the tumor cells can be excluded by growing C6 cells in conditioned media of the different retrovirus-producing cell lines, without any effect on their growth behavior.

To test the role that Flk-1 receptor is believed to play in angiogenesis and vasculogenesis, and to identify potential inhibitors of the Flk-1 receptor, tumor cells (C6 rat glioblastoma) and mouse cells producing a recombinant retrovirus encoding a truncated Flk-1 receptor were mixed and implanted intracranially in rats. The implanted C6 glioblastoma cells secrete VEGF which will bind to and activate the Flk-1 receptors expressed on the surface of rat endothelial cells. Inhibition of Flk-1 receptor signal transduction is measured as inhibition of intracranially tumor growth as seen in rats co-injected with the Flk-1 TM.

Analogous experiments with a variety of other tumor types support the data obtained with the C6 glioblastoma nude mouse subcutaneous model and strongly demonstrate that inhibition of solid tumor growth can be effected by preventing angiogenesis. Angiogenesis a process that is normally regulated by VEGF, which when secreted by tumor cells attracts and stimulated in a paracrine fashion Flk-1 -positive vascular endothelial cells.

6.2.7. Identification of an Organic Compound That Inhibits FLK-1 Receptor Phosphorylation To identify organic compounds that inhibit Flk-1 receptor, organic compounds have been tested in the cellular assay described in Section 6.1.14 for their ability to inhibit Flk-1 receptor phosphorylation. Examples of some of the compounds tested are shown below.

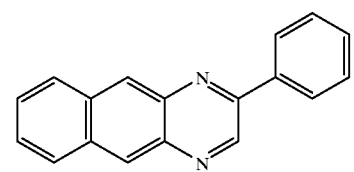

A14

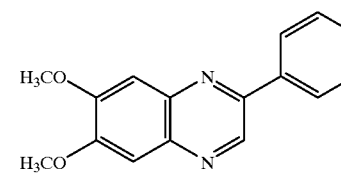

A9

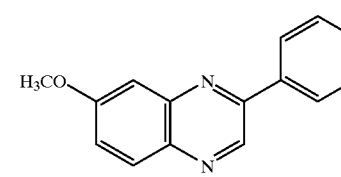

A2

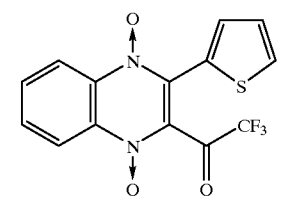

A5

Compound A14 was shown to inhibit Flk-1 receptor phosphorylation almost completely at a test concentration of 100 μM (FIG. 17). Thus this is an example of a compound that could be useful for antagonizing Flk-1 receptor signal transduction and therefore may be useful for inhibiting the Flk-1 receptor mediated mitogenic signal. Accordingly, compound A14 may be therapeutically useful in the treatment of solid tumors by inhibiting angiogenesis.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

All references cited herein are hereby incorporated by reference in their entirety.

What is claimed is:

1. A method for inhibiting angiogenesis and/or vasculogenesis in a subject in need thereof, comprising administering to said subject a therapeutically effective amount of an organic compound that inhibits the tyrosine phosphorylation of FLK-1 effected by VEGF binding to FLK-1.

2. A method for inhibiting angiogenesis and/or vasculogenesis in a subject in need thereof, comprising administering to said subject a therapeutically effective amount of an organic compound that inhibits VEGF binding to FLK-1.

3. A method of treating a disease which is associated with VEGF and/or FLK-1 mediated proliferation of blood vessels in a mammal, comprising administering to said mammal a therapeutically effective amount of an organic compound that inhibits the tyrosine phosphorylation of FLK-1 effected by VEGF binding to FLK-1.

4. The method of claim 3, wherein the disease is a solid tumor.

5. The method of claim 3, wherein the disease is rheumatoid arthritis.

6. The method of claim 3, wherein the disease is retinopathy.

7. The method of claim 1, 2, 3, 4, 5, or 6, wherein the FLK-1 is a murine receptor.

8. The method of claim 1, 2, 3, 4, 5, or 6, wherein said organic compound inhibits the enzymatic activity of FLK-1.

9. The method of claim 1, 2, 3, 4, 5, or 6, wherein said organic compound binds to the intracellular domain of FLK-1.

10. The method of claim 1, 2, 3, 4, 5, or 6, wherein said organic compound binds to the catalytic domain of FLK-1.

11. The method of claim 1, 2, 3, 4, 5, or 6, wherein said organic compound is administered in a pharmaceutical composition.

12. The method of claim 1, 2, 3, 4, 5, or 6, wherein the FLK-1 is a human receptor.

13. The method of claim 12, wherein said organic compound inhibits the enzymatic activity of FLK-1.

14. The method of claim 12, wherein said organic compound binds to the intracellular domain of FLK-1.

15. The method of claim 12, wherein said organic compound binds to the catalytic domain of FLK-1.

16. The method of claim 12, wherein said organic compound is administered in a pharmaceutical composition.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 5470 base pairs
      (B) TYPE: nucleic acid
      (C) STRANDEDNESS: unknown
      (D) TOPOLOGY: unknown (ii) MOLECULE TYPE: DNA (ix) FEATURE:
      (A) NAME/KEY: CDS
      (B) LOCATION: 286..4386

(xi) SEQUENCE DESCRIPTION: SEQ ID NO:1:

```
TATAGGGCGA ATTGGGTACG GGACCCCCCT CGAGGTCGAC GGTATCGATA AGCTTGATAT     60

CGAATTCGGG CCCAGACTGT GTCCCGCAGC CGGGATAACC TGGCTGACCC GATTCCGCGG    120

ACACCGCTGA CAGCCGCGGC TGGAGCCAGG GCGCCGGTGC CCCGCGCTCT CCCCGGTCTT    180

GCGCTGCGGG GGCCATACCG CCTCTGTGAC TTCTTTGCGG GCCAGGGACG GAGAAGGAGT    240

CTGTGCCTGA GAAACTGGGC TCTGTGCCCA GGCGCGAGGT GCAGG ATG GAG AGC        294
                                                  Met Glu Ser
                                                    1

AAG GCG CTG CTA GCT GTC GCT CTG TGG TTC TGC GTG GAG ACC CGA GCC      342
Lys Ala Leu Leu Ala Val Ala Leu Trp Phe Cys Val Glu Thr Arg Ala
    5                  10                  15

GCC TCT GTG GGT TTG ACT GGC GAT TTT CTC CAT CCC CCC AAG CTC AGC      390
Ala Ser Val Gly Leu Thr Gly Asp Phe Leu His Pro Pro Lys Leu Ser
 20                  25                  30                  35

ACA CAG AAA GAC ATA CTG ACA ATT TTG GCA AAT ACA ACC CTT CAG ATT      438
Thr Gln Lys Asp Ile Leu Thr Ile Leu Ala Asn Thr Thr Leu Gln Ile
                 40                  45                  50

ACT TGC AGG GGA CAG CGG GAC CTG GAC TGG CTT TGG CCC AAT GCT CAG      486
Thr Cys Arg Gly Gln Arg Asp Leu Asp Trp Leu Trp Pro Asn Ala Gln
             55                  60                  65

CGT GAT TCT GAG GAA AGG GTA TTG GTG ACT GAA TGC GGC GGT GGT GAC      534
Arg Asp Ser Glu Glu Arg Val Leu Val Thr Glu Cys Gly Gly Gly Asp
         70                  75                  80

AGT ATC TTC TGC AAA ACA CTC ACC ATT CCC AGG GTG GTT GGA AAT GAT      582
Ser Ile Phe Cys Lys Thr Leu Thr Ile Pro Arg Val Val Gly Asn Asp
     85                  90                  95

ACT GGA GCC TAC AAG TGC TCG TAC CGG GAC GTC GAC ATA GCC TCC ACT      630
Thr Gly Ala Tyr Lys Cys Ser Tyr Arg Asp Val Asp Ile Ala Ser Thr
100                 105                 110                 115

GTT TAT GTC TAT GTT CGA GAT TAC AGA TCA CCA TTC ATC GCC TCT GTC      678
Val Tyr Val Tyr Val Arg Asp Tyr Arg Ser Pro Phe Ile Ala Ser Val
                120                 125                 130
```

```
AGT GAC CAG CAT GGC ATC GTG TAC ATC ACC GAG AAC AAG AAC AAA ACT      726
Ser Asp Gln His Gly Ile Val Tyr Ile Thr Glu Asn Lys Asn Lys Thr
            135                 140                 145

GTG GTG ATC CCC TGC CGA GGG TCG ATT TCA AAC CTC AAT GTG TCT CTT      774
Val Val Ile Pro Cys Arg Gly Ser Ile Ser Asn Leu Asn Val Ser Leu
        150                 155                 160

TGC GCT AGG TAT CCA GAA AAG AGA TTT GTT CCG GAT GGA AAC AGA ATT      822
Cys Ala Arg Tyr Pro Glu Lys Arg Phe Val Pro Asp Gly Asn Arg Ile
165                 170                 175

TCC TGG GAC AGC GAG ATA GGC TTT ACT CTC CCC AGT TAC ATG ATC AGC      870
Ser Trp Asp Ser Glu Ile Gly Phe Thr Leu Pro Ser Tyr Met Ile Ser
180                 185                 190                 195

TAT GCC GGC ATG GTC TTC TGT GAG GCA AAG ATC AAT GAT GAA ACC TAT      918
Tyr Ala Gly Met Val Phe Cys Glu Ala Lys Ile Asn Asp Glu Thr Tyr
            200                 205                 210

CAG TCT ATC ATG TAC ATA GTT GTG GTT GTA GGA TAT AGG ATT TAT GAT      966
Gln Ser Ile Met Tyr Ile Val Val Val Val Gly Tyr Arg Ile Tyr Asp
        215                 220                 225

GTG ATT CTG AGC CCC CCG CAT GAA ATT GAG CTA TCT GCC GGA GAA AAA     1014
Val Ile Leu Ser Pro Pro His Glu Ile Glu Leu Ser Ala Gly Glu Lys
230                 235                 240

CTT GTC TTA AAT TGT ACA GCG AGA ACA GAG CTC AAT GTG GGG CTT GAT     1062
Leu Val Leu Asn Cys Thr Ala Arg Thr Glu Leu Asn Val Gly Leu Asp
245                 250                 255

TTC ACC TGG CAC TCT CCA CCT TCA AAG TCT CAT CAT AAG AAG ATT GTA     1110
Phe Thr Trp His Ser Pro Pro Ser Lys Ser His His Lys Lys Ile Val
260                 265                 270                 275

AAC CGG GAT GTG AAA CCC TTT CCT GGG ACT GTG GCG AAG ATG TTT TTG     1158
Asn Arg Asp Val Lys Pro Phe Pro Gly Thr Val Ala Lys Met Phe Leu
            280                 285                 290

AGC ACC TTG ACA ATA GAA AGT GTG ACC AAG AGT GAC CAA GGG GAA TAC     1206
Ser Thr Leu Thr Ile Glu Ser Val Thr Lys Ser Asp Gln Gly Glu Tyr
        295                 300                 305

ACC TGT GTA GCG TCC AGT GGA CGG ATG ATC AAG AGA AAT AGA ACA TTT     1254
Thr Cys Val Ala Ser Ser Gly Arg Met Ile Lys Arg Asn Arg Thr Phe
310                 315                 320

GTC CGA GTT CAC ACA AAG CCT TTT ATT GCT TTC GGT AGT GGG ATG AAA     1302
Val Arg Val His Thr Lys Pro Phe Ile Ala Phe Gly Ser Gly Met Lys
325                 330                 335

TCT TTG GTG GAA GCC ACA GTG GGC AGT CAA GTC CGA ATC CCT GTG AAG     1350
Ser Leu Val Glu Ala Thr Val Gly Ser Gln Val Arg Ile Pro Val Lys
340                 345                 350                 355

TAT CTC AGT TAC CCA GCT CCT GAT ATC AAA TGG TAC AGA AAT GGA AGG     1398
Tyr Leu Ser Tyr Pro Ala Pro Asp Ile Lys Trp Tyr Arg Asn Gly Arg
            360                 365                 370

CCC ATT GAG TCC AAC TAC ACA ATG ATT GTT GGC GAT GAA CTC ACC ATC     1446
Pro Ile Glu Ser Asn Tyr Thr Met Ile Val Gly Asp Glu Leu Thr Ile
        375                 380                 385

ATG GAA GTG ACT GAA AGA GAT GCA GGA AAC TAC ACG GTC ATC CTC ACC     1494
Met Glu Val Thr Glu Arg Asp Ala Gly Asn Tyr Thr Val Ile Leu Thr
390                 395                 400

AAC CCC ATT TCA ATG GAG AAA CAG AGC CAC ATG GTC TCT CTG GTT GTG     1542
Asn Pro Ile Ser Met Glu Lys Gln Ser His Met Val Ser Leu Val Val
405                 410                 415

AAT GTC CCA CCC CAG ATC GGT GAG AAA GCC TTG ATC TCG CCT ATG GAT     1590
Asn Val Pro Pro Gln Ile Gly Glu Lys Ala Leu Ile Ser Pro Met Asp
420                 425                 430                 435

TCC TAC CAG TAT GGG ACC ATG CAG ACA TTG ACA TGC ACA GTC TAC GCC     1638
Ser Tyr Gln Tyr Gly Thr Met Gln Thr Leu Thr Cys Thr Val Tyr Ala
            440                 445                 450
```

```
AAC CCT CCC CTG CAC CAC ATC CAG TGG TAC TGG CAG CTA GAA GAA GCC    1686
Asn Pro Pro Leu His His Ile Gln Trp Tyr Trp Gln Leu Glu Glu Ala
            455                 460                 465

TGC TCC TAC AGA CCC GGC CAA ACA AGC CCG TAT GCT TGT AAA GAA TGG    1734
Cys Ser Tyr Arg Pro Gly Gln Thr Ser Pro Tyr Ala Cys Lys Glu Trp
            470                 475                 480

AGA CAC GTG GAG GAT TTC CAG GGG GGA AAC AAG ATC GAA GTC ACC AAA    1782
Arg His Val Glu Asp Phe Gln Gly Gly Asn Lys Ile Glu Val Thr Lys
            485                 490                 495

AAC CAA TAT GCC CTG ATT GAA GGA AAA AAC AAA ACT GTA AGT ACG CTG    1830
Asn Gln Tyr Ala Leu Ile Glu Gly Lys Asn Lys Thr Val Ser Thr Leu
500                 505                 510                 515

GTC ATC CAA GCT GCC AAC GTG TCA GCG TTG TAC AAA TGT GAA GCC ATC    1878
Val Ile Gln Ala Ala Asn Val Ser Ala Leu Tyr Lys Cys Glu Ala Ile
            520                 525                 530

AAC AAA GCG GGA CGA GGA GAG AGG GTC ATC TCC TTC CAT GTG ATC AGG    1926
Asn Lys Ala Gly Arg Gly Glu Arg Val Ile Ser Phe His Val Ile Arg
            535                 540                 545

GGT CCT GAA ATT ACT GTG CAA CCT GCT GCC CAG CCA ACT GAG CAG GAG    1974
Gly Pro Glu Ile Thr Val Gln Pro Ala Ala Gln Pro Thr Glu Gln Glu
            550                 555                 560

AGT GTG TCC CTG TTG TGC ACT GCA GAC AGA AAT ACG TTT GAG AAC CTC    2022
Ser Val Ser Leu Leu Cys Thr Ala Asp Arg Asn Thr Phe Glu Asn Leu
            565                 570                 575

ACG TGG TAC AAG CTT GGC TCA CAG GCA ACA TCG GTC CAC ATG GGC GAA    2070
Thr Trp Tyr Lys Leu Gly Ser Gln Ala Thr Ser Val His Met Gly Glu
580                 585                 590                 595

TCA CTC ACA CCA GTT TGC AAG AAC TTG GAT GCT CTT TGG AAA CTG AAT    2118
Ser Leu Thr Pro Val Cys Lys Asn Leu Asp Ala Leu Trp Lys Leu Asn
            600                 605                 610

GGC ACC ATG TTT TCT AAC AGC ACA AAT GAC ATC TTG ATT GTG GCA TTT    2166
Gly Thr Met Phe Ser Asn Ser Thr Asn Asp Ile Leu Ile Val Ala Phe
            615                 620                 625

CAG AAT GCC TCT CTG CAG GAC CAA GGC GAC TAT GTT TGC TCT GCT CAA    2214
Gln Asn Ala Ser Leu Gln Asp Gln Gly Asp Tyr Val Cys Ser Ala Gln
            630                 635                 640

GAT AAG AAG ACC AAG AAA AGA CAT TGC CTG GTC AAA CAG CTC ATC ATC    2262
Asp Lys Lys Thr Lys Lys Arg His Cys Leu Val Lys Gln Leu Ile Ile
            645                 650                 655

CTA GAG CGC ATG GCA CCC ATG ATC ACC GGA AAT CTG GAG AAT CAG ACA    2310
Leu Glu Arg Met Ala Pro Met Ile Thr Gly Asn Leu Glu Asn Gln Thr
660                 665                 670                 675

ACA ACC ATT GGC GAG ACC ATT GAA GTG ACT TGC CCA GCA TCT GGA AAT    2358
Thr Thr Ile Gly Glu Thr Ile Glu Val Thr Cys Pro Ala Ser Gly Asn
            680                 685                 690

CCT ACC CCA CAC ATT ACA TGG TTC AAA GAC AAC GAG ACC CTG GTA GAA    2406
Pro Thr Pro His Ile Thr Trp Phe Lys Asp Asn Glu Thr Leu Val Glu
            695                 700                 705

GAT TCA GGC ATT GTA CTG AGA GAT GGG AAC CGG AAC CTG ACT ATC CGC    2454
Asp Ser Gly Ile Val Leu Arg Asp Gly Asn Arg Asn Leu Thr Ile Arg
            710                 715                 720

AGG GTG AGG AAG GAG GAT GGA GGC CTC TAC ACC TGC CAG GCC TGC AAT    2502
Arg Val Arg Lys Glu Asp Gly Gly Leu Tyr Thr Cys Gln Ala Cys Asn
            725                 730                 735

GTC CTT GGC TGT GCA AGA GCG GAG ACG CTC TTC ATA ATA GAA GGT GCC    2550
Val Leu Gly Cys Ala Arg Ala Glu Thr Leu Phe Ile Ile Glu Gly Ala
740                 745                 750                 755

CAG GAA AAG ACC AAC TTG GAA GTC ATT ATC CTC GTC GGC ACT GCA GTG    2598
Gln Glu Lys Thr Asn Leu Glu Val Ile Ile Leu Val Gly Thr Ala Val
```

-continued

```
                 760                 765                 770
ATT GCC ATG TTC TTC TGG CTC CTT CTT GTC ATT GTC CTA CGG ACC GTT         2646
Ile Ala Met Phe Phe Trp Leu Leu Leu Val Ile Val Leu Arg Thr Val
            775                 780                 785

AAG CGG GCC AAT GAA GGG GAA CTG AAG ACA GGC TAC TTG TCT ATT GTC         2694
Lys Arg Ala Asn Glu Gly Glu Leu Lys Thr Gly Tyr Leu Ser Ile Val
        790                 795                 800

ATG GAT CCA GAT GAA TTG CCC TTG GAT GAG CGC TGT GAA CGC TTG CCT         2742
Met Asp Pro Asp Glu Leu Pro Leu Asp Glu Arg Cys Glu Arg Leu Pro
    805                 810                 815

TAT GAT GCC AGC AAG TGG GAA TTC CCC AGG GAC CGG CTG AAA CTA GGA         2790
Tyr Asp Ala Ser Lys Trp Glu Phe Pro Arg Asp Arg Leu Lys Leu Gly
820                 825                 830                 835

AAA CCT CTT GGC CGC GGT GCC TTC GGC CAA GTG ATT GAG GCA GAC GCT         2838
Lys Pro Leu Gly Arg Gly Ala Phe Gly Gln Val Ile Glu Ala Asp Ala
                840                 845                 850

TTT GGA ATT GAC AAG ACA GCG ACT TGC AAA ACA GTA GCC GTC AAG ATG         2886
Phe Gly Ile Asp Lys Thr Ala Thr Cys Lys Thr Val Ala Val Lys Met
            855                 860                 865

TTG AAA GAA GGA GCA ACA CAC AGC GAG CAT CGA GCC CTC ATG TCT GAA         2934
Leu Lys Glu Gly Ala Thr His Ser Glu His Arg Ala Leu Met Ser Glu
        870                 875                 880

CTC AAG ATC CTC ATC CAC ATT GGT CAC CAT CTC AAT GTG GTG AAC CTC         2982
Leu Lys Ile Leu Ile His Ile Gly His His Leu Asn Val Val Asn Leu
    885                 890                 895

CTA GGC GCC TGC ACC AAG CCG GGA GGG CCT CTC ATG GTG ATT GTG GAA         3030
Leu Gly Ala Cys Thr Lys Pro Gly Gly Pro Leu Met Val Ile Val Glu
900                 905                 910                 915

TTC TGC AAG TTT GGA AAC CTA TCA ACT TAC TTA CGG GGC AAG AGA AAT         3078
Phe Cys Lys Phe Gly Asn Leu Ser Thr Tyr Leu Arg Gly Lys Arg Asn
                920                 925                 930

GAA TTT GTT CCC TAT AAG AGC AAA GGG GCA CGC TTC CGC CAG GGC AAG         3126
Glu Phe Val Pro Tyr Lys Ser Lys Gly Ala Arg Phe Arg Gln Gly Lys
            935                 940                 945

GAC TAC GTT GGG GAG CTC TCC GTG GAT CTG AAA AGA CGC TTG GAC AGC         3174
Asp Tyr Val Gly Glu Leu Ser Val Asp Leu Lys Arg Arg Leu Asp Ser
        950                 955                 960

ATC ACC AGC AGC CAG AGC TCT GCC AGC TCA GGC TTT GTT GAG GAG AAA         3222
Ile Thr Ser Ser Gln Ser Ser Ala Ser Ser Gly Phe Val Glu Glu Lys
    965                 970                 975

TCG CTC AGT GAT GTA GAG GAA GAA GAA GCT TCT GAA GAA CTG TAC AAG         3270
Ser Leu Ser Asp Val Glu Glu Glu Glu Ala Ser Glu Glu Leu Tyr Lys
980                 985                 990                 995

GAC TTC CTG ACC TTG GAG CAT CTC ATC TGT TAC AGC TTC CAA GTG GCT         3318
Asp Phe Leu Thr Leu Glu His Leu Ile Cys Tyr Ser Phe Gln Val Ala
                1000                1005                1010

AAG GGC ATG GAG TTC TTG GCA TCA AGG AAG TGT ATC CAC AGG GAC CTG         3366
Lys Gly Met Glu Phe Leu Ala Ser Arg Lys Cys Ile His Arg Asp Leu
            1015                1020                1025

GCA GCA CGA AAC ATT CTC CTA TCG GAG AAG AAT GTG GTT AAG ATC TGT         3414
Ala Ala Arg Asn Ile Leu Leu Ser Glu Lys Asn Val Val Lys Ile Cys
        1030                1035                1040

GAC TTC GGC TTG GCC CGG GAC ATT TAT AAA GAC CCG GAT TAT GTC AGA         3462
Asp Phe Gly Leu Ala Arg Asp Ile Tyr Lys Asp Pro Asp Tyr Val Arg
    1045                1050                1055

AAA GGA GAT GCC CGA CTC CCT TTG AAG TGG ATG GCC CCG GAA ACC ATT         3510
Lys Gly Asp Ala Arg Leu Pro Leu Lys Trp Met Ala Pro Glu Thr Ile
1060                1065                1070                1075

TTT GAC AGA GTA TAC ACA ATT CAG AGC GAT GTG TGG TCT TTC GGT GTG         3558
```

```
Phe Asp Arg Val Tyr Thr Ile Gln Ser Asp Val Trp Ser Phe Gly Val
            1080                1085                1090

TTG CTC TGG GAA ATA TTT TCC TTA GGT GCC TCC CCA TAC CCT GGG GTC          3606
Leu Leu Trp Glu Ile Phe Ser Leu Gly Ala Ser Pro Tyr Pro Gly Val
            1095                1100                1105

AAG ATT GAT GAA GAA TTT TGT AGG AGA TTG AAA GAA GGA ACT AGA ATG          3654
Lys Ile Asp Glu Glu Phe Cys Arg Arg Leu Lys Glu Gly Thr Arg Met
            1110                1115                1120

CGG GCT CCT GAC TAC ACT ACC CCA GAA ATG TAC CAG ACC ATG CTG GAC          3702
Arg Ala Pro Asp Tyr Thr Thr Pro Glu Met Tyr Gln Thr Met Leu Asp
        1125                1130                1135

TGC TGG CAT GAG GAC CCC AAC CAG AGA CCC TCG TTT TCA GAG TTG GTG          3750
Cys Trp His Glu Asp Pro Asn Gln Arg Pro Ser Phe Ser Glu Leu Val
1140                1145                1150                1155

GAG CAT TTG GGA AAC CTC CTG CAA GCA AAT GCG CAG CAG GAT GGC AAA          3798
Glu His Leu Gly Asn Leu Leu Gln Ala Asn Ala Gln Gln Asp Gly Lys
            1160                1165                1170

GAC TAT ATT GTT CTT CCA ATG TCA GAG ACA CTG AGC ATG GAA GAG GAT          3846
Asp Tyr Ile Val Leu Pro Met Ser Glu Thr Leu Ser Met Glu Glu Asp
            1175                1180                1185

TCT GGA CTC TCC CTG CCT ACC TCA CCT GTT TCC TGT ATG GAG GAA GAG          3894
Ser Gly Leu Ser Leu Pro Thr Ser Pro Val Ser Cys Met Glu Glu Glu
            1190                1195                1200

GAA GTG TGC GAC CCC AAA TTC CAT TAT GAC AAC ACA GCA GGA ATC AGT          3942
Glu Val Cys Asp Pro Lys Phe His Tyr Asp Asn Thr Ala Gly Ile Ser
        1205                1210                1215

CAT TAT CTC CAG AAC AGT AAG CGA AAG AGC CGG CCA GTG AGT GTA AAA          3990
His Tyr Leu Gln Asn Ser Lys Arg Lys Ser Arg Pro Val Ser Val Lys
1220                1225                1230                1235

ACA TTT GAA GAT ATC CCA TTG GAG GAA CCA GAA GTA AAA GTG ATC CCA          4038
Thr Phe Glu Asp Ile Pro Leu Glu Glu Pro Glu Val Lys Val Ile Pro
            1240                1245                1250

GAT GAC AGC CAG ACA GAC AGT GGG ATG GTC CTT GCA TCA GAA GAG CTG          4086
Asp Asp Ser Gln Thr Asp Ser Gly Met Val Leu Ala Ser Glu Glu Leu
            1255                1260                1265

AAA ACT CTG GAA GAC AGG AAC AAA TTA TCT CCA TCT TTT GGT GGA ATG          4134
Lys Thr Leu Glu Asp Arg Asn Lys Leu Ser Pro Ser Phe Gly Gly Met
            1270                1275                1280

ATG CCC AGT AAA AGC AGG GAG TCT GTG GCC TCG GAA GGC TCC AAC CAG          4182
Met Pro Ser Lys Ser Arg Glu Ser Val Ala Ser Glu Gly Ser Asn Gln
        1285                1290                1295

ACC AGT GGC TAC CAG TCT GGG TAT CAC TCA GAT GAC ACA GAC ACC ACC          4230
Thr Ser Gly Tyr Gln Ser Gly Tyr His Ser Asp Asp Thr Asp Thr Thr
1300                1305                1310                1315

GTG TAC TCC AGC GAC GAG GCA GGA CTT TTA AAG ATG GTG GAT GCT GCA          4278
Val Tyr Ser Ser Asp Glu Ala Gly Leu Leu Lys Met Val Asp Ala Ala
            1320                1325                1330

GTT CAC GCT GAC TCA GGG ACC ACA CTG CAG CTC ACC TCC TGT TTA AAT          4326
Val His Ala Asp Ser Gly Thr Thr Leu Gln Leu Thr Ser Cys Leu Asn
            1335                1340                1345

GGA AGT GGT CCT GTC CCG GCT CCG CCC CCA ACT CCT GGA AAT CAC GAG          4374
Gly Ser Gly Pro Val Pro Ala Pro Pro Pro Thr Pro Gly Asn His Glu
            1350                1355                1360

AGA GGT GCT GCT TAGATTTTCA AGTGTTGTTC TTTCCACCAC CCGGAAGTAG             4426
Arg Gly Ala Ala
        1365

CCACATTTGA TTTTCATTTT TGGAGGAGGG ACCTCAGACT GCAAGGAGCT TGTCCTCAGG        4486

GCATTTCCAG AGAAGATGCC CATGACCCAA GAATGTGTTG ACTCTACTCT CTTTTCCATT        4546
```

```
CATTTAAAAG TCCTATATAA TGTGCCCTGC TGTGGTCTCA CTACCAGTTA AAGCAAAAGA    4606

CTTTCAAACA CGTGGACTCT GTCCTCCAAG AAGTGGCAAC GGCACCTCTG TGAAACTGGA    4666

TCGAATGGGC AATGCTTTGT GTGTTGAGGA TGGGTGAGAT GTCCCAGGGC CGAGTCTGTC    4726

TACCTTGGAG GCTTTGTGGA GGATGCGGGC TATGAGCCAA GTGTTAAGTG TGGGATGTGG    4786

ACTGGGAGGA AGGAAGGCGC AAGTCGCTCG GAGAGCGGTT GGAGCCTGCA GATGCATTGT    4846

GCTGGCTCTG GTGGAGGTGG GCTTGTGGCC TGTCAGGAAA CGCAAAGGCG GCCGGCAGGG    4906

TTTGGTTTTG GAAGGTTTGC GTGCTCTTCA CAGTCGGGTT ACAGGCGAGT TCCCTGTGGC    4966

GTTTCCTACT CCTAATGAGA GTTCCTTCCG GACTCTTACG TGTCTCCTGG CCTGGCCCCA    5026

GGAAGGAAAT GATGCAGCTT GCTCCTTCCT CATCTCTCAG GCTGTGCCTT AATTCAGAAC    5086

ACCAAAAGAG AGGAACGTCG GCAGAGGCTC CTGACGGGGC CGAAGAATTG TGAGAACAGA    5146

ACAGAAACTC AGGGTTTCTG CTGGGTGGAG ACCCACGTGG CGCCCTGGTG GCAGGTCTGA    5206

GGGTTCTCTG TCAAGTGGCG GTAAAGGCTC AGGCTGGTGT TCTTCCTCTA TCTCCACTCC    5266

TGTCAGGCCC CCAAGTCCTC AGTATTTTAG CTTTGTGGCT TCCTGATGGC AGAAAAATCT    5326

TAATTGGTTG GTTTGCTCTC CAGATAATCA CTAGCCAGAT TTCGAAATTA CTTTTTAGCC    5386

GAGGTTATGA TAACATCTAC TGTATCCTTT AGAATTTTAA CCTATAAAAC TATGTCTACT    5446

GGTTTCTGCC TGTGTGCTTA TGTT                                           5470
```

(2) INFORMATION FOR SEQ ID NO:2:

(i) SEQUENCE CHARACTERISTICS:
        (A) LENGTH: 1367 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Ser Lys Ala Leu Leu Ala Val Ala Leu Trp Phe Cys Val Glu
 1               5                  10                  15

Thr Arg Ala Ala Ser Val Gly Leu Thr Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190
```

```
Met Ile Ser Tyr Ala Gly Met Val Phe Cys Glu Ala Lys Ile Asn Asp
            195                 200                 205
Glu Thr Tyr Gln Ser Ile Met Tyr Ile Val Val Val Gly Tyr Arg
            210                 215                 220
Ile Tyr Asp Val Ile Leu Ser Pro Pro His Glu Ile Glu Leu Ser Ala
225                     230                 235                 240
Gly Glu Lys Leu Val Leu Asn Cys Thr Ala Arg Thr Glu Leu Asn Val
                245                 250                 255
Gly Leu Asp Phe Thr Trp His Ser Pro Pro Ser Lys Ser His His Lys
                260                 265                 270
Lys Ile Val Asn Arg Asp Val Lys Pro Phe Pro Gly Thr Val Ala Lys
                275                 280                 285
Met Phe Leu Ser Thr Leu Thr Ile Glu Ser Val Thr Lys Ser Asp Gln
                290                 295                 300
Gly Glu Tyr Thr Cys Val Ala Ser Ser Gly Arg Met Ile Lys Arg Asn
305                     310                 315                 320
Arg Thr Phe Val Arg Val His Thr Lys Pro Phe Ile Ala Phe Gly Ser
                325                 330                 335
Gly Met Lys Ser Leu Val Glu Ala Thr Val Gly Ser Gln Val Arg Ile
                340                 345                 350
Pro Val Lys Tyr Leu Ser Tyr Pro Ala Pro Asp Ile Lys Trp Tyr Arg
                355                 360                 365
Asn Gly Arg Pro Ile Glu Ser Asn Tyr Thr Met Ile Val Gly Asp Glu
                370                 375                 380
Leu Thr Ile Met Glu Val Thr Glu Arg Asp Ala Gly Asn Tyr Thr Val
385                     390                 395                 400
Ile Leu Thr Asn Pro Ile Ser Met Glu Lys Gln Ser His Met Val Ser
                405                 410                 415
Leu Val Val Asn Val Pro Pro Gln Ile Gly Glu Lys Ala Leu Ile Ser
                420                 425                 430
Pro Met Asp Ser Tyr Gln Tyr Gly Thr Met Gln Thr Leu Thr Cys Thr
                435                 440                 445
Val Tyr Ala Asn Pro Pro Leu His His Ile Gln Trp Tyr Trp Gln Leu
450                     455                 460
Glu Glu Ala Cys Ser Tyr Arg Pro Gly Gln Thr Ser Pro Tyr Ala Cys
465                     470                 475                 480
Lys Glu Trp Arg His Val Glu Asp Phe Gln Gly Asn Lys Ile Glu
                485                 490                 495
Val Thr Lys Asn Gln Tyr Ala Leu Ile Glu Gly Lys Asn Lys Thr Val
                500                 505                 510
Ser Thr Leu Val Ile Gln Ala Ala Asn Val Ser Ala Leu Tyr Lys Cys
                515                 520                 525
Glu Ala Ile Asn Lys Ala Gly Arg Gly Glu Arg Val Ile Ser Phe His
                530                 535                 540
Val Ile Arg Gly Pro Glu Ile Thr Val Gln Pro Ala Ala Gln Pro Thr
545                     550                 555                 560
Glu Gln Glu Ser Val Ser Leu Leu Cys Thr Ala Asp Arg Asn Thr Phe
                565                 570                 575
Glu Asn Leu Thr Trp Tyr Lys Leu Gly Ser Gln Ala Thr Ser Val His
                580                 585                 590
Met Gly Glu Ser Leu Thr Pro Val Cys Lys Asn Leu Asp Ala Leu Trp
                595                 600                 605
```

```
Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
            645                 650                 655

Leu Ile Ile Leu Glu Arg Met Ala Pro Met Ile Thr Gly Asn Leu Glu
        660                 665                 670

Asn Gln Thr Thr Thr Ile Gly Glu Thr Ile Glu Val Thr Cys Pro Ala
            675                 680                 685

Ser Gly Asn Pro Thr Pro His Ile Thr Trp Phe Lys Asp Asn Glu Thr
    690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
            725                 730                 735

Ala Cys Asn Val Leu Gly Cys Ala Arg Ala Glu Thr Leu Phe Ile Ile
        740                 745                 750

Glu Gly Ala Gln Glu Lys Thr Asn Leu Glu Val Ile Ile Leu Val Gly
            755                 760                 765

Thr Ala Val Ile Ala Met Phe Phe Trp Leu Leu Leu Val Ile Val Leu
    770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
            805                 810                 815

Arg Leu Pro Tyr Asp Ala Ser Lys Trp Glu Phe Pro Arg Asp Arg Leu
        820                 825                 830

Lys Leu Gly Lys Pro Leu Gly Arg Gly Ala Phe Gly Gln Val Ile Glu
            835                 840                 845

Ala Asp Ala Phe Gly Ile Asp Lys Thr Ala Thr Cys Lys Thr Val Ala
    850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
            885                 890                 895

Val Asn Leu Leu Gly Ala Cys Thr Lys Pro Gly Gly Pro Leu Met Val
        900                 905                 910

Ile Val Glu Phe Cys Lys Phe Gly Asn Leu Ser Thr Tyr Leu Arg Gly
    915                 920                 925

Lys Arg Asn Glu Phe Val Pro Tyr Lys Ser Lys Gly Ala Arg Phe Arg
930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
            965                 970                 975

Glu Glu Lys Ser Leu Ser Asp Val Glu Glu Glu Ala Ser Glu Glu
        980                 985                 990

Leu Tyr Lys Asp Phe Leu Thr Leu Glu His Leu Ile Cys Tyr Ser Phe
    995                 1000                1005

Gln Val Ala Lys Gly Met Glu Phe Leu Ala Ser Arg Lys Cys Ile His
    1010                1015                1020

Arg Asp Leu Ala Ala Arg Asn Ile Leu Leu Ser Glu Lys Asn Val Val
```

-continued

```
                1025                1030                1035                1040

Lys Ile Cys Asp Phe Gly Leu Ala Arg Asp Ile Tyr Lys Asp Pro Asp
                    1045                1050                1055

Tyr Val Arg Lys Gly Asp Ala Arg Leu Pro Leu Lys Trp Met Ala Pro
            1060                1065                1070

Glu Thr Ile Phe Asp Arg Val Tyr Thr Ile Gln Ser Asp Val Trp Ser
                1075                1080                1085

Phe Gly Val Leu Leu Trp Glu Ile Phe Ser Leu Gly Ala Ser Pro Tyr
            1090                1095                1100

Pro Gly Val Lys Ile Asp Glu Glu Phe Cys Arg Arg Leu Lys Glu Gly
1105                1110                1115                1120

Thr Arg Met Arg Ala Pro Asp Tyr Thr Thr Pro Glu Met Tyr Gln Thr
                1125                1130                1135

Met Leu Asp Cys Trp His Glu Asp Pro Asn Gln Arg Pro Ser Phe Ser
                1140                1145                1150

Glu Leu Val Glu His Leu Gly Asn Leu Leu Gln Ala Asn Ala Gln Gln
            1155                1160                1165

Asp Gly Lys Asp Tyr Ile Val Leu Pro Met Ser Glu Thr Leu Ser Met
        1170                1175                1180

Glu Glu Asp Ser Gly Leu Ser Leu Pro Thr Ser Pro Val Ser Cys Met
1185                1190                1195                1200

Glu Glu Glu Glu Val Cys Asp Pro Lys Phe His Tyr Asp Asn Thr Ala
                1205                1210                1215

Gly Ile Ser His Tyr Leu Gln Asn Ser Lys Arg Lys Ser Arg Pro Val
                1220                1225                1230

Ser Val Lys Thr Phe Glu Asp Ile Pro Leu Glu Glu Pro Glu Val Lys
            1235                1240                1245

Val Ile Pro Asp Asp Ser Gln Thr Asp Ser Gly Met Val Leu Ala Ser
    1250                1255                1260

Glu Glu Leu Lys Thr Leu Glu Asp Arg Asn Lys Leu Ser Pro Ser Phe
1265                1270                1275                1280

Gly Gly Met Met Pro Ser Lys Ser Arg Glu Ser Val Ala Ser Glu Gly
                1285                1290                1295

Ser Asn Gln Thr Ser Gly Tyr Gln Ser Gly Tyr His Ser Asp Asp Thr
                1300                1305                1310

Asp Thr Thr Val Tyr Ser Ser Asp Glu Ala Gly Leu Leu Lys Met Val
            1315                1320                1325

Asp Ala Ala Val His Ala Asp Ser Gly Thr Thr Leu Gln Leu Thr Ser
        1330                1335                1340

Cys Leu Asn Gly Ser Gly Pro Val Pro Ala Pro Pro Thr Pro Gly
1345                1350                1355                1360

Asn His Glu Arg Gly Ala Ala
            1365
```

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:3:

GTCATGGATC TTCGTTAA                                        18

(2) INFORMATION FOR SEQ ID NO:4:

(i) SEQUENCE CHARACTERISTICS:
       (A) LENGTH: 33 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO:4:

TTGTACAAGT ATAAGTAGTA GCCCAGGTAC CAG           33

(2) INFORMATION FOR SEQ ID NO:5:

(i) SEQUENCE CHARACTERISTICS:
       (A) LENGTH: 806 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:5:

```
Met Glu Ser Lys Ala Leu Leu Ala Val Ala Leu Trp Phe Cys Val Glu
1               5                   10                  15

Thr Arg Ala Ala Ser Val Gly Leu Thr Gly Asp Phe Leu His Pro Pro
                20                  25                  30

Lys Leu Ser Thr Gln Lys Asp Ile Leu Thr Ile Leu Ala Asn Thr Thr
            35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
                100                 105                 110

Ala Ser Thr Val Tyr Val Tyr Val Arg Asp Tyr Arg Ser Pro Phe Ile
            115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
                180                 185                 190

Met Ile Ser Tyr Ala Gly Met Val Phe Cys Glu Ala Lys Ile Asn Asp
            195                 200                 205

Glu Thr Tyr Gln Ser Ile Met Tyr Ile Val Val Val Gly Tyr Arg
    210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
                260                 265                 270
```

-continued

```
Lys Ile Val Asn Arg Asp Val Lys Pro Phe Pro Gly Thr Val Ala Lys
            275                 280                 285

Met Phe Leu Ser Thr Leu Thr Ile Glu Ser Val Thr Lys Ser Asp Gln
    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
            355                 360                 365

Asn Gly Arg Pro Ile Glu Ser Asn Tyr Thr Met Ile Val Gly Asp Glu
370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
            435                 440                 445

Val Tyr Ala Asn Pro Pro Leu His His Ile Gln Trp Tyr Trp Gln Leu
    450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                485                 490                 495

Val Thr Lys Asn Gln Tyr Ala Leu Ile Glu Gly Lys Asn Lys Thr Val
            500                 505                 510

Ser Thr Leu Val Ile Gln Ala Ala Asn Val Ser Ala Leu Tyr Lys Cys
            515                 520                 525

Glu Ala Ile Asn Lys Ala Gly Arg Gly Glu Arg Val Ile Ser Phe His
    530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
            595                 600                 605

Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
            675                 680                 685
```

-continued

```
Ser Gly Asn Pro Thr Pro His Ile Thr Trp Phe Lys Asp Asn Glu Thr
        690             695             700
Leu Val Glu Asp Ser Gly Ile Val Leu Arg Asp Gly Asn Arg Asn Leu
705                 710             715                 720
Thr Ile Arg Arg Val Arg Lys Glu Asp Gly Gly Leu Tyr Thr Cys Gln
                725             730             735
Ala Cys Asn Val Leu Gly Cys Ala Arg Ala Glu Thr Leu Phe Ile Ile
            740             745             750
Glu Gly Ala Gln Glu Lys Thr Asn Leu Glu Val Ile Ile Leu Val Gly
        755             760             765
Thr Ala Val Ile Ala Met Phe Phe Trp Leu Leu Leu Val Ile Val Leu
        770             775             780
Arg Thr Val Lys Arg Ala Asn Glu Gly Glu Leu Lys Thr Gly Tyr Leu
785                 790             795                 800
Ser Ile Val Met Asp Pro
```

(2) INFORMATION FOR SEQ ID NO:6:

(i) SEQUENCE CHARACTERISTICS:
  (A) LENGTH: 180 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:6:

```
Ile Leu Ile His Ile Gly His His Leu Asn Val Val Asn Leu Leu Gly
1               5                   10                  15
Ala Cys Thr Lys Pro Gly Gly Pro Leu Met Val Ile Val Glu Phe Cys
            20                  25                  30
Lys Phe Gly Asn Leu Ser Thr Tyr Leu Arg Gly Lys Arg Asn Glu Phe
        35                  40                  45
Val Pro Tyr Lys Ser Lys Gly Ala Arg Phe Arg Gln Gly Lys Asp Tyr
50                  55                  60
Val Gly Glu Leu Ser Val Asp Leu Lys Arg Arg Leu Asp Ser Ile Thr
65                  70                  75                  80
Ser Ser Gln Ser Ser Ala Ser Ser Gly Phe Val Glu Glu Lys Ser Leu
                85                  90                  95
Ser Asp Val Glu Glu Glu Glu Ala Ser Glu Glu Leu Tyr Lys Asp Phe
                100                 105                 110
Leu Thr Leu Glu His Leu Ile Cys Tyr Ser Phe Gln Val Ala Lys Gly
            115                 120                 125
Met Glu Phe Leu Ala Ser Arg Lys Cys Ile His Arg Asp Leu Ala Ala
        130                 135                 140
Arg Asn Ile Leu Leu Ser Glu Lys Asn Val Val Lys Ile Cys Asp Phe
145                 150                 155                 160
Gly Leu Ala Arg Asp Ile Tyr Lys Asp Pro Asp Tyr Val Arg Lys Gly
                165                 170                 175
Asp Ala Arg Leu
            180
```